(12) United States Patent
Chilton et al.

(10) Patent No.: US 9,663,824 B2
(45) Date of Patent: May 30, 2017

(54) COMPOSITIONS AND METHODS FOR EPIGENETIC REGULATION OF LONG CHAIN POLYUNSATURATED FATTY ACID PRODUCTION

(71) Applicant: Wake Forest University Health Sciences, Winston-Salem, NC (US)

(72) Inventors: Floyd H. Chilton, Clemmons, NC (US); Timothy D. Howard, Clemmons, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 15/028,323

(22) PCT Filed: Oct. 10, 2014

(86) PCT No.: PCT/US2014/060153
§ 371 (c)(1),
(2) Date: Apr. 8, 2016

(87) PCT Pub. No.: WO2015/054645
PCT Pub. Date: Apr. 16, 2015

(65) Prior Publication Data
US 2016/0244840 A1  Aug. 25, 2016

Related U.S. Application Data

(60) Provisional application No. 61/889,178, filed on Oct. 10, 2013.

(51) Int. Cl.
*C12Q 1/68* (2006.01)
*A61K 31/202* (2006.01)
*A23L 1/30* (2006.01)

(52) U.S. Cl.
CPC .......... *C12Q 1/6883* (2013.01); *A23L 1/3008* (2013.01); *A61K 31/202* (2013.01); *A23V 2002/00* (2013.01); *C12Q 2600/118* (2013.01); *C12Q 2600/154* (2013.01); *C12Q 2600/156* (2013.01)

(58) Field of Classification Search
CPC .... C12Q 1/6883; A61K 31/202; A23L 1/3008
See application file for complete search history.

(56) References Cited

U.S. PATENT DOCUMENTS

| 5,223,409 A | 6/1993 | Ladner et al. |
| 5,403,484 A | 4/1995 | Ladner et al. |
| 5,571,698 A | 11/1996 | Ladner et al. |
| 2010/0116980 A1 | 5/2010 | Nassif et al. |
| 2011/0287975 A1* | 11/2011 | Chilton ............... C12Q 1/6883 506/12 |

OTHER PUBLICATIONS

Glaser et al. "Role of FADS1 and FADS2 polymorphisms in polyunsaturated fatty acid metabolism" *Metabolism—Clinical and Experimental* 59(7):993-999 (2010) (Abstract Only; 1 page).
Glaser et al. "Genetic variation in polyunsaturated fatty acid metabolism and its potential relevance for human development and health" *Maternal & Child Nutrition* 7(Suppl. 2):27-40 (2011).
Howard et al. "DNA Methylation in an Enhancer Region of the FADS Cluster Is Associated with FADS Activity in Human Liver" *PloS One* 9(5):e97510 (2014).
International Search Report and the Written Opinion of the International Searching Authority corresponding to International Patent Application No. PCT/US2014/060153 (14 pages) (mailed Jan. 15, 2015).
Reardon et al. "Dietary long-chain polyunsaturated fatty acids upregulate expression of FADS3 transcripts" *Prostaglandins Leukotrienes and Essential Fatty Acids* 88(1):15-19 (2013).
Xie et al. "Genetic Variants of the FADS1 FADS2 Gene Cluster Are Associated with Altered (n-6) and (n-3) Essential Fatty Acids in Plasma and Erythrocyte Phospholipids in Women during Pregnancy and in Breast Milk during Lactation" *The Journal of Nutrition* 138:2222-2228 (2008).
Aulchenko et al. "Loci influencing lipid levels and coronary heart disease risk in 16 European population cohorts" *Nature Genetics* 41(1):47-55 (2009).
Barrett et al. "Haploview: analysis and visualization of LD and haplotype maps" *Bioinformatics* 21(2):263-265 (2005).
Blanchard et al. "Fatty Acid Desaturase 3 (Fads3) is a singular member of the Fads cluster" *Biochimie* 93(1):87-90 (2011) (Abstract Only).
Blasbalg et al. "Changes in consumption of omega-3 and omega-6 fatty acids in the United States during the $20^{th}$ century" *The American Journal of Clinical Nutrition* 93:950-962 (2011).
Carell et al. "A Solution-Phase Screening Procedure for the Isolation of Active Compounds from a Library of Molecules" *Angewandte Chemie International Edition* 33(20):2061-2064 (1994).
Cho et al. "An Unnatural Biopolymer" *Science* 261(5126):1303-1305 (1993).
Cull et al. "Screening for receptor ligands using large libraries of peptides linked to the C terminus of the lac repressor" *Proceedings of the National Academy of Sciences* 89:1865-1869 (1992).
Cwirla et al. "Peptides on phase: A vast library of peptides for identifying ligands" *Proceedings of the National Academy of Sciences* 87:6378-6382 (1990).
Devlin et al. "Random Peptide Libraries: A Source of Specific Protein Binding Molecules" *Science* 249(4967):404-406 (1990).
Dewitt et al. "'Diversomers': An approach to nonpeptide, nonoligomeric chemical diversity" *Proceedings of the National Academy of Sciences* 90:6909-6913 (1993).
El Khechine et al. "Matrix-Assisted Laser Desorption/Ionization Time-of-Flight Mass Spectrometry Identification of Mycobacteria in Routine Clinical Practice" *PLoS One* 6(9):e24720 (2011).
Erb et al. "Recursive deconvolution of combinatorial chemical libraries" *Proceedings of the National Academy of Sciences* 91:11422-11426 (1994).
Felici et al. "Selection of antibody ligands from a large library of oligopeptides expressed on a multivalent exposition vector" *Journal of Molecular Biology* 222(2):301-310 (1991) (Abstract Only).
Fodor et al. "Multiplexed biochemical assays with biological chips" *Nature* 364(6437):555-556 (1993).

(Continued)

*Primary Examiner* — Erich A Leeser
(74) *Attorney, Agent, or Firm* — Myers Bigel, P.A.

(57) ABSTRACT

Compositions and methods for identifying and treating patients having altered capacity for LC-PUFA production are disclosed.

34 Claims, 20 Drawing Sheets

(56) References Cited

OTHER PUBLICATIONS

Frangou et al. "Efficacy of ethyl-eicosapentaenoic acid in bipolar depression: randomised double-blind placebo-controlled study" *The British Journal of Psychiatry* 188:46-50 (2006).
Gallop et al. "Applications of Combinatorial Technologies to Drug Discovery. 1. Background and Peptide Combinatorial Libraries" *Journal of Medicinal Chemistry* 37(9):1233-1251 (1994) (Abstract Only).
Gibbs et al. "Abundant Quantitative Trait Loci Exist for DNA Methylation and Gene Expression in Human Brain" *PLoS Genetics* 6(5):e1000952 (2010).
Gieger et al. "Genetics Meets Metabolomics: A Genome-Wide Association Study of Metabolite Profiles in Human Serum" *PLoS Genetics* 4(11):e1000282 (2008).
Haggarty, Paul "Fatty Acid Supply to the Human Fetus" *Annual Review of Nutrition* 30:237-255 (2010).
Hawkey et al. "Omega-3 fatty acid and ADHD: Blood level analysis and meta-analytic extension of supplementation trials" *Clinical Psychology Review* 34(6):496-505 (2014).
Hibbeln et al. "Omega-3 fatty acid deficiencies in neurodevelopment, aggression and autonomic dysregulation: Opportunities for intervention" *International Review of Psychiatry* 18(2):107-118 (2006).
Hindorff et al. "Potential etiologic and functional implications of genome-wide association loci for human diseases and traits" *Proceedings of the National Academy of Sciences* 106(23):9362-9367 (2009).
Hong et al. "Association of polymorphisms in *FADS* gene with age-related changes in serum phospholipid polyunsaturated fatty acids and oxidative stress markers in middle-aged nonobese men" *Clinical Interventions in Aging* 8:585-596 (2013).
Houghten et al. "The use of synthetic peptide combinatorial libraries for the identification of bioactive peptides" *BioTechniques* 13(3):412-421 (1992) (Abstract Only).
Illig et al. "A genomewide perspective of genetic variation in human metabolism" *Nature Genetics* 42(2):137-141 (2010).
Jones, Peter A. "Functions of DNA methylation: islands, start sites, gene bodies and beyond" *Nature Reviews Genetics* 13:484-492 (2012).
Kathiresan et al. "Six new loci associated with blood low-density lipoprotein cholesterol, high-density lipoprotein cholesterol or triglycerides in humans" *Nature Genetics* 40(2):189-197 (2008).
Kathiresan et al. "Common variants at 30 loci contribute to polygenic dyslipidemia" *Nature Genetics* 41(1):56-65 (2009).
Lam et al. "A new type of synthetic peptide library for identifying ligand-binding activity" *Nature* 354(6348):82-84 (1991).
Lam, K. "Application of combinatorial library methods in cancer research and drug discovery" *Anti-Cancer Drug Design* 12(3):145-167 (1997) (Abstract Only).
Lattka et al. "FADS Gene Cluster Polymorphisms: Important Modulators of Fatty Acid Levels and Their Impact on Atopic Diseases" *Journal of Nutrigenetics and Nutrigenomics* 2:119-128 (2009).
Lewis et al. "Suicide Deaths of Active Duty U.S. Military and Omega-3 Fatty Acid Status: A Case Control Comparison" *Journal of Clinical Psychiatry* 72(12):1585-1590 (2011).
Lewis et al. "Therapeutic use of omega-3 fatty acids in severe head trauma" *The American Journal of Emergency Medicine* 31(1):273. e5-273.e8 (2013).
Lister et al. "Human DNA methylomes at base resolution show widespread epigenomic differences" *Nature* 462:315-322 (2009).
Marquardt et al. "cDNA cloning, genomic structure, and chromosomal localization of three members of the human fatty acid desaturase family" *Genomics* 66(2):175-183 (2000) (Abstract Only).
Martinelli et al. "FADS genotypes and desaturase activity estimated by the ratio of arachidonic acid to linoleic acid are associated with inflammation and coronary artery disease" *The American Journal of Clinical Nutrition* 88:941-949 (2008).
Mathias et al. "The impact of *FADS* genetic variants on ω6 polyunsaturated fatty acid metabolism in African Americans" *BMC Genetics* 12(50):1-10 (2011).
Mathias et al. "Adaptive Evolution of the *FADS* Gene Cluster within Africa" *PLoS One* 7(9):e44926 (2012).
Metcalfe et al. "Rapid Preparation of Fatty Acid Esters from Lipids for Gas Chromatographic Analysis" *Analytical Chemistry* 38(3):514-515 (1966) (Abstract Only).
Needleman et al. "Arachidonic Acid Metabolism" *Annual Review of Biochemistry* 55:69-102 (1986).
Park et al. "Interactions between the APOA5-1131T>C and the FEN1 10154G>T polymorphisms on ω6 polyunsaturated fatty acids in serum phospholipids and coronary artery disease" *Journal of Lipid Research* 51:3281-3288 (2010).
Reference SNP (RefSNP) Cluster Report: rs174537 (3 pages) (Jun. 2016).
Schadt et al. "Mapping the Genetic Architecture of Gene Expression in Human Liver" *PLoS Biology* 6(5):e107 (2008).
Schmidl et al. "Lineage-specific DNA methylation in T cells correlates with histone methylation and enhancer activity" *Genome Research* 19:1165-1174 (2009).
Scott et al. "Searching for Peptide Ligands with an Epitope Library" *Science* 249(4967):386-390 (1990).
Sergeant et al. "Differences in Arachidonic Acid Levels and Fatty Acid Desaturase (FADS) Gene Variants in African Americans and European Americans with Diabetes/Metabolic Syndrome" *British Journal of Nutrition* 107(4):547-555 (2012).
Sigurdsson et al. "HapMap methylation-associated SNPs, markers of germline DNA methylation, positively correlate with regional levels of human meiotic recombination" *Genome Research* 19:581-589 (2009).
Wang et al. "Eicosanoids and cancer" *Nature Reviews Cancer* 10(3):181-193 (2010).
Weaver et al. "Effect of Dietary Fatty Acids on Inflammatory Gene Expression in Healthy Humans" *The Journal of Biological Chemistry* 284(23):15400-15407 (2009).
Wiench et al. "DNA methylation status predicts cell type-specific enhancer activity" *The EMBO Journal* 30:3028-3039 (2011).
Willer et al. "Newly identified loci that influence lipid concentrations and risk of coronary artery disease" *Nature Genetics* 40(2):161-169 (2008).
Willer et al. "METAL: fast and efficient meta-analysis of genomewide association scans" *Bioinformatics* 26(17):2190-2191 (2010).
Wissler, R. "Update on the pathogenesis of atherosclerosis" *The American Journal of Medicine* 91(1B): 3S-9S (1991) (Abstract Only).
Zhang et al. "Genetic Control of Individual Differences in Gene-Specific Methylation in Human Brain" *The American Journal of Human Genetics* 86:411-419 (2010).
Zuckermann et al. "Discovery of Nanomolar Ligands for 7-Transmembrane G-Protein-Coupled Receptors from a Diverse N-(Substituted)glycine Peptoid Library" *Journal of Medicinal Chemistry* 37(17):2678-2685 (1994).

* cited by examiner

```
8751  TGCAGAGCCC ATTAAACTGG AATTAATCCT TGGGAGCAGG GAATGGGGGA
8801  GAATTATTTC TGCTAGCGTA GCTTAGCAAA TACAGCCATA TTTTTTTGTC
8851  ACATGGAGGA GACCCTTCTG CAGTAAGAGA GAATCAGGTG TTGGCCGGGT
8901  GCAGTGGCTC ACGCCTGTAA TCCCAGCACT TTGGGAGGCT GAGGTGGGCA
8951  GATCACGAGG TCAGGAGATC GAGACCATCA TGGCCAACAT GGTGAAACCC
9001  CATCTCTACT AAAAATACAA AAATTATCTG GGCATGGTGC CACCCACCAC
9051  GCCTCCTAA AGTGCTGGGA TTATAGGCAT AAGCCACTGC TCCCAGCCTA
9101  GGTGTTTCAA ACATAACGTT AAAATAGAAT TTTTAATTTT TCACCCCTGT
9151  ACTAACTCTG TTCCCTCATC TTGGTAAATG GTCCCATTAT CTATTCATTT
9201  GCTCAACTCA AATGCTAGAA TCAGACTTAT TTCTCTTATT CCTTCATCTC
9251  TACCATACC CCTGCCCTG TCCTCCAAC TAATGGGTC TTGATTCTAC
9301  CTCCAAAGGA TATTCTAGGC TGGGCAGGGT GGCTCACGCC TGTAATCCCA
9351  GCACTCTGGG AGGCTGAGGT GGGCAGATCA CCTGAGGTCA GGAGTTTGAG
9401  ACCAGCCTGG CCAACATGCT GAAACCCTGT CTCTACTAAA AATATAAAAA
9451  TTAGCCGGGC ATGGTGGCGG GTGCTTGTAA TCCCAGCTAC TCAGGAGGCT
9501  GAGGCAGTAG AACCATTTGA ACCCATGAGG TGGAGGTTGC AGTGAGCTGA
9551  GATCGCACCA CTGCACTCCA GCCTGGGCGA CAGAGTGAGA CCCTGTCTCA
9601  AAAAAAAAAA AAAAGAAAG AAAAAGCCCT TTGGGAGCCC GAGGCAGGTG
9651  GATCACGAGG TCAGGAGATC GAGACCATCC TGGCTAACAC GGTGAAACCC
9701  CGTCTCTACT AAAAATACAA AAAATTAGCC GGGTGTGGT GGCAGGCGCC
9751  TGTAGTCCCA GCTACTCGGG AGGCTGAGGC AGGAGAATGG CGTGAACCTG
9801  GGAGGTGGAG CTTGCAGTGA GTAGAGATCG CACCACTGCA CTCTAGCCTG
9851  GGCACAGAG TGAGACTGCA TCTCAAAAAA AAATTAGAGG GCAGGGAGGC
9901  ACATGGCAGT GTCCAGTGTG GGGTCAGCCC CCTAAGTTC TCTCTTAATT
9951  CAGCCTTCCC CTCCCTCTC CTGGAGCACT GCCCTCATCT TTGAACTCAT
10001 CACTGTTCCC CAGTTTCTCC CGTACATCCC AGTCCAGCCC CAGCCTCTGG
10051 AGTTATCTTT CTACACCATG GATCTGATCA CAGTACACCT GCTTTACGGA
10101 TGTCCAAGCC TCCTCCATGG TAAAGTCCTC CCTTCTTACC CCTTACTGAG
10151 GCTGCTGGGG CTTTTCTCAA TTGAGCCCCC ATTTACCGCC GGCCTCATTG
10201 GAGCCATTCT TTGAACTTCA TTCATTCATT TGTGTCTTCA ACACATGTTT
10251 TTATGTTTTT TCAGGACCTA CCCTGGCTGG TACTGTCTG GGAGCCGCTG
10301 GGGATCCAG GCCCTGGCCG GTCCACGCTT CTCAGCCACC CTACACAGGT
10351 CACCCATACG TGCTCCCTTT TAGGGCCTGA ACCTCAAAG CCTCTGTGAG
10401 ATACTCCCTG GTTCTCCCTT TCAGCTATCA CTCCCTGCTC GGAGCTCCAC
10451 ACCCTTTACA AATGTTCATT AAAGTTATCT ATATGGTAGG TTAATCCATT
10501 TCTGAGAAAA TAATTTTCTT GGTTCCATTT CCGTCAACGT TTGACAGTCC
10551 TCAAGCCAC CATACTCTCT GGAGGTCTTG CTTCATCCTC TTATTTTGTA
10601 CAGAAGGCTT TTGTTTGGCA TGTCTGCTCA CACTCAAAGA CAGAGAGGCC
10651 TTACTGTCTT TATGTCTGCA GTCTGTGGAG TGAATGAAGG ATGCTCAGGG
10701 CTGACACCAG CATGAAATGT GATGGGAGAG GTTGGGGACT GTGTGAATGT
10751 GAGGAAAGGG AGCCCATCTG CCCCCCCAAG TACAACCCCA CCAGTTGGGC
10801 ACAGTGATCC CCCCACCAC CTGCATTGC TGTGAAATTT AGATTGGGCA
10851 GGGCCGTTT GACCATCTCT CTCAATCTCA GGCTCTCCAT TTCAAGTGA
10901 GATGTAATAA TATGCGTCCT GTTTACCTCT CAGCCTGTGA TGAAATCTA
10951 ATGATTAGGG TGTGCTAGCA CACAGGCACC TGTAAATCCC ATTGAAATCT
11001 GAGGCCCTA TAACTCCTCT AGTGATTCCC AAGCCTCCTG CACCCCACCC
11051 TCTCTGTTCA TCCTTACTTC CCACGTGTCC CGTTAGCCCT CCGGATGCAG
11101 TCAGGCCCAT TTCCCCCACG ACCCCGGCA CTAAGCCCC CCATCCAGCT
11151 GGGGTCTGAG GGGCCTGTCT CTTGCCCCAC GCCTAAAAGA GCTAACCCTC
```

COMPOSITIONS AND METHODS FOR EPIGENETIC REGULATION OF LONG CHAIN POLYUNSATURATED FATTY ACID PRODUCTION

STATEMENT OF PRIORITY

This application is a 35 U.S.C. §371 national phase application of International Application Serial No. PCT/US2014/060153, filed Oct. 10, 2014, which claims the benefit, under 35 U.S.C. §119(e), of U.S. Provisional Application Ser. No. 61/889,178, filed Oct. 10, 2013, the entire contents of each of which are incorporated by reference herein.

STATEMENT OF GOVERNMENT SUPPORT

This invention was made with government support under Grant No. P50 AT002782 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. §1.821, entitled 9151-217 ST25.txt, 22,723 bytes in size, generated on Apr. 8, 2016 and filed via EFS-Web is provided in lieu of a paper copy. This Sequence Listing is hereby incorporated by reference into the specification for its disclosures.

FIELD OF THE INVENTION

This invention relates to the fields of molecular biology, genetics, epigenetics and polyunsaturated fatty acid (PUFA) synthesis and metabolism. More specifically, the present invention provides compositions and methods of use thereof having utility in the diagnosis and treatment of disorders associated with reduced or aberrant PUFA production.

BACKGROUND OF THE INVENTION

Levels of omega-6 (n-6) and omega-3 (n-3), long chain polyunsaturated fatty acids (LcPUFAs) such as arachidonic acid (AA; 20:4, n-6), eicosapentaenoic acid (EPA; 20:5, n-3) and docosahexaenoic acid (DHA; 22:6, n-3) impact a wide range of biological activities including immune signaling, inflammation, brain development and function as well as human diseases ranging from cardiovascular disease (including heart disease and stroke), diabetes, cancers, Alzheimer's disease and mental disorders. Two desaturase steps ($\Delta 6$ and $\Delta 5$) are rate limiting in the conversion of dietary essential, medium chain, 18 carbon PUFAs (McPUFAs) such as LA (18:2, n-6) to AA and $\alpha$-linolenic acid (ALA, 18:3, n-3) to EPA and DHA (FIG. 1). Marquardt and colleagues first discovered the presence of the fatty acid desaturase (FADS) gene family (the FADS cluster) on chromosome 11q12~13 in humans that appeared to be essential for the synthesis of LcPUFAs. FADS1 and FADS2 were demonstrated to code for the enzymes, $\Delta 5$ and $\Delta 6$ desaturase, respectively. Believed to have arisen through gene duplication, FADS1 and FADS2 are both central to LcPUFA biosynthesis. There is considerable linkage disequilibrium (LD) in this region and genome wide association studies (GWAS) and candidate gene studies have consistently identified as many as 100 single nucleotide polymorphisms (SNPs) within FADS1 and FADS2 as determinants of FADS1 and FADS2 desaturase efficiencies and levels of LcPUFAs in circulating, cellular and breast milk lipids.

There are dramatic differences in the genetic capacity of different individuals and populations to synthesize LcPUFAs and these differences are largely due to variation in and around the FADS cluster. When humans consume a modern western diet with very high levels of n-6 medium chain PUFAs and with much lower levels of n-3 medium chain (18 carbon) PUFAs, gene-diet interactions (as a result of variation FADS1 and FADS2) in LcPUFA biosynthesis create LcPUFA deficiencies (specifically n-3 LcPUFAs) in certain individuals within populations and excesses (specifically n-6 LcPUFAs) in others, all leading to human diseases and disorders.

Certain n-6 LcPUFAs, particularly arachidonic acid (ARA), play a key role in orchestrating a wide variety of inflammatory diseases, and consequently, an individual's capacity to synthesize ARA plays a role in the incidence and impact of inflammatory diseases. Numerous gene-wide association and candidate gene studies have now demonstrated that genetic variation in the FADS cluster together with consumption of the modern western diet causes markedly enhanced arachidonic acid levels, biomarkers of human disease, as well as the diseases themselves in certain humans. For example, SNPs in and around the FADS cluster that are associated with excesses of the n-6 LcPUFA, arachidonic acid are also associated with important cardiovascular disease risk factors [total, LDL, and HDL cholesterol, triglycerides, C-reactive protein (CRP) and pro-inflammatory eicosanoids] as well as coronary artery disease, metabolic syndrome and diabetes.

With regard to n-3 LcPUFAs, the n-3 LcPUFA, docosahexaenoic acid (DHA; 22:6, n-3), is the most abundant fatty acid in the brain and retina, constituting 50% of the weight of the neuron's plasma membrane. N-3 LcPUFAs are not only structurally important, as they are essential for proper brain function and development. DHA plays a critical role in neurogenesis; and adequate dietary DHA and other LcPUFAs are essential for visual, neural and cognitive development in the developing fetus and young infants. Dietary LcPUFA intake by pregnant and breast feeding mothers impacts brain development and function of a developing fetus and young child. The second trimester until two years of age appears to be an especially sensitive period of time (FIG. 2). The biosynthetic capacity of mother, developing fetus and young child to make LcPUFAs and particularly DHA has been shown be very important to brain development and function with diet-FADS gene (largely as a result of the modern western diet) interactions leading to cognitive, behavioral deficits and developmental, neurological and mood disorders. Specifically, there have been associations with variation in the FADS cluster and with cognitive development, and in particular, with those mothers and fetuses with little genetic (FADS) capacity to synthesize n-3 LcPUFAs being at highest risk.

Diagnostic surveys in 60,463 adults in 14 countries around the world found mental illness in 26.4% (over 50 million) of people in the US with much lower percentages in developing, especially African countries (e.g., only 4.7% of Nigerians). Additionally, these numbers are increasing dramatically (3 and 35 fold-increase since 1987 in adults and children, respectively, receiving federal aid). Currently, four of the ten leading causes of disability in the US are estimated to be mental disorders. In addition, developmental and neurological disorders (such as attention deficient disorder, autism and obsessive compulsive disorder continue to increase at an alarming rate, particularly in children.

It is not only the fetus and young children who are at risk of omega-3 deficiency; FIG. 3 shows a dramatic decrease in circulating (blood) levels of omega-3 (n-3) LcPUFAs over the past 75 years. Our studies further demonstrate that there are numerous individuals within a given population (African Americans and European Americans) that have very low levels of circulating n-3 LcPUFAs such as DHA (FIG. 4). Numerous studies have examined associations between the fatty acid composition of peripheral blood compartments (red blood cells, plasma or serum components), and postmortem brain tissue and psychiatric illnesses, mood and developmental disorders and dementia. These studies have found abnormalities in the fatty acid composition when subjects are compared to controls. Major depressive disorder is perhaps the most studied with regard to n-3 LcPUFA composition; a recent meta-analysis of 14 studies concluded that patients with depression had significantly lower n-3 LcPUFAs in blood compartments then control subjects. A few studies have examined postmortem brain tissue. However, McNamara and colleagues found that postmortem orbitofrontal cortex from patients with schizophrenia, bipolar disorder and major depressive disorder all had significantly lower amounts of DHA when compared to control subjects. In regard to developmental disorders such as ADHD, a recent meta-analysis in nine studies (n=586) found significantly lower blood levels of n-3 LcPUFAs in ADHD children versus controls and concluded that n-3 LcPUFAs are reduced in children with ADHD (Hawkey and Nigg. 2014, *Clin. Psychological Rev.* 34:496-505). The last two decades have shown a dramatic, unexplained rise in the prevalence of autism spectrum disorders (ASD) in children. Although only a few studies have examined associations between LcPUFAs and ASD, these studies suggest higher ratios of n-6 to n-3 LcPUFAs exist due to excess levels in-6 LcPUFAs and deficiencies in n-3 LcPUFAs.

Animal and human studies indicate that the absence of n-3 LcPUFAs during brain formation and later in life can create n-3 LcPUFA deficiencies and have profound adverse consequences for mood and neurological disorders and optimal brain function in adults (Hibbeln et al. 2006. *Int Rev Psychiatry* 18(2):107-18). Epidemiologically, brain tissue composition and randomized clinical trials have suggested that the western diet has created n-3 LcPUFA deficiencies in significant proportions of humans on western diets (FIGS. 3 and 4) and demonstrated the benefits of dietary n-3 LcPUFAs, especially for uni- and bipolar depression, schizophrenia and attention-deficit/hyperactivity disorder (ADHD). Schizophrenia is particularly interesting where several groups have shown n-3 LcPUFA deficiency is a critical 'risk factor'. Amminger and colleagues demonstrated that n-3 LcPUFA supplementation dramatically reduced the development of psychosis in individuals at higher risk. Brookes and colleagues showed an association between a SNP in the FADS cluster (FADS1 and FADS2) with ADHD cases. This result is supported by three previous linkage scans for ADHD, two of which have identified a significant linkage peak which is overlapping with the location of the FADS1 and FADS2 genes. It has been shown that ADHD subjects have deficiencies in plasma n-3 LcPUFAs compared to control subjects.

Currently there are no verified available biomarkers for post-traumatic stress disorders (PTSD) to identify who is at risk or who might benefit from a specific therapy. Numerous studies suggest that synatoneogenesis and neuronal plasticity are important for repair of brain tissue injury, including psychological traumas. Levels of n-3 LcPUFAs have been demonstrated to be involved in these processes. A case-control of active-duty suicides indicated lower serum levels of the n-3 LcPUFA, DHA were associated with a marked increase in suicide risk.

Taken together, major differences in the frequencies of FADS variants that vary the synthesis of LcPUFAs in individuals and populations make the possibility of uniform PUFA nutritional recommendations impossible. To understand individual risk of a PUFA-induced inflammatory disorder including cardiovascular disease, diabetes, arthritis, asthma, Alzheimer's disease and cancer caused by making an excess of n-6 LcPUFAs or risk for a PUFA-induced mental, behavioral or neurological disorders including loss of cognitive function caused by an n-3 LcPUFA deficiency, it is beneficial to assess an individual's capacity to make LcPUFAs to assess the risk of aberrant LcPUFA levels either as excesses or deficiencies.

The present invention overcomes previous shortcomings in the art by providing methods and compositions for identifying subjects that have or who are at risk of having omega-3 deficiency (O3D) or omega-6 excess (O6E), as well as methods and compositions for treating such subjects for diseases and disorders associated with O3D or O6E.

SUMMARY OF THE INVENTION

The present invention provides a method of identifying a subject as having, or as having an increased likelihood of having, omega-3 deficiency (O3D), comprising: a) obtaining a biological sample comprising nucleic acid from the subject; and b) determining a methylation percentage at a methylation site in the nucleic acid of the biological sample, wherein the methylation site is selected from the group consisting of cg27386326, cg16213375, cg10515671, cg03805684 and cg19610905 on chromosome 11, wherein a methylation percentage at the methylation site at or above a threshold value identifies the subject as having, or as having an increased likelihood of having, O3D.

In addition, the present invention provides a method of identifying a subject as having, or as having an increased likelihood of having, O3D, comprising: a) obtaining a biological sample comprising nucleic acid from the subject; and b) determining a methylation percentage at a methylation site in the nucleic acid of the biological sample, wherein the methylation site is in a chromosome region on chromosome 11 defined by and including base pair position 61,586,461 to base pair position 61,590,300, wherein a methylation percentage at the methylation site at or above a threshold value identifies the subject as having, or as having an increased likelihood of having, O3D. Thus, a methylation site of this invention can be any methylation site present in the nucleotide sequence of SEQ ID NO:2, wherein methylation sites are underlined.

The methods described above can further comprise the step(s) of treating the subject with a long-chain, omega-3 polyunsaturated fatty acid selected from the group consisting of docosahexaenoic acid (DHA), eicosapentaenoic acid (EPA), docosapentaenoic acid (DPA), stearidonic acid (SDA) and any combination thereof, if the subject is identified as having, or as having an increased likelihood of having, O3D.

Also provided herein is a method of identifying a subject as having, or as having an increased likelihood of having, long chain omega-6 polyunsaturated fatty acid excess (O6E), comprising: a) obtaining a biological sample comprising nucleic acid from the subject; and b) determining a methylation percentage at a methylation site in the nucleic acid of the biological sample, wherein the methylation site is selected from the group consisting of cg27386326, cg16213375, cg10515671 and cg19610905 on chromosome 11, wherein a methylation percentage at the methylation site at or below a threshold value identifies the subject as having, or as having an increased likelihood of having, O6E.

Furthermore, the present invention provides a method of identifying a subject as having, or as having an increased likelihood of having, O6E, comprising: a) obtaining a biological sample comprising nucleic acid from the subject; and b) determining a methylation percentage at a methylation site in the nucleic acid of the biological sample, wherein the methylation site is in a chromosome region on chromosome 11 defined by and including base pair position 61,586,461 to base pair position 61,590,300, wherein a methylation percentage at the methylation site at or below a threshold value identifies the subject as having, or as having an increased likelihood of having, O6E. Thus, a methylation site of this invention can be any methylation site present in the nucleotide sequence of SEQ ID NO:2, wherein methylation sites are underlined.

The methods described above can further comprise the step(s) of treating the subject by reducing the consumption of medium-chain (18 carbon) omega-6 polyunsaturated fatty acids by the subject, reducing the consumption of long-chain omega-6 polyunsaturated fatty acids by the subject and/or administering medium-chain omega-3 polyunsaturated fatty acids and/or long-chain omega-3 polyunsaturated fatty acids to the subject, if the subject is identified as having, or as having an increased likelihood of having, O6E.

The present invention additionally provides a kit comprising reagents and instructions for carrying out the method of any preceding claim.

BRIEF DESCRIPTION OF THE DRAWINGS

FIG. 9. The nucleotide sequence (SEQ ID NO:1) comprising the enhancer region within the FADS gene cluster and the causal methylation sites are shown.

DETAILED DESCRIPTION OF THE INVENTION

Figure 1:
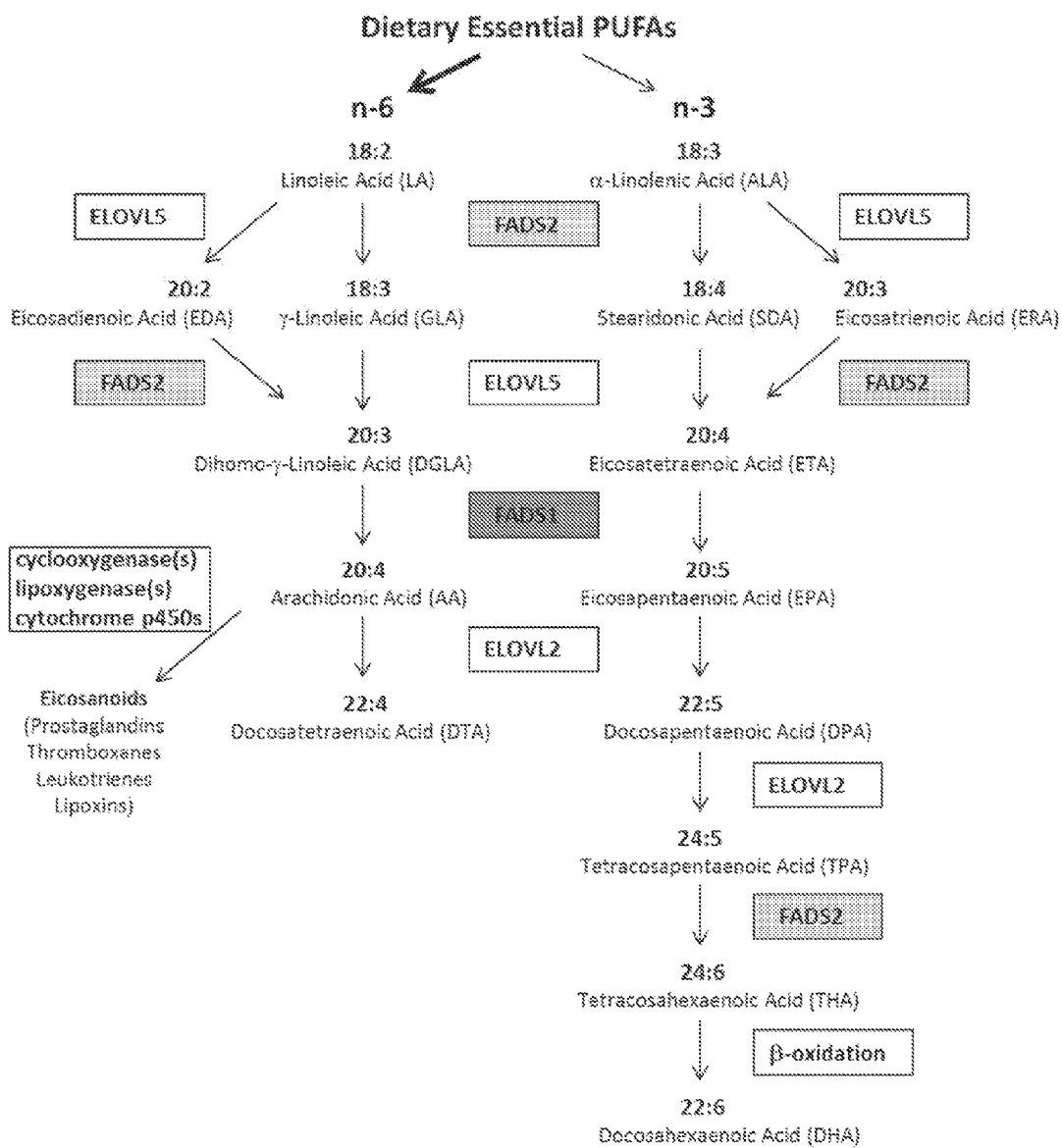
FIG. 1. LcPUFA biosynthesis from dietary essential PUFAs.

Fatty acid desaturation (FADS) enzymatic processes are the rate limiting steps in the biosynthesis of omega-3 (n-3) and omega-6 (n-6) long chain polyunsaturated fatty acids (LcPUFAs). While many SNPs (both within and outside the FADS cluster) have been identified that are associated with the capacity of humans to synthesize LcPUFAs, none of these SNPs themselves have been shown to be the actual cause of changes in FADS gene expression or enzymatic efficiency; they are simply in linkage disequilibrium with unknown causal genetic variant(s) that directly regulate FADS gene expression or some other molecular event that leads to dramatic differences in an individual capacity to synthesize n-3 and n-6 LcPUFAs. Perhaps this is best illustrated by the fact that the SNP rs174537, which has been shown to be most highly associated with FADS1 expression and LcPUFA levels sits well outside the FADS cluster, upstream from FADS1.

Methylation of CpG sites has been shown to occur in transcriptional start sites (typically in CpG islands), in gene bodies, in regulatory elements and in repeat sequences. Until very recently, the vast majority of work has focused on DNA methylation in or around transcriptional start sites in promoters. According to the accepted paradigm, methylation in the immediate vicinity of transcriptional start sites blocks initiation; however, it has been shown that methylation in gene bodies may have a variety of effects from blocking to even stimulating transcription and impacting gene splicing.

The present invention is based on an unexpected discovery that was made after a survey of 485,577 CpG methylation sites throughout the human genome on FADS1 and FADS2 activity. This survey revealed there was a very small methylated DNA region (containing 5 methylation sites) in a regulatory enhancer region that lies between the two proximal promoters of the desaturase genes (FADS1 and FADS2) that regulates LcPUFA biosynthesis. Surprisingly, the methylation status of these five CpG sites was highly related to the enzymatic efficiency of FADS1 and FADS2 and thus the LcPUFA biosynthetic pathway in humans. Specifically, the degree of methylation of this region is inversely related to the enzymatic activities of FADS1 and FADS2, and thus the capacity in humans to synthesize n-3 and n-6 LcPUFAs. Thus, the epigenetic informational content (i.e., the methylation of five sites in a very specific region of the human genome) determines the degree to which the FADS genes are regulated and thus LcPUFA biosynthetic capacity.

In accordance with the present invention we have identified methylation at a small regulatory region within the human genome that regulates the activity of both FADS1 and FADS2 activities and thus the capacity to synthesize LcPUFAs. Thus, a method for assessing a subject's innate capacity of tissues within individuals to synthesize long chain polyunsaturated fatty acids (LcPUFAs) based on this discovery is provided. An exemplary method comprises obtaining from the subject a biological sample that contains genomic nucleic acid having at least one methylation site associated with increased or decreased capacity to synthesize LcPUFAs and determining the methylation status of the at least one methylation site, wherein the methylation status at the site is correlated with fatty acid desaturase efficiencies within cells and tissues and levels of circulating and tissue LcPUFAs and further, wherein the site is selected from the group consisting of a cytosine at position 4490 in SEQ ID NO: 1, a cytosine at position 1237 in the nucleotide sequence of SEQ ID NO: 1, a cytosine complementary to a guanine at position 2410 in the nucleotide sequence of SEQ ID NO: 1, and a cytosine complementary to a guanine at position 12844 in the nucleotide sequence of SEQ ID NO: 1. In one embodiment, the site is a cytosine at position 4490 in the nucleotide sequence of SEQ ID NO: 1, which is located approximately 3.5 kb from the FADS1 transcription initiation site in genomic DNA.

In a particular embodiment, the present invention provides a method of identifying a subject as having, or as having an increased likelihood of having, omega-3 deficiency (O3D), comprising: a) obtaining a biological sample comprising nucleic acid from the subject; and b) determining a methylation percentage at a methylation site in the nucleic acid of the biological sample, wherein the methylation site is selected from the group consisting of cg27386326, cg16213375, cg10515671, cg03805684 and cg19610905 on chromosome 11, wherein a methylation percentage at the methylation site at or above a threshold value (e.g., approximately the $85^{th}$ percentile) for a particular cell type or tissue identifies the subject as having, or as having an increased likelihood of having, O3D.

Also provided herein is a method of identifying a subject as having, or as having an increased likelihood of having, O3D, comprising: a) obtaining a biological sample comprising nucleic acid from the subject; and b) determining a methylation percentage at a methylation site in the nucleic acid of the biological sample, wherein the methylation site is in a chromosome region on chromosome 11 defined by and including base pair position 61,586,461 to base pair position 61,590,300 (SEQ ID NO:2), wherein a methylation percentage at the methylation site at or above a threshold value identifies the subject as having, or as having an increased likelihood of having, O3D. Thus, a methylation site of this invention can be any methylation site present in the nucleotide sequence of SEQ ID NO:2, wherein methylation sites are underlined.

In the methods directed to O3D, in some embodiments, the biological sample is whole blood, the methylation site is cg27386326 and the threshold value is at or above the $85^{th}$ percentile for the samples that have been tested. For whole blood, the $85^{th}$ percentile is about 84% (e.g., 75%, 76%, 77%, 78%, 79%, 80%, 81%, 82% 83%, 84%, 85%, 86%, 87%, 88%, 89%, 90%). In some embodiments, the biological sample is liver tissue, the methylation site is cg27386326 and the $85^{th}$ percentile threshold value is at or above about 66% (e.g., 60%, 61%, 62%, 63%, 64%, 65%, 66%, 67%, 68%, 69%, 70%, 71%, 72%, 73%, 74%, 75%, 76%, 77%, 78%, 79%, and 80%). In some embodiments, the biological sample is saliva, the methylation site is cg27386326 and the $85^{th}$ percentile threshold value is at or above about 70% (e.g., 55%, 56%, 57%, 58%, 59%, 60%, 61%, 62%, 63%, 64%, 65%, 66%, 67%, 68%, 69%, 70%, 72%, 72%, 73%, 74%, 75%, 76%, 77%, 78%, 79%, 80%). In some embodiments, the biological sample is prostate tissue, the methylation site is cg27386326 and the $85^{th}$ percentile threshold value is at or above about 93% (e.g., 85%, 86%, 87%, 88%, 89%, 90%, 91%, 92%, 93%, 94%, 95%, 96%, 97%, 98%, 99%). In some embodiments, the biological sample is CD4+ T cells, the methylation site is cg27386326 and the threshold value is at or above about 70% (e.g., 65%, 66%, 67%, 68%, 69%, 70%, 71%, 72%, 73%, 74%, 75%). Other sample types could include DNA from tissue (ex. liver, skin, fat, kidney, artery) or cancer (prostate, breast, lung, colon/rectal bladder, pancreas, myeloid, lymphoid, kidney, endometrial, and thyroid) biopsies, plasma/serum and blood cells (eosinophils, neutrophils, basophils, macrophages, erythrocytes and lymphocytes (e.g., CD4+ T cells).

The methods described above that are directed to identifying a subject as having or having an increased likelihood of having, O3D can further comprise the step(s) of treating the subject with a long-chain omega-3 polyunsaturated fatty acid selected from the group consisting of docosahexaenoic acid (DHA), eicosapentaenoic acid (EPA), docosapentaenoic acid (DPA), stearidonic acid (SDA) and any combination thereof, if the subject is identified as having, or as having an increased likelihood of having, O3D. These methods can also comprise the step of not treating the subject as described herein if the subject is not identified as having, or as having an increased likelihood of having, O3D.

In some embodiments, the long-chain omega-3 polyunsaturated fatty acid can be administered as a long chain omega-3 polyunsaturated fatty acid-enriched food, dietary supplement, a medical food, prescription product or any combination thereof.

In some embodiments, the long chain omega-3 polyunsaturated fatty acid-enriched food can be an oily fish, including but not limited to, salmon, mackerel, trout and any combination thereof.

In some embodiments, the dietary supplement can be, but is not limited to, long chain omega-3-enriched triglycerides, phospholipids, Krill oil, esters, ethyl esters and any combination thereof.

In some embodiments, the medical food and/or prescription product can be a triglyceride, phospholipid or ester version of a long chain omega-3 polyunsaturated fatty acid that contains a higher dose and/or concentration of omega-3 polyunsaturated fatty acid than dietary supplements, such as Epanova, Lovaza, Vascepa, or any combination thereof.

A subject of this invention can be any animal that produces omega-3 LcPUFAs and omega-6 LcPUFAs. In some embodiments, the subject can be a pregnant and/or lactating female. In some embodiments, the subject can be a newborn, infant, child adolescent, teenager or adult that has, or is suspected of having, a diminished intelligence quotient (IQ), a developmental disorder, autism, attention deficit hyperactivity disorder (ADHD), attention deficit disorder (ADD), schizophrenia, depression, bipolar disorder, panic disorders, or any combination thereof as a result of, or associated with, O3D. In some embodiments, the subject can be a child, adolescent, teenager, or adult that has, or is suspected of having depression, bipolar disorder, schizophrenia, panic disorders, obsessive compulsive disorders (OCD), dementia, Alzheimer's disease, post traumatic stress disorder (PTSD) or any combination thereof as a result of, or associated with, O3D.

Further aspects of the present invention provide a method of identifying a subject as having, or as having an increased likelihood of having, long chain omega-6 polyunsaturated fatty acid excess (O6E) impacting inflammatory disorders including cancer, comprising: a) obtaining a biological sample comprising nucleic acid from the subject; and b) determining a methylation percentage at a methylation site in the nucleic acid of the biological sample, wherein the methylation site is selected from the group consisting of cg27386326, cg16213375, cg10515671, cg03805684 and cg19610905 on chromosome 11, wherein a methylation percentage at the methylation site at or below a threshold value (e.g., approximately the $15^{th}$ percentile) identifies the subject as having, or as having an increased likelihood of having, O6E.

The present invention further provides a method of identifying a subject as having, or as having an increased likelihood of having, O6E, comprising: a) obtaining a biological sample comprising nucleic acid from the subject; and b) determining a methylation percentage at a methylation site in the nucleic acid of the biological sample, wherein the methylation site is in a chromosome region on chromosome 11 defined by and including base pair position 61,586,461 to base pair position 61,590,300 (SEQ ID NO:2), wherein a methylation percentage at the methylation site at or below a threshold value identifies the subject as having, or as having an increased likelihood of having, O6E.

In the methods above directed to O6E, in some embodiments the biological sample is whole blood, the methylation site is cg27386326 and the threshold value is at or below the 15th percentile for the samples that have been tested. For whole blood, the 15th percentile is about 75% (e.g., 70%, 71%, 72%, 73%, 74%, 75%, 76%, 77%, 78%, 79%, 80%). In some embodiments, the biological sample is liver tissue, the methylation site is cg27386326 and the $15^{th}$ percentile threshold value is at or below about 40% (e.g. 35%, 36%, 37%, 38%, 39%, 40%, 41%, 42%, 43%, 44%, 45%). In some embodiments, the biological sample is saliva, the methylation site is cg27386326 and the $15^{th}$ percentile threshold value is at or below about 40% (e.g., 35%, 36%, 37%, 38%, 39%, 40%, 41%, 42%, 43%, 44%, 45%). In some embodiments, the biological sample is prostate tissue, the methylation site is cg27386326 and the $15^{th}$ percentile threshold value is at or below about 81% (e.g., 77%, 78%, 79%, 80%, 81%, 82%, 83%, 84%, 85%, 86%, 87%). In some embodiments, the biological sample is CD4+ T cells, the methylation site is cg27386326 and the threshold value is at or below about 50% (e.g., 45%, 46%, 47%, 48%, 49%, 50%, 51%, 52%, 53%, 54%, 55%).

The methods described herein, for identifying a subject as having, or as having an increased likelihood of having, O6E can further comprise the step(s) of treating the subject by reducing the consumption of medium-chain (18 carbon) omega-6 polyunsaturated fatty acids by the subject, reducing the consumption of long-chain omega-6 polyunsaturated fatty acids by the subject and/or administering medium-chain omega-3 polyunsaturated fatty acids and/or long-chain omega-3 polyunsaturated fatty acids to the subject, if the subject is identified as having, or as having an increased likelihood of having, O6E. These methods can further comprise the step of not treating the subject as described herein if the subject is not identified as having, or as having an increased likelihood of having, O6E.

In some embodiments, the medium-chain omega-3 polyunsaturated fatty acids and/or the long-chain omega-3 polyunsaturated fatty acids can be administered as a dietary supplement, a medical food, a prescription product, or any combination thereof.

In some embodiments, the medium-chain omega-3 polyunsaturated fatty acids are administered in a food, dietary supplement, medical food and/or prescription product, in any combination, enriched in 18 carbon omega-3 polyunsaturated fatty acids.

In some embodiments, the medium (18 carbon) omega-3 polyunsaturated fatty acids can be alpha-linolenic acids (ALA), stearidonic acids (SDA) and any combination thereof. In some embodiments, the 18 carbon omega-3 poly unsaturated fatty acids can be administered as flax seed, SDA enriched vegetable oil, and any combination thereof.

In some embodiments, the long-chain omega-3 polyunsaturated fatty acid can be docosahexaenoic acid (DHA), eicosapentaenoic acid (EPA), docosapentaenoic acid (DPA) and any combination thereof.

In some embodiments, the long chain omega-3 polyunsaturated fatty acid can be administered in a long chain omega-3 polyunsaturated fatty acid-enriched food, which can be, for example, an oily fish, salmon, mackerel, trout and any combination thereof.

In some embodiments, the dietary supplement can comprise, long chain omega-3-enriched triglycerides, phospholipids, Krill oil, esters, ethyl esters and any combination thereof.

In some embodiments, the medical food and/or prescription product can be a triglyceride, phospholipid or ester version of a long chain omega-3 polyunsaturated fatty acid that contains a higher dose and/or concentration of omega-3 polyunsaturated fatty acid than dietary supplements, such as Epanova, Lovaza, Vascepa, or any combination thereof.

In the methods described herein, the subject can have, or be suspected of having a disease caused by inflammation or an inflammatory response including cancer as a result of, or associated with, O6E. As non-limiting examples, the subject may have, or may be suspected of having cardiovascular disease, cerebrovascular disease, atherosclerosis, diabetes, metabolic syndrome, cancer, arthritis, allergies, asthma, allergic rhinitis, inflammatory bowel disease, atopic dermatitis, psoriasis, an inflammatory brain disorder, Alzheimer's disease, multiple sclerosis and encephalitis, celiac disease, myopathy, autoimmune disease, systemic lupus erythematosus (SLE), or any combination thereof.

As set forth herein, dramatic differences have been demonstrated in the capacity of individuals within different populations to produce n-3 and n-6 LcPUFAs. We have further demonstrated that genetic determinants (methylation %) in the FADS cluster play a key role in determining LcPUFA levels. Consequently, O3D and O6E arise from gene-diet interactions as described herein. In addition to blood and tissue levels of LcPUFAs, it has been demonstrated that there are marked differences in the impact of n-3 LcPUFA supplementation on blood and tissue levels of LcPUFAs and the capacity to alter ratios of n-3 to n-6 LcPUFAs in blood and tissues in different individuals.

Thus, large diverse clinical trials will have sizeable subsets of individuals with high, intermediate, and low blood levels of LcPUFAs due to the genetic variation as described herein. Therefore, clinical trials with botanical or marine oils containing n-3 PUFAs have had mixed results because not everyone needs them. Providing individuals with n-3 PUFA supplements who do not have n-3 LcPUFA deficiencies is unlikely to provide any results because the supplementation is not correcting a deficiency. Consequently, the methods of this invention will provide a means of identifying those individuals with O3D or O6E who have gene diet interactions that are causing or contributing to their disease. Future clinical trials with fatty acid-based dietary interventions including providing PUFA-enriched dietary supplements, medical foods and prescription products could be designed with specific methylation % criteria cutoffs to capture only those individuals in need of these fatty acids to correct an omega-3 deficiency or balance an omega-6 excess. It is anticipated that this test will facilitate treating only those who need treating and would markedly enhance the likelihood of efficacious trials.

Thus present invention also comprises embodiments in which the methods of the present invention can be used to diagnose a disease, disorder or condition and/or rule out the presence of a disease, disorder or condition resulting from or associated with O3D or O6E. The methods provided herein can also be used for predicting the potential risk of eventually developing a disease or disorder or condition of this invention and/or for determining a likely course or outcome of a disease, disorder or condition of this invention. Additional embodiments of this invention include using the methods of this invention to choose the most effective and appropriate treatment(s) and/or intervention(s), as well as guiding disease management and monitoring response to treatment throughout care. It is further contemplated that the methods of this invention can be used to assess eligibility for inclusion in or exclusion from a clinical trial.

In some embodiments, the present invention provides a method of guiding a human subject's treatment of an omega-3 deficiency (O3D), comprising: a) obtaining a first biological sample comprising nucleic acid from the subject; b) determining a methylation percentage at a methylation site in the nucleic acid of the first biological sample, wherein the methylation site is selected from the group consisting of cg27386326, cg16213375, cg10515671, cg03805684 and cg19610905 on chromosome 11 (e.g., to identify the subject as a subject in need of treatment for O3D); c) treating the subject for O3D; d) obtaining a second biological sample comprising nucleic acid from the subject at a time point during or after step (c), wherein the second biological sample is of the same tissue type as the first biological sample; e) determining a methylation percentage at the methylation site in the nucleic acid of the second biological sample; and f) guiding the subject's treatment of the O3D, using the methylation percentage values as determined in steps (b) and (e), such that a decrease in the methylation percentage as determined in step (e) relative to the methylation percentage as determined in step (b) leads to no change or a subsequent reduction of the treatment for O3D, and an increase or no change in the methylation percentage as determined in step (e) relative to the methylation percentage as determined in step (b) leads to a subsequent increase or enhancement of the treatment for O3D.

In some embodiments, the present invention provides a method of guiding a human subject's treatment of an omega-3 deficiency (O3D), comprising: a) obtaining a first biological sample comprising nucleic acid from the subject; b) determining a methylation percentage at a methylation site in the nucleic acid of the first biological sample, wherein the methylation site is selected from the group consisting of cg27386326, cg16213375, cg10515671, cg03805684 and cg19610905 on chromosome 11; c) obtaining a first fasting biological sample (e.g., blood) from the subject; d) determining the amount of circulating (e.g., plasma/serum) and cellular (e.g., red blood cell) ALA, DHA, EPA and DPA and/or a ratio of DHA+EPA+DPA/ALA in the first fasting biological sample; e) treating the subject for O3D; f) obtaining a second fasting biological sample from the subject at a time point during or after step (e), wherein the second fasting biological sample is of the same type as the first fasting biological sample; g) determining the amount of circulating and cellular ALA, DHA, EPA and DPA and/or a ratio of DHA+EPA+DPA/ALA in the second fasting biological sample; and h) guiding the subject's treatment of the O3D, using the amount of ALA, DHA, EPA and DPA and/or the ratio of DHA+EPA+DPA/ALA as determined in steps (b) and (g), such that an increase in the amount of DHA, EPA and DPA and/or in the ratio of DHA+EPA+DPA/ALA as determined in step (g) relative to the amount of DHA, EPA and DPA and/or of the ratio of DHA+EPA+DPA/ALA as determined in step (b) leads to no change or a subsequent reduction of the treatment for O3D, and a decrease or no change in the amount of DHA, EPA and DPA and/or in the ratio of DHA+EPA+DPA/ALA as determined in step (g) relative to the amount of DHA, EPA and DPA and/or of the ratio of DHA+EPA+DPA/ALA as determined in step (b) leads to a subsequent increase or enhancement of the treatment for O3D.

Additionally provided herein is a method of guiding a human subject's treatment of an omega-3 deficiency (O3D), comprising: a) obtaining a first biological sample (e.g., blood) from the subject when the subject is in a fasting state; b) determining the amount of circulating (e.g., plasma/serum) and cellular (e.g., red blood cell) ALA, DHA, EPA and DPA and/or a ratio of DHA+EPA+DPA/ALA in the first fasting biological sample; c) treating the subject for O3D; d) obtaining a second biological sample from the subject when the subject is in a fasting state, at a time point during or after step (c), wherein the second biological sample is of the same type as the first biological sample; c) determining the amount of circulating and cellular ALA, DHA, EPA and DPA and/or a ratio of DHA+EPA+DPA/ALA in the second biological sample; and f) guiding the subject's treatment of the O3D, using the amount of ALA, DHA, EPA and DPA and/or the ratio of DHA+EPA+DPA/ALA as determined in steps (b) and (e), such that an increase in the amount of DHA, EPA and DPA and/or in the ratio of DHA+EPA+DPA/ALA as determined in step (e) relative to the amount of DHA, EPA and DPA and/or of the ratio of DHA+EPA+DPA/ALA as determined in step (b) leads to no change or a subsequent reduction of the treatment for O3D, and a decrease or no change in the amount of DHA, EPA and DPA and/or in the ratio of DHA+EPA+DPA/ALA as determined in step (e) relative to the amount of DHA, EPA and DPA and/or of the ratio of DHA+EPA+DPA/ALA as determined in step (b) leads to a subsequent increase or enhancement of the treatment for O3D.

The present invention further provides a method of guiding a human subject's treatment of an omega-6 excess (O6E), comprising: a) obtaining a first biological sample comprising nucleic acid from the subject; b) determining a methylation percentage at a methylation site in the nucleic acid of the first biological sample, wherein the methylation site is selected from the group consisting of cg27386326, cg16213375, cg10515671, cg03805684 and cg19610905 on chromosome 11; c) treating the subject for O6E; d) obtaining a second biological sample comprising nucleic acid from the subject at a time point during or after step (c), wherein the second biological sample is of the same tissue type as the first biological sample; e) determining a methylation percentage at the methylation site in the nucleic acid of the second biological sample; and f) guiding the subject's treatment of the O6E, using the methylation percentage values as determined in steps (b) and (e), such that an increase in the methylation percentage as determined in step (e) relative to the methylation percentage as determined in step (b) leads to no change or a subsequent reduction of the treatment for O6E, and a decrease or no change in the methylation percentage as determined in step (e) relative to the methylation percentage as determined in step (b) leads to a subsequent increase or enhancement of the treatment for O6E.

In additional embodiments, the present invention provides a method of guiding a human subject's treatment of an omega-6 excess (O6E), comprising: a) obtaining a first biological sample (e.g., plasma/serum, blood cells (e.g., red blood cells) from the subject when the subject is in a fasting state; b) determining the amount of arachidonic acid (ARA) and its elongation product, adrenic acid and/or the ratio of ARA+adrenic acid/linoleic acid in the first biological sample; c) treating the subject for O6E; d) obtaining a second biological sample from the subject when the subject is in a fasting state, at a time point during or after step (c), wherein the second biological sample is of the same type as the first biological sample; e) determining the amount of arachidonic acid (ARA) and its elongation product, adrenic acid and/or the ratio of ARA+adrenic acid/linoleic acid in the second biological sample; f) guiding the subject's treatment of the O6E, using the amount of arachidonic acid and adrenic acid and/or the ratio of ARA+adrenic acid/linoleic acid as determined in steps (b) and (e), such that a decrease in the amount of arachidonic acid and adrenic acid and/or in the ratio of AHA+adrenic/linoleic acid as determined in step (e) relative to the amount of arachidonic acid and adrenic acid and/or the ratio or ARA+adrenic acid/linoleic acid as determined in step (b) leads to no change or a subsequent reduction of the treatment for O6E, and an increase or no change in the amount of arachidonic acid and adrenic acid and/or in the ratio of ARA+adrenic acid/linoleic acid as determined in step (e) relative to the amount of arachidonic acid and adrenic acid and/or the ratio of ARA+adrenic acid/linoleic acid as determined in step (b) leads to a subsequent increase or enhancement of the treatment for O6E.

The present invention also provides a method of guiding a human subject's treatment of an omega-6 excess (O6E), comprising: a) obtaining a first biological sample (e.g., blood) from the subject when the subject is in a fasting state; b) determining the amount of circulating (e.g., plasma/serum) and cellular (e.g., red blood cell) linoleic acid (LA), ARA and adrenic acid and/or a ratio of ARA+adrenic acid/LA in the first biological sample; c) treating the subject for O6E, d) obtaining a second biological sample from the subject when the subject is in a fasting state, at a time point during or after step (c), wherein the second biological sample is of the same type as the first biological sample; e) determining the amount of circulating and cellular LA, ARA and adrenic acid and/or a ratio of ARA+adrenic acid/LA in the second biological sample; and f) guiding the subject's treatment of the O6E, using the amount of linoleic acid (LA), ARA and adrenic acid and/or a ratio of ARA+adrenic acid/LA as determined in steps (b) and (e), such that an increase in the amount of ARA and adrenic acid and/or in the ratio of ARA+adrenic acid/LA as determined in step (e) relative to the amount of ARA and adrenic acid and/or in the ratio of ARA+adrenic acid/LA as determined in step (b) leads to no change or a subsequent reduction of the treatment for O6E, and a decrease or no change in the amount of ARA and adrenic acid and/or in the ratio of ARA+adrenic acid/LA as determined in step (e) relative to the amount of ARA and adrenic acid and/or in the ratio of ARA+adrenic acid/LA as determined in step (b) leads to a subsequent increase or enhancement of the treatment for O6E.

In the methods of this invention, the step of determining the methylation percentage can be carried out by a method that can be but is not limited to, methylation specific PCR, whole genome bisulfite sequencing, HELP assay, ChIP on chip assays, methylated DNA immunoprecipitation, pyrosequencing of bisulfite treated DNA, methyl sensitive restriction enzymes, binding of methyl CpG binding proteins and immunocomplex formation between anti-methylated DNA antibodies and said methylated sites, including any combination thereof.

The biological sample containing the nucleic acid to be tested in the methods of this invention can be obtained from any suitable source, for example, a buccal swab, a whole blood sample, a buffy coat sample comprising mononuclear leukocytes (e.g., CD4+ T cells), a urine sample, a biopsy sample, a liver tissue sample, a prostate tissue sample, a serum sample, and/or a saliva sample. Other sample types could include DNA from tissue (ex. liver, skin, fat, kidney, artery) or cancer (prostate, breast, lung, colon/rectal bladder, pancreas, myeloid, lymphoid, kidney, endometrial, and thyroid) biopsies, plasma/serum and blood cells (eosinophils, neutrophils, basophils, macrophages, erythrocytes and lymphocytes).

As noted above, in some embodiments, the invention provides a test and treat method for preventing, modulating and/or ameliorating a disease, disorder or condition associated with aberrant LcPUFA production. Thus, the detection methods described above, in certain embodiments, further entail treating subjects identified as having altered capacity for innate LcPUFA synthesis with an effective treatment, such as an effective amount of a lipid-containing composition. Such compositions can include, but are not limited to, fatty acid-containing dietary supplements, medical foods, functional foods, prescription products and/or pharmaceutical formulations. In some embodiments, the subject can be treated with an agent that modulates methylation of CpG sites.

In one embodiment comprising a subject diagnosed as having, or as having an increased likelihood of having, O3D, the individual is a pregnant and/or nursing female and the treatment increases LcPUFA levels in a fetus and/or breast milk. In another embodiment, the individual is a female who has recently given birth and said treatment increases levels of desirable Lc-PUFAs in breast milk. In yet other embodiments, the individual is at increased risk of having or developing a developmental or neurodegenerative disorder due to having or as having an increased genetic likelihood of O3D. The individual to be tested can also be a pediatric subject or fetus.

In another embodiment, the individual identified as having or as having an increased likelihood genetically of producing excess n-6 LcPUFAs is at increased risk for a cardiovascular disorder and treatment reduces levels of n-6 LcPUFAs.

The present invention further provides a method of measuring the methylation status of tissue in a biopsy (e.g., a tumor biopsy) from a subject that has cancer or is suspected of having cancer. By identifying the methylation status of cells in the biopsy tissue from the subject according to the methods described herein, a determination can be made regarding how much the n-6 PUFA content of the modern western diet (as opposed to other causes) is contributing to/promoting the subject's cancer and which subjects (what subset of cancer patients) would be most improved by altering the subject's diet by reducing n-6s and increasing n-3s as described herein. In further embodiments, even before a subject develops cancer or is suspected of having cancer, a subject's likelihood of developing cancer as a result of omega-6 polyunsaturated fatty acids in the diet could be determined by measuring the methylation status of cells in certain tissue samples (e.g., saliva, blood cells or CD4+ T cells) obtained from the subject according to the method described herein. The subject could then take action and/or be treated to reduce the likelihood of developing cancer by reducing his/her intake of n-6 PUFAs and/or increasing his/her intake of n-3 PUFAs as described herein.

Also encompassed by the invention are kits for practicing the methods described above.

In yet another aspect, the invention provides a screening assay for identifying agents that alter the methylation status of a CpG site in the FADS gene cluster on chromosome 11. An exemplary method comprises providing cells that contain and express the gene cluster, incubating the cells in the presence or absence of a test agent; and determining the methylation status of at least one site selected from: a cytosine at position 4490 in the nucleotide sequence of SEQ ID NO: 1, a cytosine at position 1237 in the nucleotide sequence of SEQ ID NO:1, a cytosine complementary to a guanine at position 2410 in the nucleotide sequence of SEQ ID NO: 1, and a cytosine complementary to a guanine at position 12844 in the nucleotide sequence of SEQ ID NO: 1, in the presence and absence of said agent, wherein methylation status is correlated to fatty acid desaturase levels, and wherein agents that alter the methylation status relative to untreated control cells are identified as effective in modulating fatty acid desaturase levels.

The following definitions are provided to facilitate an understanding of the present invention.

As used herein, "a" or "an" or "the" can mean one or more than one. For example, "a" cell can mean one cell or a plurality of cells.

Also as used herein, "and/or" refers to and encompasses any and/or all possible combinations of one or more of the associated listed items, as well as the lack of and and/or combinations when interpreted in the alternative ("or").

Furthermore, the term "about" as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, *In re Herz*, 537 F.2d549, 551-52, 190 U.S.P.Q. 461, 463 (CCPA 1976) (emphasis in the original); see also MPEP §2111.03. Thus, the term "consisting essentially of" when used in a claim of this invention is not intended to be interpreted to be equivalent to "comprising."

As used herein, the term PUFA refers to polyunsaturated fatty acids.

As used herein, the term "risk" refers to an aspect of personal behavior, or lifestyle, an environmental and dietary exposure, or an inborn or inherited characteristic which on the basis of epidemiological evidence is known to be associated with health related condition(s) considered important to ameliorate or prevent.

As used herein, the term "increased risk" or "increased likelihood means a level of risk or likelihood that is increased as a result of having an increased or decreased genetic propensity to produce omega-6 (n-6) or omega-3 (n-3) long chain polyunsaturated fatty acids. In the case of an increased propensity to produce omega-6 long chain polyunsaturated fatty acids such as arachidonic acid (O6E), the risk or likelihood of having an inflammatory disorder, including cancer, is increased. In the case of a reduction in the capacity to produce omega-3 long chain polyunsaturated fatty acids such as docosahexaenoic acid (DHA), this would be an increased risk or likelihood of losing cognitive function and/or of having a mood, neurological and/or developmental disorder as a result of reduced levels of omega-3 long chain polyunsaturated fatty acids (O3D). In some embodiments, the risk or likelihood is increased in a subject as compared to a subject having a normal methylation status at the methylation site cg27386326 as defined herein that is within the range of 15%-85%.

As used herein, the terms DHA, ARA, EPA, DGLA, GLA and ALA refer to the polyunsaturated fatty acids docosahexaenoic acid, arachidonic acid, eicosapentaenoic acid, dihommo gamma-linolenic acid gamma-linolenic acid and alpha-linolenic acid, respectively.

As used herein, the terms FADS1 and FADS2 refer to the fatty acid desaturase genes that encode enzymes known as Δ-5 desaturase and Δ-6 desaturase, respectively.

As used herein, the terms "C" and "G" or "CpG" refer to cytosine and guanine, respectively. The term "p" refers to the phosphodiester bond between the cytosine and the guanine, which indicates that the C and the G are next to each other in sequence.

Figure 9:
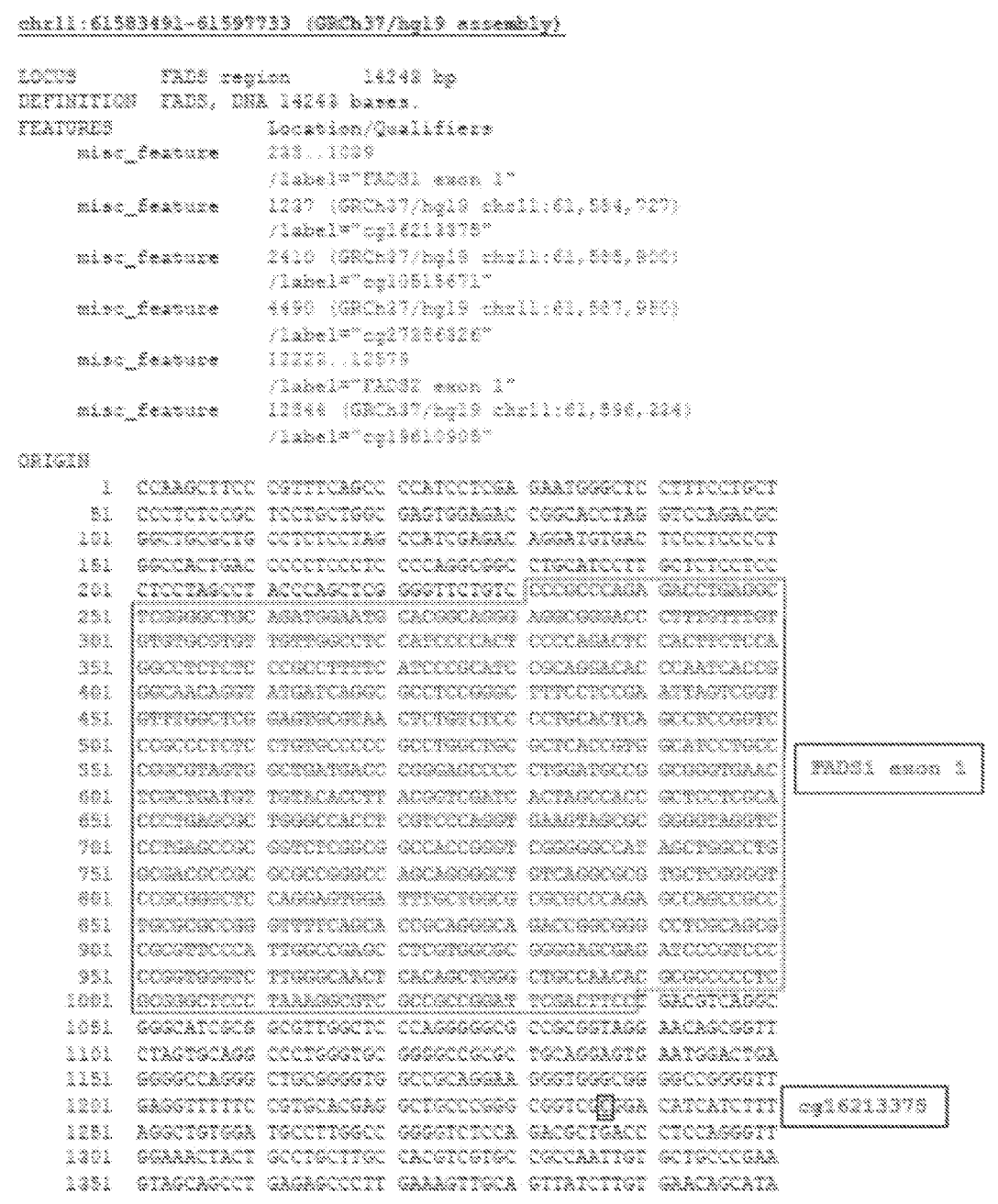
Figure 9:
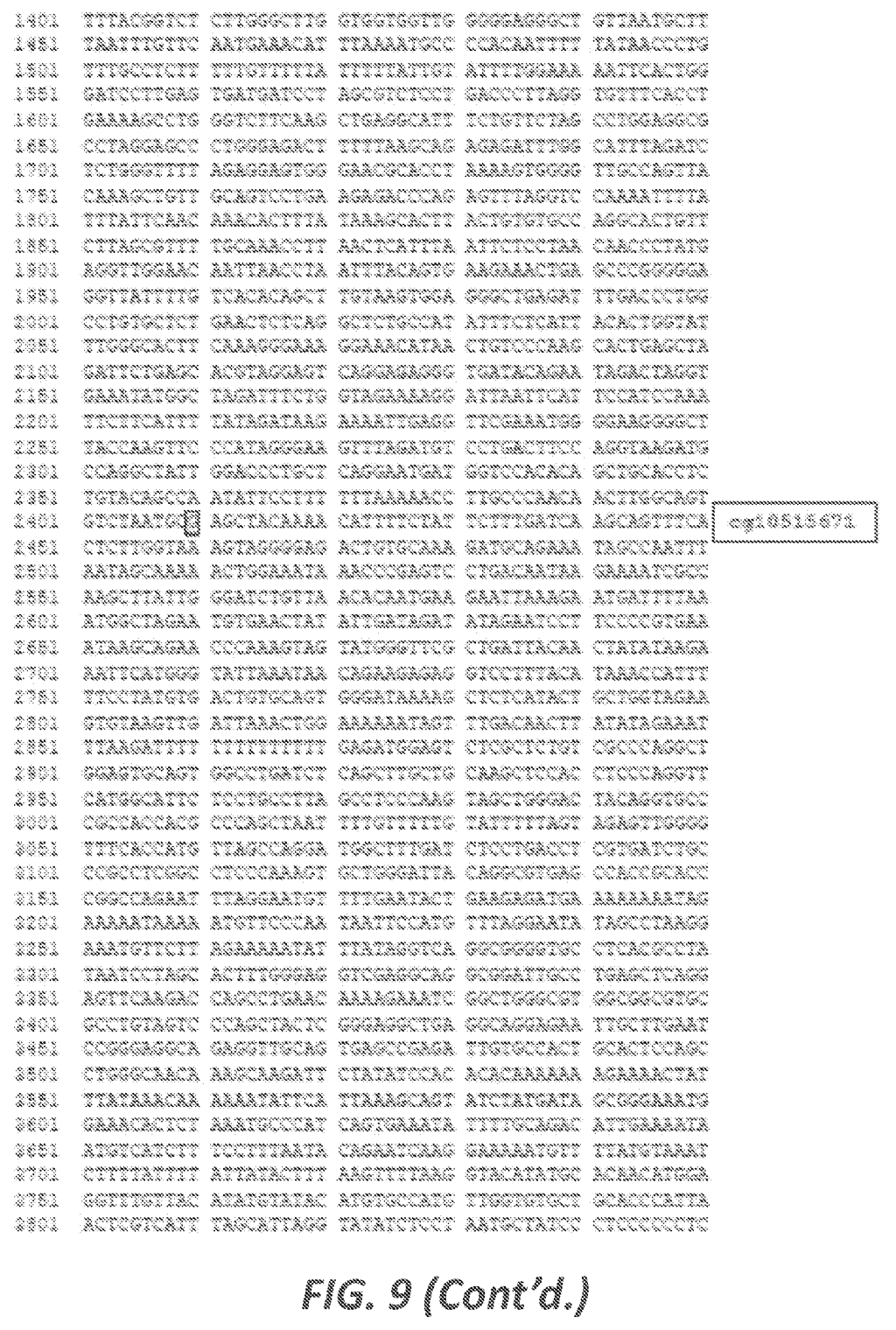
Figure 9:
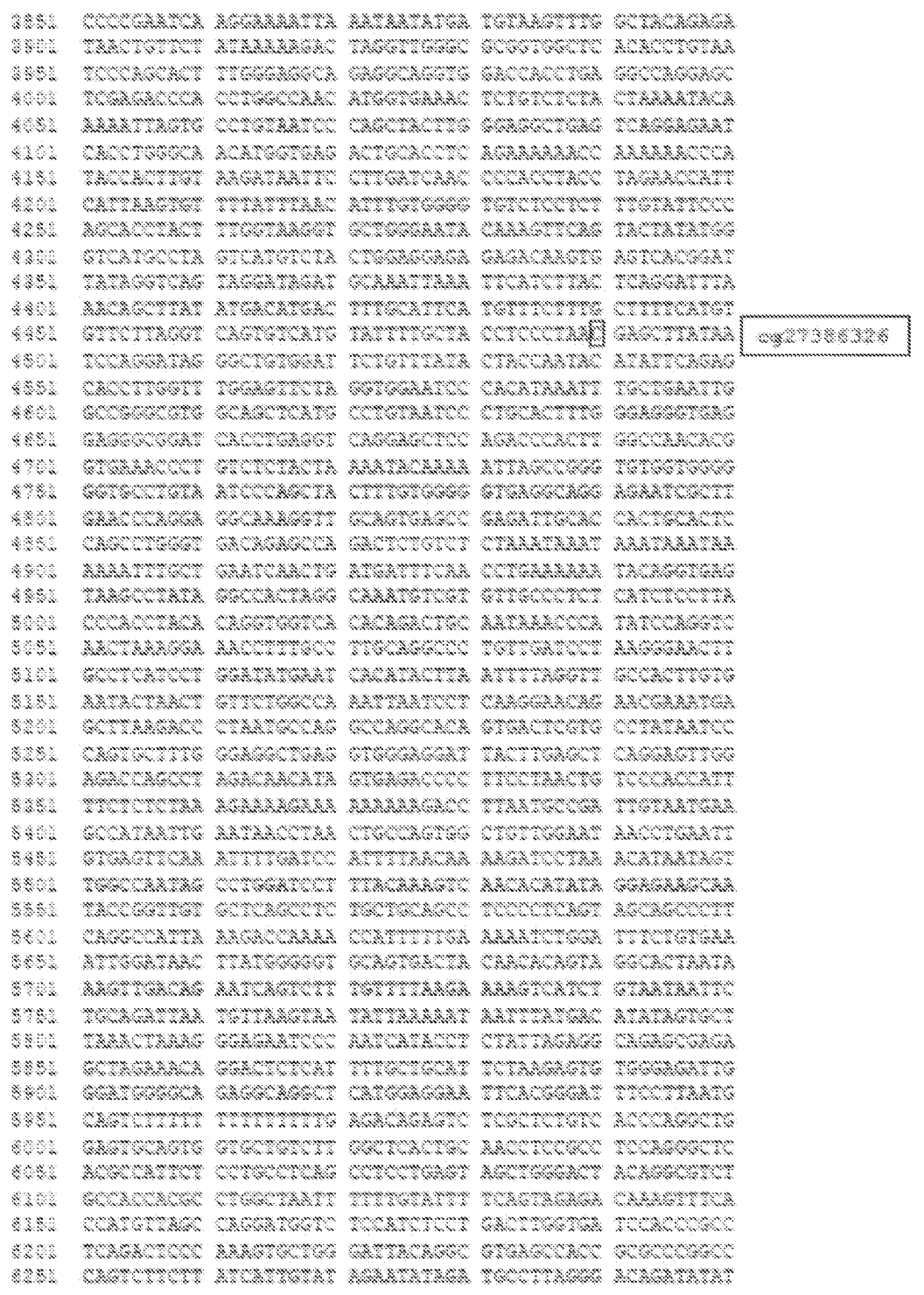
Figure 9:
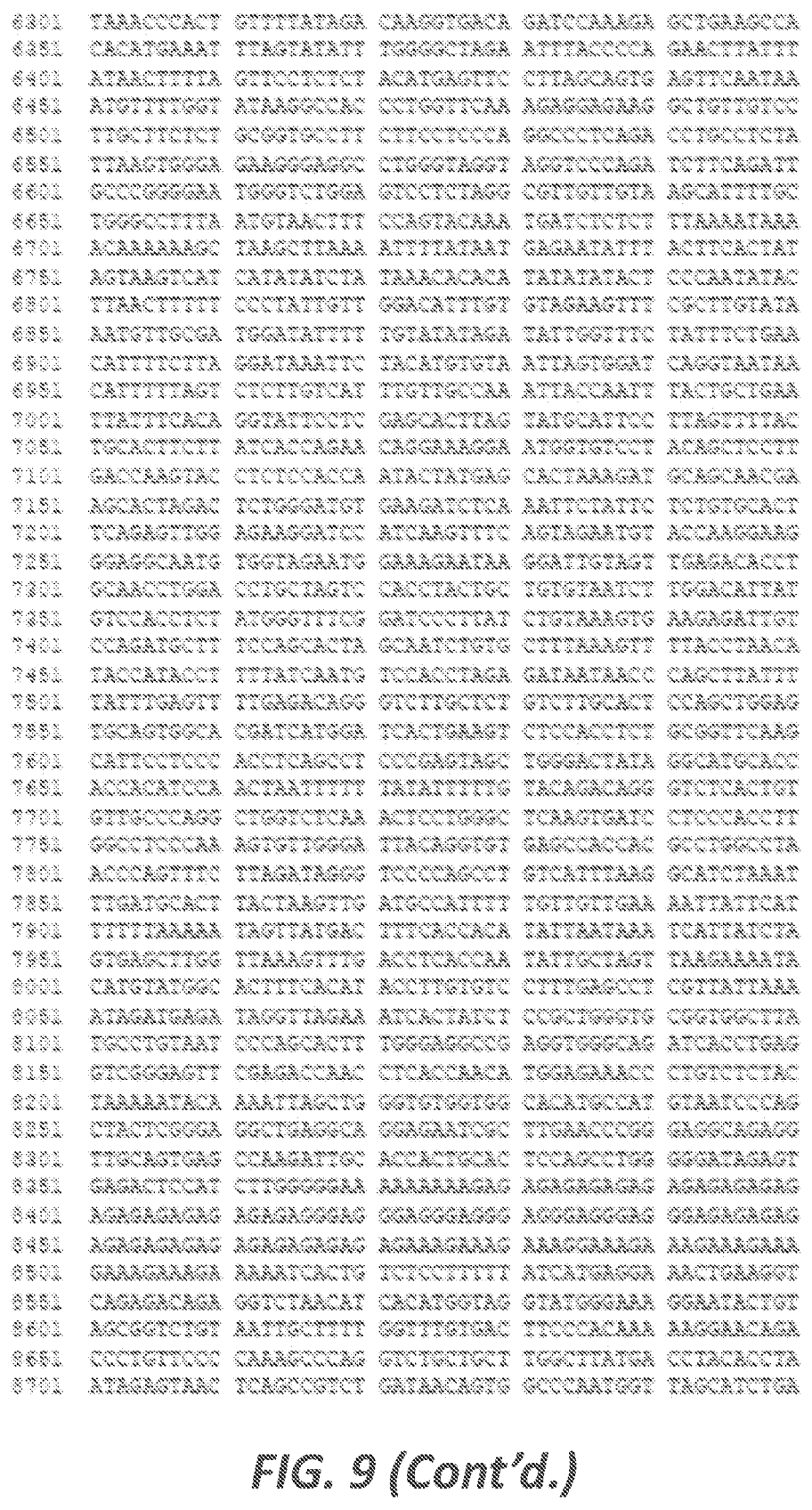

As used herein, the term "methylation site" when used in the context of a CpG, refers to a site where a C is immediately followed by a G. The nucleotide sequence of SEQ ID NO:1, comprising the enhancer region containing 4 of the 5 methylation sites identified herein, is provided in FIG. 9.

As used herein, the term "genomic DNA" refers to DNA found within the 46 chromosomes in humans. The genomic DNA provides a complete set of genetic information including coding and non-coding DNA.

As used herein, the term "sodium bisulfite" refers to sodium hydrogen sulfite having the chemical formula of $NaHSO_3$. Sodium bisulfite functions to deaminate cytosine into uracil; but does not affect 5-methylcytosine (a methylated form of cytosine with a methyl group attached to carbon 5). When the bisulfite-treated DNA is amplified via polymerase chain reaction, the uracil is amplified as thymine and the methylated cytosine is amplified as cytosine.

As used herein, the term "methylation" refers to the addition of a methyl group to the 5' carbon of the cytosine base in a deoxyribonucleic acid sequence of CpG within a gene on a human chromosome.

As used herein, the term "methylation status" refers to the presence or absence or more typically the proportion or percentage of a methylated cytosine base at a methylation site in a CpG within a gene. Methylation of a CpG is often associated with inhibition of gene expression. For purposes of this application, preferred methylated CpGs are located in an enhancer region which regulates FADS1 and FADS2 activity.

As used herein the terms "methylation percentage" or "DNA methylation percentage" or "methylation proportion" refer to the percentage of DNA molecules that are methylated at a given CpG site, relative to the total number of molecules examined at that site, using standard methods.

As used herein, the terms "western diet" or "modern western diet" refer to the typical western diet eaten by a subject in a developed country such as the United States. Such a diet typically contains greater than about 6% of energy (calories) as the omega-6 polyunsaturated fatty acid, linoleic acid and less than about 3% of energy (calories) as omega-3 polyunsaturated fatty acid.

As used herein, the terms "resulting from" or "associated with" when used in reference to diseases, disorders or conditions caused by O3D or O6E, respectively, refer to instances where O3D and O6E is likely to cause or contribute in some way to diseases, disorders or conditions.

As used herein, the term "methylation specific PCR" refers to the use of primer pairs in a PCR reaction that are complementary to DNA that is converted by sodium bisulfite and that contains several CpG dinucleotides (i.e., multiple methylation sites) that can be methylated in vivo. Primers can be complementary to the methylated template where methylated CpG cytosines are not converted to uracil by the sodium bisulfite treatment and non-CpG cytosines are converted to uracil.

As used herein, the term "nested PCR" refers to a variation of the polymerase chain reaction (PCR) in that two pairs of PCR primers are used to amplify a fragment. The first pair of PCR primers amplifies a portion of a gene to form a first amplicon. The second pair of primers is nested within the first amplicon and bind inside the first amplicon to allow amplification of a second amplicon which is shorter than the first amplicon.

As used herein, the term "real time PCR" (also called quantitative polymerase chain reaction or qPCR) refers to a method for the detection and quantitation of an amplified PCR product based on incorporation of a fluorescent reporter dye; the fluorescent signal increases in direct proportion to the amount of PCR product produced and is monitored at each cycle, 'in real time', such that the time point of the first significant increase in the amount of PCR product correlates with the initial amount of target template.

As used herein, the term "primer set" refers to a pair of PCR primers that include a forward primer and reverse primer used in a PCR reaction and allows the generation of an amplicon.

As used herein, the term "probe" includes, for example, a TaqMan probe used in a real time PCR and can comprise or consist of a fluorophore covalently attached to the 5'-end of an oligonucleotide designed such that it anneals within a DNA region amplified by a specific set of primers and a quencher at the 3'-end. The quencher molecule quenches the fluorescence emitted by the fluorophore when excited by a light source via FRET (Fluorescence Resonance Energy Transfer). As the Taq polymerase extends the primer during PCR and synthesizes the nascent strand, the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore.

As used herein, the term "detecting the methylation status of a gene" refers to detecting or assessing the presence or absence of a methylated cytosine base within a gene of interest. Methods of detecting the methylation status of a gene include, for example, nested methylation specific PCR, methylation specific PCR or bisulfite sequencing.

As used herein, the phrase "dietary supplements" encompasses dietary supplements, medical foods, pharmaceutical formulations, functional foods and functional beverages containing effective levels of Lc-PUFAs of interest. In certain embodiments, it is desirable to administer FDA approved pharmaceutical preparations of fatty acids (e.g., Omacor from Reliant Pharmaceuticals) to a subject in need thereof. Preferred lipid-containing dietary supplements and/or pharmaceutical formulations comprise fatty acids (as triglycerides, phospholipids, fatty acid methyl esters, galactolipids) designed to prevent or overcome the PUFA deficiencies or excesses in PUFA biosynthesis identified according to the present invention.

As used herein, the phrase "FADS cluster" refers to the Δ5 (FADS1) and Δ6 (FADS2) desaturases encoded by members of a gene family cluster (FADS1, FADS2 and FADS3) localized to a 100 kb region on chromosome 11 (11q12.2)

In one aspect, the present invention provides a method of detecting DNA methylation (i.e., detecting DNA methylation status) in a sample of genes including those in the FADS cluster on chromosome 11. An increase in DNA methylation of the sites identified in accordance with the present invention is found to be correlated with reduced desaturase activity and a modulation of a subject's innate capacity to synthesize LcPUFAs. The present method comprises a step of obtaining a biological sample collected from a human subject, and isolating DNA from the sample. In one approach, isolation is followed by treating the isolated DNA with a chemical agent (such as sodium bisulfite) to convert unmethylated cytosine to uracil. The DNA methylation at the identified site is detected using a two round PCR protocol. The first round PCR amplifies DNA regions of interest that undergo DNA methylation, and the second round PCR is a nested methylation-specific PCR. The present invention provides a DNA methylation detection assay that offers good sensitivity and specificity. The present DNA methylation assay offers an optimal test to predict an individual's innate capacity for LC-PUFA synthesis based on the levels of methylation at cg27386326, also referred to herein as the cytosine at position 4490 in the nucleotide sequence of SEQ ID NO:1 and the other sites identified herein.

In certain embodiments, where a disorder or altered capacity to synthesize LcPUFAs has been identified, a subject may require or benefit from treatment and follow-up monitoring. Thus the types of assays described above can be performed at scheduled intervals. Additional assays may include assessing circulating PUFA levels.

Methods of Testing

In accordance with the present invention, analysis of CpG DNA methylation sites located on human chromosome 11 has been carried out. The sites were initially identified from the Illumina HumanMethylation450 BeadChip and their designations. The locations of the sites described herein are below.

| Illumina ID | Genomic Location (GRCH37, hg19*) and position in SEQ ID NO: 1 |
|---|---|
| cg03805684 | chr11: 61,561,219 |
| cg16213375 | chr11: 61,584,727 (C at position 1237) |
| cg10515671 | chr11: 61,585,900 (C complementary to G at position 2410) |
| cg27386326 | chr11: 61,587,980 (C at position 4490) |
| cg19610905 | chr11: 61,596,334 (C complementary to G at position 12844) |

*based on human Genome Reference Consortium assembly GRCh37, also referred to as human genome build hg19

For detection of the CpG DNA methylation sites located on human chromosome 11, base pairs 61,587,980 (C) to 61,587,981 (G), several different approaches may be employed. In one aspect, the target C nucleotide is assayed with the Illumina HumanMethylation450 BeadChip microarray, and is referred to as target ID cg27386326 or a cytosine at position 4490 in SEQ ID NO:1. To accurately measure DNA methylation at this location, a quantitative method must be used. Most detection methods currently available rely on initial bisulfite conversion of the DNA, which chemically converts non-methylated cytosine nucleotides (C) to uracil (U). In some assays, the uracil nucleotides are then converted to thymine nucleotides (T). When cytosine nucleotides are methylated (meC), bisulfite treatment has no effect. After bisulfite treatment, DNA methylation assays examine the sequence of CpG sites and quantitatively determine the ratio of U/T (formerly an unmethylated C) to C (formerly methylated C). Therefore after PCR, the resultant product contains cytosine only at the position where 5-methylcytosine occurs in the starting template DNA. This makes the discrimination between unmethylated and methylated cytosine possible. Useful conventional techniques of molecular biology and nucleic acid chemistry for assessing sequence differences are well known in the art. (See, for example, Sambrook et al. *Molecular Cloning: A Laboratory Manual* (2001) 3rd edition, Cold Spring Harbor, N.Y.).

In one embodiment, the present DNA methylation method provides a two round (i.e., two step) PCR reaction for detecting the methylation status of the FADS1, FADS2 and FADS3 genes. The present two-step PCR is an improved methylation assay that provides a much higher sensitivity and specificity for detecting DNA methylation.

In the first round PCR reaction, primer sets (i.e., forward printer and reverse primer) are designed to flank the methylation sites of interest (i.e., potential methylation sites). Preferably, primers are designed to anneal to non-CpG containing regions within the specific CpG site of that particular gene. After the first round PCR, the resulting amplicon contains CpG dinucleotides that are aberrantly methylated. The amplicon generated from the first round PCR reaction thus provides a template for the second round PCR reaction, which then detects the methylation status of the respective genes.

In the second round PCR reaction (i.e., nested methylation specific PCR), the primer sets (i.e., forward primer and reverse primer) are designed to perform as a nested methylation specific PCR reaction. The second PCR amplifies the region within the amplicon (generated from the first round PCR reaction) that contains the methylation sites of interest. Therefore, the second round PCR uses the first round amplicon as a template for the PCR reaction. The second round PCR uses primer sets that are methylation specific primers. The methylation specific primers are designed to hybridize internally within the flanking primers of the first round PCR.

There are several protocols available to the skilled artisan for detection of methylated bases in DNA. These include commercially available kits as well as custom methods. Non-limiting examples of some of the most commonly used methods are described below.

Bisulfite Sequencing

This process involves using standard Sanger DNA sequencing to sequence DNA that has been bisulfite treated. A comparison is made between the bisulfite treated and known sequence to identify methylated sites. This method is considered less quantitative than some of the others, and requires a DNA sequencer, such as the 310, 3500, or 3730×1 DNA Analyzers (Applied Biosystems, Inc.).

Pyrosequencing

Considered the gold standard for DNA methylation quantitation, this method involves sequencing short sequences of DNA around the target methylation site after bisulfite conversion. Pyrosequencing quantitatively measures the addition of each base onto a growing nucleotide chain, and the ratio of C (methylated) to T (unmethylated) at each target site accurately measures DNA methylation. This method requires specific instrumentation, such as the PyroMark Q24 (Qiagen, Inc.).

Epityper

This assay starts with bisulfite-treated DNA and is followed by PCR, in vitro transcription, and base-specific cleavage. The resulting products differ by methylation status and are detected by differences in molecular mass. This method is specific to Sequenom, Inc., and relics on mass spectrometry instrumentation (MALDI-TOF) from the company. This equipment has been used for SNP genotyping and is available in many laboratories that do SNP genotyping.

Whole Genome Bisulfite Sequencing

Also known as BS-Seq, this approach entails a high-throughput genome-wide analysis of DNA methylation. It is based on aforementioned sodium bisulfite conversion of genomic DNA, which is then sequenced on a next-generation sequencing platform. The sequences obtained are then re-aligned to the reference genome to determine methylation states of CpG dinucleotides based on mismatches resulting from the conversion of unmethylated cytosines into uracil.

The HELP Assay

This assay is based on restriction enzymes' differential ability to recognize and cleave methylated and unmethylated CpG DNA sites.

ChIP-On-Chip Assays

These assays are based on the ability of commercially prepared antibodies to bind to DNA methylation-associated proteins like MeCP2.

Methylated DNA Immunoprecipitation (MeDIP)

Analogous to chromatin immunoprecipitation, this assay uses immunoprecipitation to isolate methylated DNA fragments for input into DNA detection methods such as DNA microarrays (MeDIP-chip) or DNA sequencing (MeDIP-seq).

Molecular Break Light Assay for DNA Adenine Methyltransferase Activity

This assay relies on the specificity of the restriction enzyme DpnI for fully methylated (adenine methylation) GATC sites in an oligonucleotide labeled with a fluorophore and quencher. The adenine methyltransferase methylates the oligonucleotide, making it a substrate for DpnI. Cutting of the oligonucleotide by DpnI gives rise to a fluorescence increase.

Methyl Sensitive Southern Blotting

This assay is similar to the HELP assay, although it uses Southern blotting techniques to probe gene-specific differences in methylation using restriction digests. This technique is used to evaluate local methylation near the binding site for the probe.

MethylCpG Binding Proteins (MBPs)

MBPs and fusion proteins containing just the methyl binding domain (MBD) are used to separate native DNA into methylated and unmethylated fractions. The percentage methylation of individual CpG islands can be determined by quantifying the amount of the target in each fraction. Extremely sensitive detection can be achieved in FFPE tissues with Abscription based detection.

In some embodiments, the present invention provides compositions and methods for determining a subject's innate capacity for synthesis of n-6 and n-3 LcPUFAs. The method entails a test and treat paradigm for such subjects in order to identify compromised subjects or those requiring therapeutic intervention. Thus, following determination of the methylation state of the sites identified herein, methods for treating a disease or disorder and/or condition in a subject in need thereof are provided. In some embodiments, the disease, disorder and/or condition that is treated includes, but is not limited to, cardiovascular diseases, inflammatory diseases, and various types of cancer. In other embodiments, the cardiovascular diseases to be treated can include but are not limited to, hypertriglyceridemia, coronary heart disease, stroke, acute myocardial infarction and atherosclerosis. In further embodiments, the inflammatory diseases to be treated can include but are not limited to, asthma, arthritis, allergic rhinitis, psoriasis, atopic dermatitis, inflammatory bowel diseases, Crohn's disease, and allergic rhinoconjunctivitis. In still further embodiments, the cancers to be treated can include but are not limited to, prostate cancer, breast cancer and colon cancer. In additional embodiments, the diseases, disorders and/or conditions to be treated can include psychiatric disorders. Nonlimiting examples of psychiatric disorders of this invention include depression, bipolar disorder and schizophrenia. In addition, the compositions of the invention can be used to maintain and/or enhance cognitive function.

In some embodiments, the subject can be a gravid female, who can be tested before, during, and/or after pregnancy to assess the subject's capacity to produce n-3, 20-22 carbon LcPUFAs to determine whether she provides sufficient n-3 long chain polyunsaturated fatty acids to a fetus in utero and/or to an infant during breast feeding. It is also well recognized that sufficient n-3 and n-6 LcPUFAs and particularly DHA are required for brain development and function of the developing fetus (FIG. 2) (for a review, see Haggarty 2010. *Annu. Rev. Nutri.* 30:237-255). Subjects who lack this capacity can be treated with fatty acid supplementation and/or prescription regimens to promote and/or support healthy brain development and function of a developing fetus and/or infant.

Figure 2:
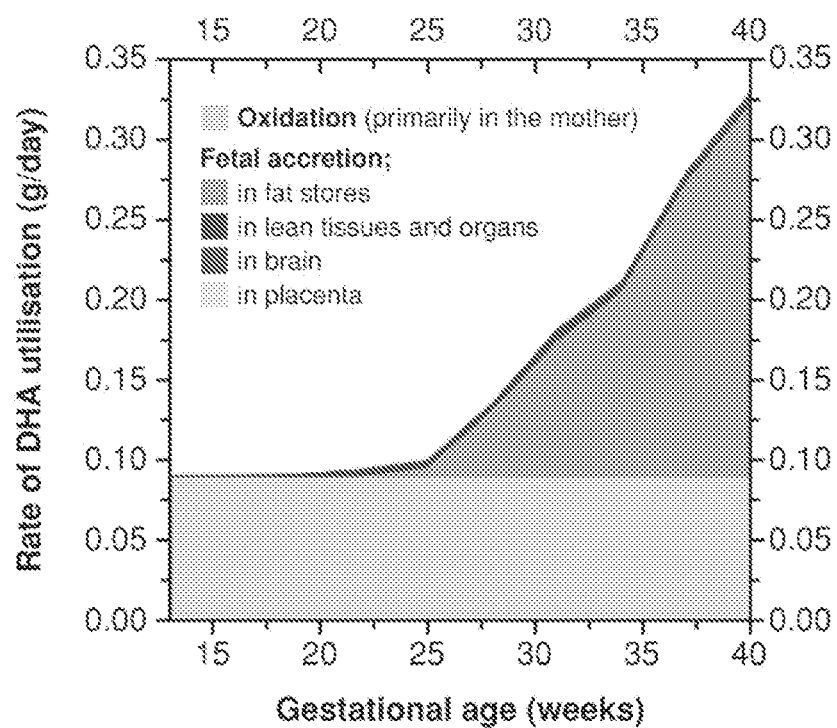
FIG. 2. Change in the rate of docosahexaenoic acid (DHA) utilization with stage of gestation and its relationship to dietary intake of biosynthetic capacity (FADS activity and methylation status). From Haggarty. *Annu Rev Nat* 30:237-255 (2010). The amount of DHA in a tissue such as the brain=1) DHA that is taken in preformed from the diet+2) DHA that is synthesized from omega-3 precursor fatty acids (highly influenced by FADS genetic variation)+3) DHA that is found in tissue reservoirs such as fat (highly dependent on diet and FADS genetic variation)—DHA that is lost due to oxidation taking place in all tissues. If DHA oxidation exceeds the sum of the three sources of DHA accretion, levels of DHA in tissues such as the brain will be reduced. We have termed this omega-3 deficiency (O3D).
Figure 3:
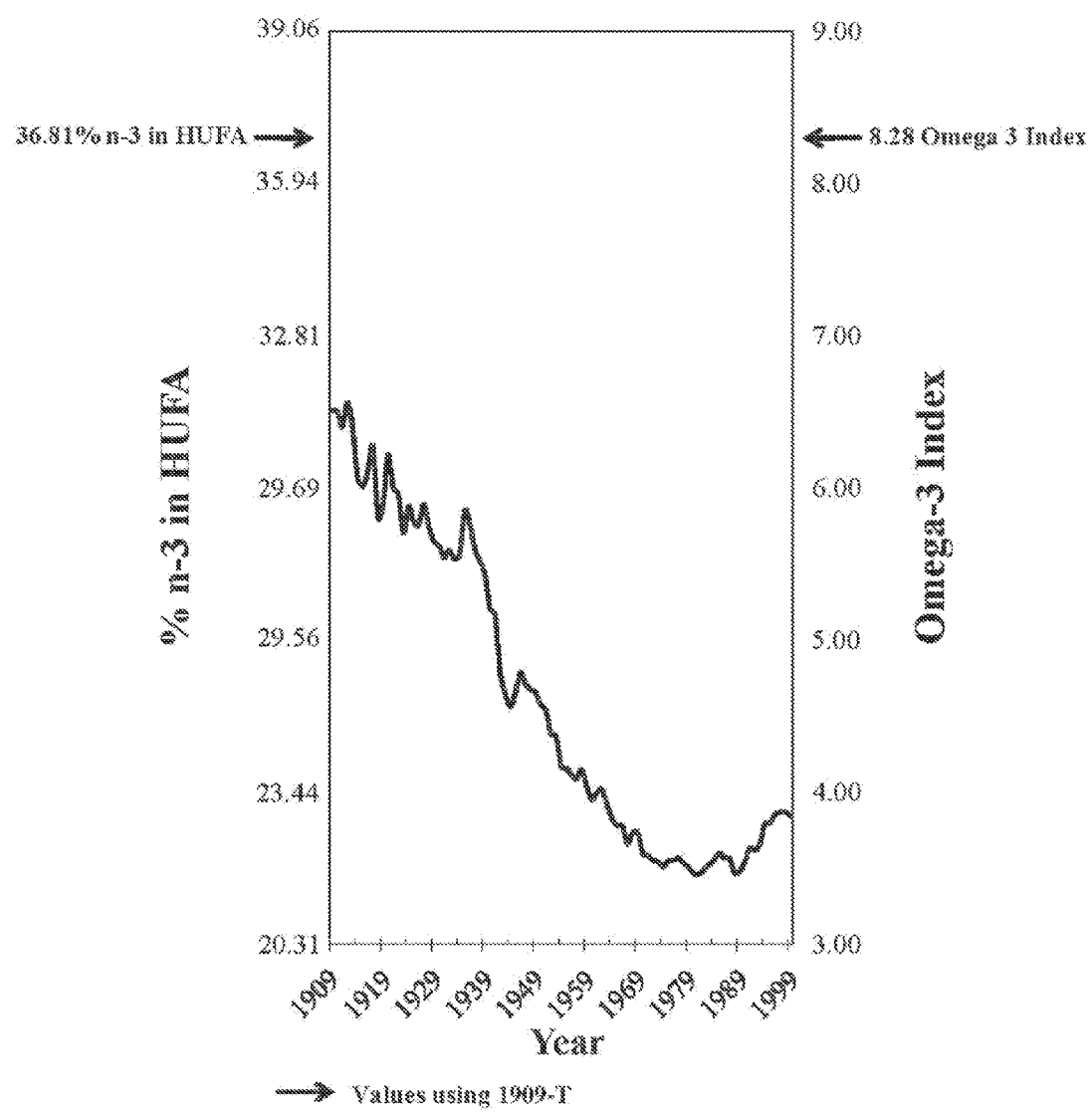
FIG. 3. n-3 LcPUFA levels over the 20th century. Solid arrows indicate the percentage of LcPUFAs (36.8%) and the estimated omega-3 index (circulating n-3 LcPUFAs) calculated from available nutrient intakes for 1909 traditional foods (1909-T). With the western diet, circulating n-3 LcPUFA levels have dropped to below 4% of total circulating fatty acids. From Blasbalg et al. *Am J Clin Nutr* 93:950-962 (2011).
Figure 4:
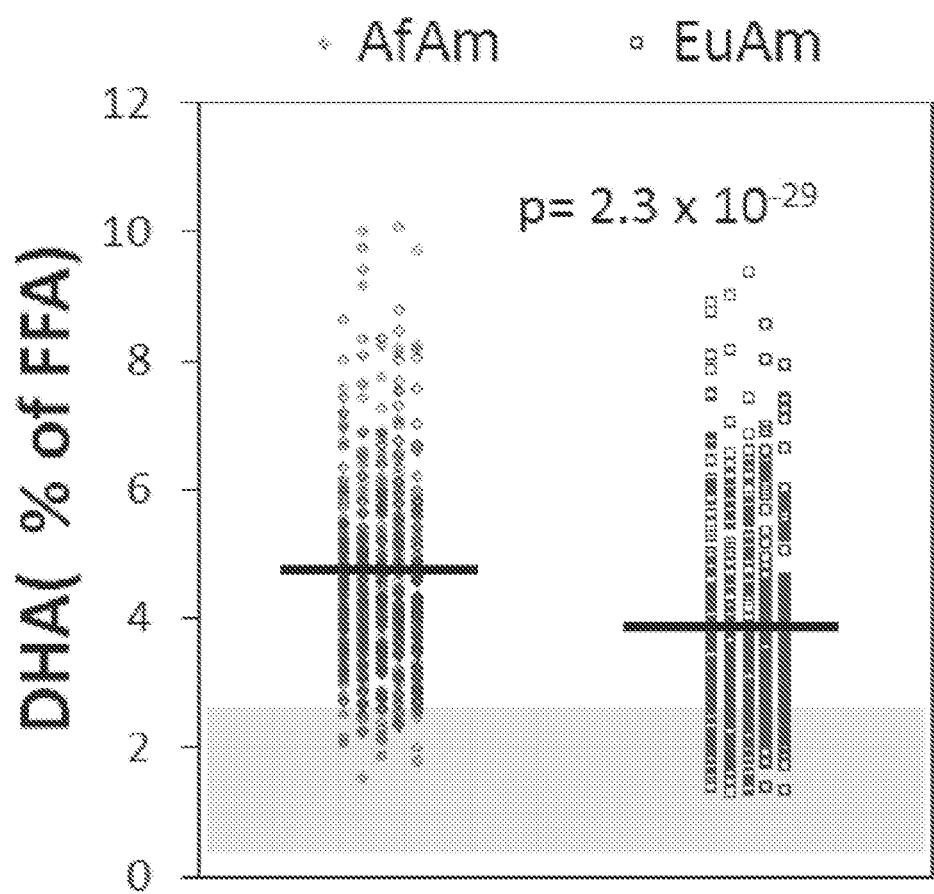
FIG. 4. Circulating DHA levels in African and European Americans. This figure shows the DHA levels in circulating plasma phospholipids from African and European American populations. The gray shaded area indicates those individuals in the populations with low levels of DHA, or O3D. FFA=free fatty acids.

It is also well recognized that sufficient n-3 and n-6 LcPUFAs are required for brain development in young infants and children (FIG. 2). The present invention provides compositions and methods for determining a child's innate capacity to produce LcPUFAs necessary for early childhood development. Children who lack this capacity can be treated with fatty acid supplementation and/or prescription regimens to promote and/or support healthy brain development and function.

Methods of Treatment

A further aspect of the present invention provides administering appropriate PUFAs or agents that modulate PUFA production, to a subject so tested and shown to be deficient or to have excess LcPUFAs for the therapeutic and/or prophylactic treatment of a disease, disorder or condition.

For example, the invention includes methods of determining an increased risk for disease in a subject based on the subject's innate genetic capacity to synthesize LcPUFAs and includes administration of agents effective for preventing and/or treating the disease. Such diseases can include, without limitation, cardiovascular disease, chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculpathy, pulmonary disorder, schizophrenia, depression, weight maintenance, peroxisomal disorder, autoimmune disorder, inflammatory disorder, central nervous system disorder, chronic pain and any combination thereof by providing the fatty acid compositions and/or agents as described herein.

Cardiovascular diseases and disorders that can be treated with the fatty acid formulations and/or agents described herein include, but are not limited to, angina, atherosclerosis, hypercholesterolemia, hypertriglyceridemia, low HDL, high blood pressure, Raynaud's disease, and cardiac arrhythmia. Methods of treatment described herein include prophylaxis to prevent post-cardiotomy (including but not limited to coronary artery bypass graft surgery and valve surgery) complications (including but not limited to depression, neuro-cognitive decline, congestive heart failure and infarction, clotting events, and arrhythmias) as well as for the treatment of such complications. The invention includes a method of preventing or reducing the risk of a second myocardial infarction in a subject in need thereof by providing fatty acid-containing compositions or PUFA production modulating agents and formulations as described herein to the subject at least one time per day for at least 60 days, 180 days, 360 days, or more to a patient following a first myocardial infarction.

In one embodiment, the fatty acid compositions, formulations, and agents described herein can be used to treat and/or prevent cell carcinomas. In some embodiments, the compositions, formulations and agents described herein are given to a subject in remission to reduce the risk of recurrence.

Kits

In other aspects, a kit or a package comprising the compositions, formulations and/or agents for practicing the test and treat methods of the present invention is provided. For example, a kit may include means for obtaining a biological sample from a subject. An exemplary kit may also include reagents for determining the methylation state of the cytosine at position 4490 in the nucleotide sequence of SEQ ID NO: 1 and other sites present within the enhancer regulatory element of the FADS cluster located on chromosome 11, whose methylation status is associated with an increased or decreased capacity to synthesize LcPUFAs (e.g., a cytosine at position 1237 in the nucleotide sequence of SEQ ID NO:1, a cytosine complementary to a guanosine at position 2410 in the nucleotide sequence of SEQ ID NO:1, and a cytosine complementary to a guanosine at position 12844 in the nucleotide sequence of SEQ ID NO:1). Such reagents can include site-specific probes and/or primers that facilitate isolation and biochemical characterization of nucleic acids comprising the aforementioned methylation site(s). The kits may optionally include packaged pharmaceutical formulations comprising one or more PUFA dosage forms or PUFA modulating agents in a container; and instructions for using the dosage form for prophylactic or therapeutic treatment of a subject. In some embodiments, the present invention provides a kit comprising a pharmaceutical composition of the present invention. The kit can contain one or more separate containers.

Although the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container. For example, wherein the components of the kit are in lyophilized form, the kit may optionally contain a sterile and physiologically acceptable reconstitution medium such as water, saline, buffered saline, and the like.

In some embodiments, the containers of the kit can include at least one vial, test tube, flask, bottle, syringe, finger prick test or other containers, into which the compositions/formulations of the present invention, and any other desired agent, may be placed and suitably aliquoted. Where separate components are included, the kit will also generally contain at least a second container into which these are placed, enabling the administration of separated designed doses. The kits may also comprise additional containers for containing a sterile, pharmaceutically acceptable buffer or other diluent.

Screening Assays

The methods described herein include methods (also referred to herein as "screening assays") for identifying compounds that modulate (i.e., increase or decrease) methylation at the CpG sites described herein. Such compounds include, e.g., polypeptides, peptides, antibodies, peptidomimetics, peptoids, small inorganic molecules, small non-nucleic acid organic molecules, nucleic acids (e.g., antisense nucleic acids, siRNA, oligonucleotides, synthetic oligonucleotides), carbohydrates, or other agents that interfere with or modulate specific methylation of the enhancer region within the FADS gene cluster, have a stimulatory or inhibitory effect on, for example, LcPUFA production within a subject. Compounds thus identified can be used to modulate the expression and/or activity of FADS1 and FADS2 genes and their encoded proteins and enzymatic products, LcPUFAs in a prophylactic and/or therapeutic protocol.

In general, screening assays involve assaying the effect of a test agent on expression or activity of a target nucleic acid or target protein in a test sample (i.e., a sample containing the target nucleic acid or target protein). Expression or activity in the presence of the test compound or agent can be compared to expression or activity in a control sample (i.e., a sample containing the target protein that is incubated under the same conditions, but without the test compound). A change in the expression or activity of the target nucleic acid or target protein in the test sample compared to the control indicates that the test agent or compound modulates expression or activity of the target nucleic acid or target protein and is a candidate agent.

Compounds can be tested for their ability to modulate one or more activities mediated by a FADS protein as described herein. For example, compounds that modulate fatty acid desaturase expression or activity can be tested for their ability to treat disorders associated with aberrant LcPUFA levels. Methods of assaying a compound for such activities are known in the art. In some cases, a compound is tested for the ability to directly affect target gene expression or modulate methylation status, thereby influencing fatty acid production levels.

The test compounds used in the methods described herein can be obtained using any of the numerous approaches in the art including combinatorial libraries, biological libraries; peptoid libraries (libraries of molecules having the functionalities of peptides, but with a novel, non-peptide backbone, which are resistant to enzymatic degradation but remain bioactive; e.g., Zuckermann et al. (1994) *J. Med. Chem.* 37:2678); spatially addressable parallel solid phase or solution phase libraries; synthetic library methods requiring deconvolution; the "one-bead one-compound" library method; and synthetic library methods using affinity chromatography selection. The biological library and peptoid library approaches are specific for peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the literature, for example in: DeWitt et al. *Proc. Natl. Acad. Sci. USA*, 90:6909, 1993; Erb et al. *Proc. Natl. Acad. Sci. USA*, 91:11422, 1994; Zuckermann et al. *J. Med Chem.* 37:2678, 1994; Cho et al., *Science* 261:1303, 1993; Carrell et al. *Angew. Chem. Int. Ed. Engl.* 33:2059, 1994; Carell et al. *Angew. Chem. Int. Ed. Engl.* 33:2061, 1994; and Gallop et al. *J. Med. Chem.*, 37:1233, 1994.

Libraries of compounds may be presented in solution (e.g., Houghten, *Bio/Techniques*, 13:412421, 1992), or on beads (Lam, *Nature*, 354:82-84, 1991), chips (Fodor, *Nature* 364:555-556, 1993), bacteria (U.S. Pat. No. 5,223,409), spores (U.S. Pat. Nos. 5,571,698; 5,403,484; and 5,223,409), plasmids (Cull et al. *Proc. Natl. Acad. Sci. USA.* 89; 1865-1869, 1992) or phage (Scott and Smith, *Science,* 249:386-390, 1990; Devlin, *Science,* 249:404-406, 1990; Cwirla et al. *Proc. Natl. Acad. Sci. USA,* 87:6378-6382, 1990; and Felici, *J. Mol Biol.* 222:301-310, 1991).

In some embodiments, a cell-based assay is employed in which a cell that expresses the FADS gene cluster or biologically active portions thereof is contacted with a test compound. The ability of the test compound to modulate expression or activity of the gene cluster is then determined. The cell can be, for example, a yeast cell or a cell of mammalian origin, e.g., rat, mouse, or human.

The present invention will now be described with reference to the following examples. It should be appreciated that these examples are for the purpose of illustrating aspects of the present invention, and do not limit the scope of the invention as defined by the claims.

EXAMPLES

Example 1

Methylation within the FADS Cluster is Associated with FADS Activity and the Formation of LcPUFAs in Human Liver SNP association studies have identified thousands of associations between common variants and phenotypic trait (for review, see Hindorff et al. 2009. *Proc. Natl. Acad. Sci. U.S.A* 106:9362-9367). However, very few studies have clearly determined the actual molecular mechanisms that underlie the observed SNP-trait associations. Variants may affect gene expression in several ways, including altering transcriptional start sites, the regulatory landscape (e.g., promoter or enhancer) of a gene, alternative splicing, transcript degradation, and transcription of non-coding RNA. Association of SNPs with phenotype is often due to an unidentified genetic variant in LD with an associated SNP, or an epigenetic alteration, that is responsible for the observed biological variation and not the actual associated SNP itself. Genome-scale mapping of DNA methylation suggests that methylation has the potential to impact gene transcription via a variety of mechanisms, depending on its location (i.e., transcriptional start sites, gene bodies, regulatory elements and repeat sequences) within the transcriptional unit.

We examined the potential associations between genotypes in a SNP, rs174537, which has been strongly correlated with FADS1 activity and methylation at 485,577 CpG sites throughout the human genome. As the liver is known to be a primary organ involved in LcPUFA biosynthesis, DNA was extracted from 144 liver samples obtained from the Pathobiological Determinants of Atherosclerosis in Youth (PDAY) study. Briefly, PDAY was an autopsy study designed to examine the pathogenesis of atherosclerosis in young people. For this study, we assessed 72 European American and 72 African American males, 15 to 34 years of age, who died of violent causes within 72 hours after injury and underwent autopsy in one of the cooperating medical examiners' laboratories. The rs174537 genotypes were obtained as part of a custom genotyping panel of 77 SNPs, utilizing the Sequenom iPlex genotyping system. To determine if there were associations within the human genome, all probes represented on the Illumina HumanMethylation450 BeadChip (485,577 CpG sites) were tested for association with rs174537.

Figure 5:
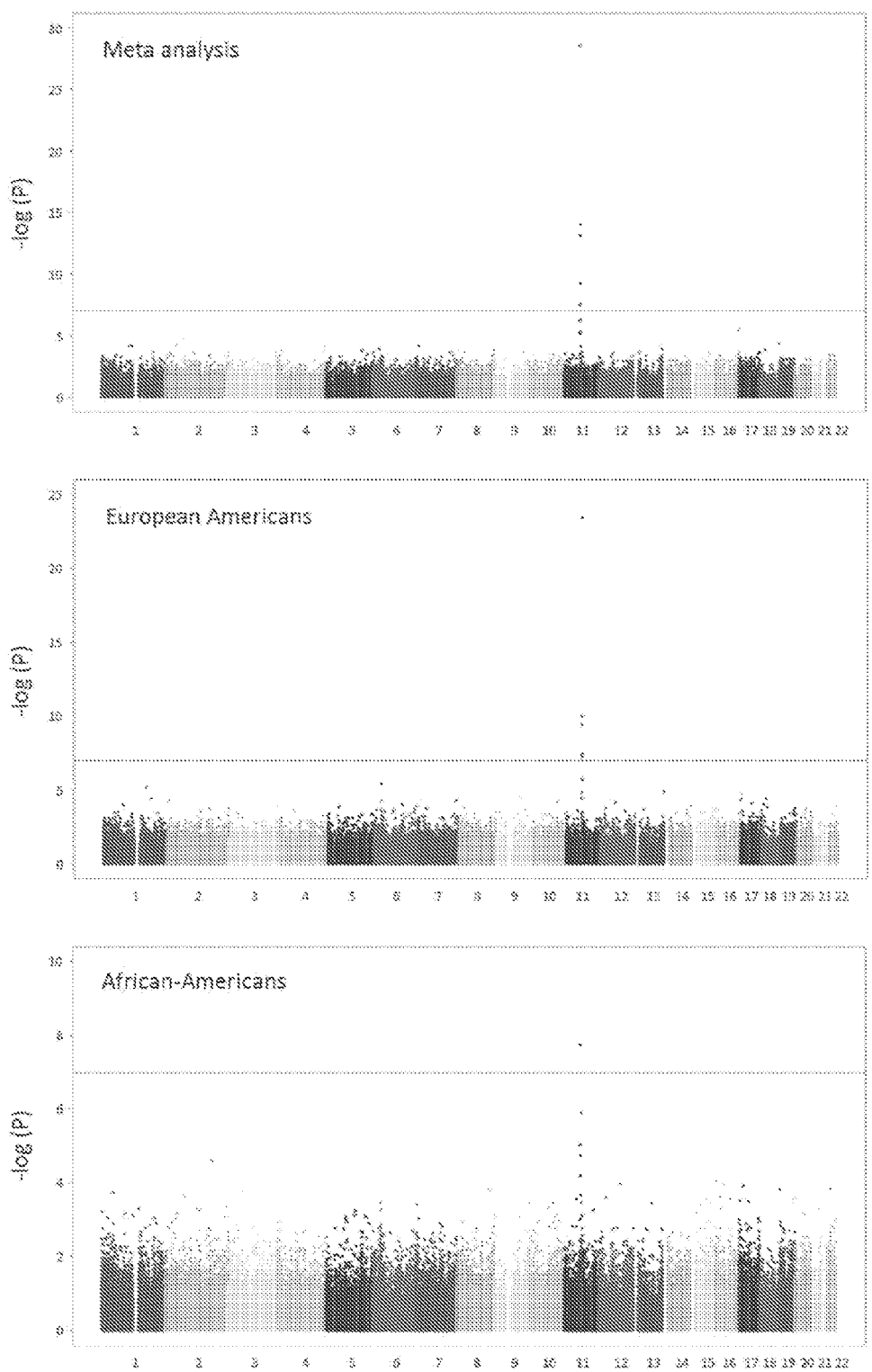
FIG. 5. Manhattan plots for association of rs174537 with HumanMethylation450 sites. P-values are based on the genetic trend test and adjusted for age, chip, and chip position. The horizontal dashed line indicates the Bonferroni-adjusted level of significance of $1.03 \times 10^{-7}$ (0.05/485,000). The upper panel shows results from the meta-analysis (using European Americans and African-Americans), the middle panel shows European Americans only, and the lower panel shows African-Americans only.

There was only one region of the human genome and only 5 CpG sites out of 485,577, where methylation of CpG sites was associated with rs174537 in both populations. Meta-analysis was also performed combining both populations, accounting for sample size and direction of effect (FIG. 5). The most significant association was observed with the methylation probe cg27386326 ($p=2.69 \times 10^{-29}$ for the meta-analysis; $p=3.66 \times 10^{-24}$ in European Americans and $p=1.78 \times 10^{-08}$ in African Americans), located approximately 3.5 kb from the FADS1 transcription initiation site. Four other sites: cg16213375 ($p=9.76 \times 10^{-15}$), cg10515671 ($p=6.93 \times 10^{-14}$), cg03805684 ($p=6.22 \times 10^{-10}$), and cg19610905 ($p=3.09 \times 10^{-8}$)-reached a Bonferroni-adjusted level of significance (i.e., $0.05/485,000=1.03 \times 10^{-7}$; horizontal dashed line in FIG. 5).

Figure 6:
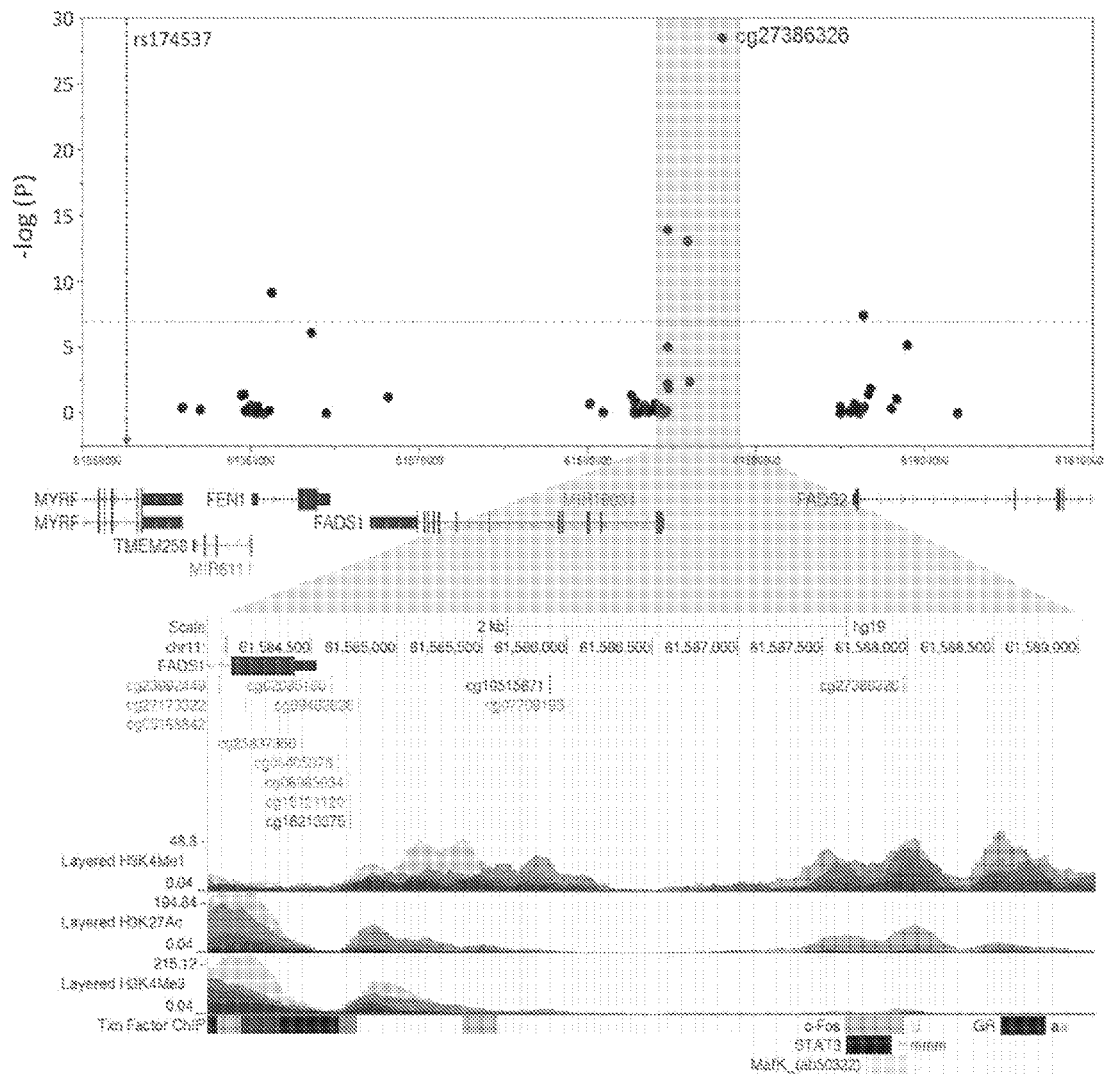
FIG. 6. Localization of FADS cluster CpG sites to enhancer region in FADS cluster. The lower panel shows the location of the CpG sites relative to the ENCODE data for H3K4Me1, H3K27AC, and H3K4Me3 histone marks, respectively, which indicate promoter and/or regulatory regions in seven cell lines. The peak methylation site is cg27386326, and the other two sites from the region that met Bonferroni adjustment are above the horizontal dashed line.

GpC sites in GpC islands in or around transcriptional start sites are believed to be the primary locations where gene expression is regulated. Surprisingly, the methylation loci identified in this study were not near transcriptional start sites but were located in a regulatory region located between FADS1 and FADS2 (FIG. 6). ENCODE regulation tracks revealed that the highly associated methylation region is located in a region that has an "enhancer signature," namely monomethylation of histone H3 lysine4 (H3K4me1) and acetylation of H3K27 (H3K27Ac; lower zoomed portion of FIG. 6). In addition, this site is in or near transcription factor binding sites for c-Fos, STAT3 and MafK.

Figure 7:
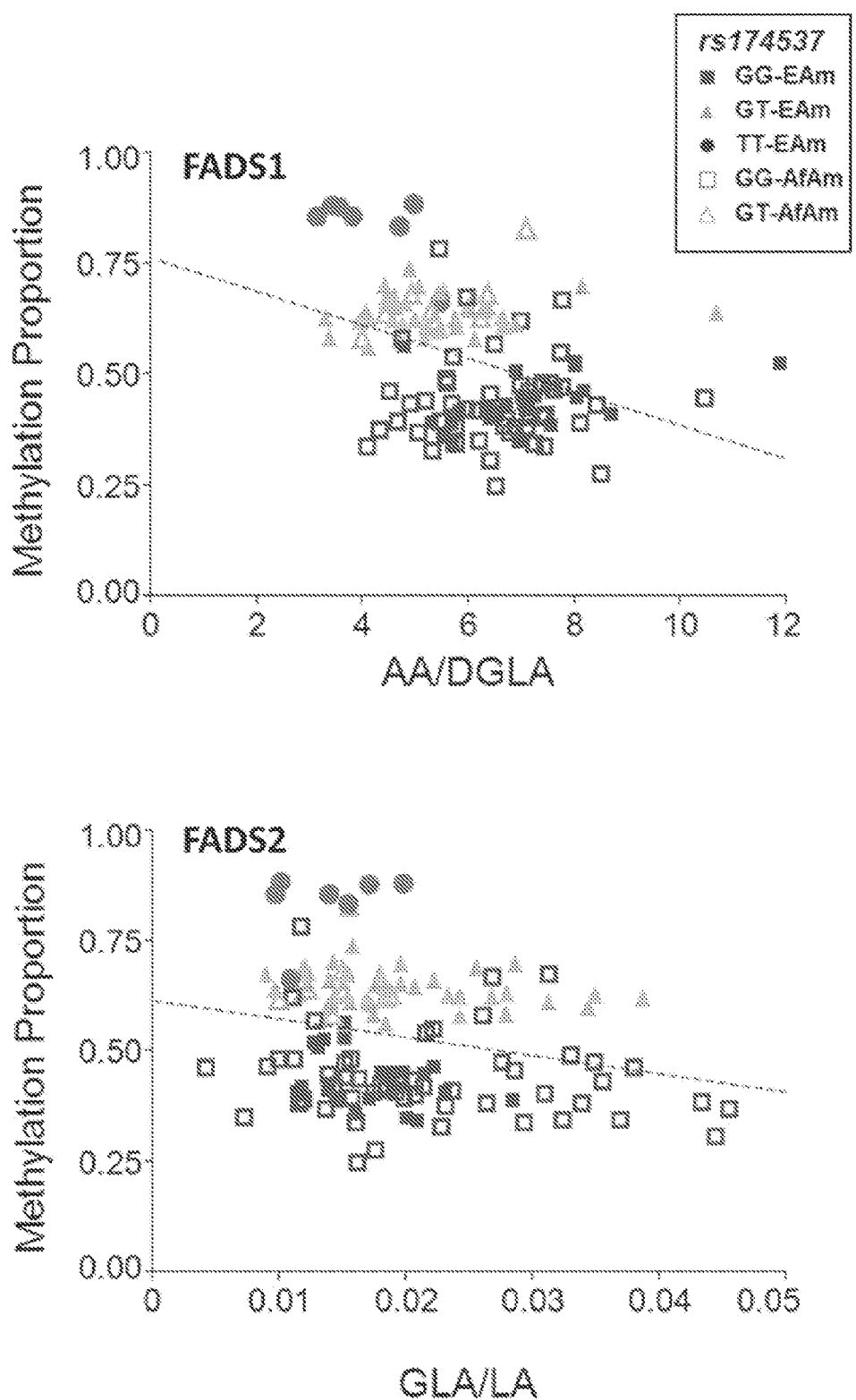
FIG. 7. DNA methylation ratio of the cytosine at position 4490 in the nucleotide sequence of SEQ ID NO:1 and FADS1 (AA/DGLA) and FADS2 (GLA/LA) efficiencies.

To determine if methylation of the cytosine at position 4490 in the nucleotide sequence of SEQ ID NO: 1 was simply associated with the SNP rs174537 or played a causal role in regulating FADS activity, we examined the association between its methylation status and FADS1 and FADS2 enzymatic activity/efficiency using the ratio of levels of AA to DGLA and GLA to LA, respectively. FIG. 7 shows there was a strong association between methylation status and FADS1 activity in liver tissues (ANOVA $p=3.99 \times 10^{-6}$). FADS2 activity also showed a relationship with methylation status. In contrast the product of the FADS1 reaction, ARA, accumulates in cells and tissues. The methylation proportion differed dramatically in individuals ranging from 25 to 90%. To our knowledge, this magnitude of allele-specific or associated methylation has not been observed outside of the imprinting and X-chromosome inactivation context.

A possible explanation for the association between the genetic variant rs174537 and the methylation level observed at the cytosine located at position 4490 in SEQ ID NO:1 is that a SNP in linkage disequilibrium (LD) with rs174537 exists at the targeted CpG site. Such a methylation-altering SNP, known as an mSNP, would lead to an apparent change in DNA methylation that was actually due to alternate genotypes at the CpG site. To rule out this possibility, we sequenced the region encompassing the cytosine at position 4490 in the study population and found no SNP within the 50 bp probe sequence or the targeted CpG site.

Taken together, these data reveal that there is a very small region of methylated DNA (containing 5 methylation loci) in a regulatory enhancer that lies between the two proximal promoters of the two functional desaturase genes (FADS1 and FADS2), and the methylation status of this region controls the efficiency of these two desaturase genes and thus the LcPUFA biosynthetic pathway in humans. Specifically, the degree of methylation of this region is correlated with the enzymatic efficiencies of FADS1, FADS2, and thus PUFA biosynthetic capacity in human tissues. Thus, it is the epigenetic informational content (i.e., the methylation of five cytosine residues in a very specific region of the human genome) that is not present in isolated cloned FADS genes and not seen in the DNA sequences of the FADS genes that determines the degree to which the FADS genes are turned on and thus individual PUFA biosynthetic activity. It has been shown that there are enhancers in the human genome located at variable distances from promoters that can play a key role in regulating gene expression. While they are typically in CpG-poor regions, whole-methylome analysis has shown them to have highly variable levels of methylation but until the present invention, the interaction between this methylation and gene activities around the enhancer has been poorly understood.

Figure 8:
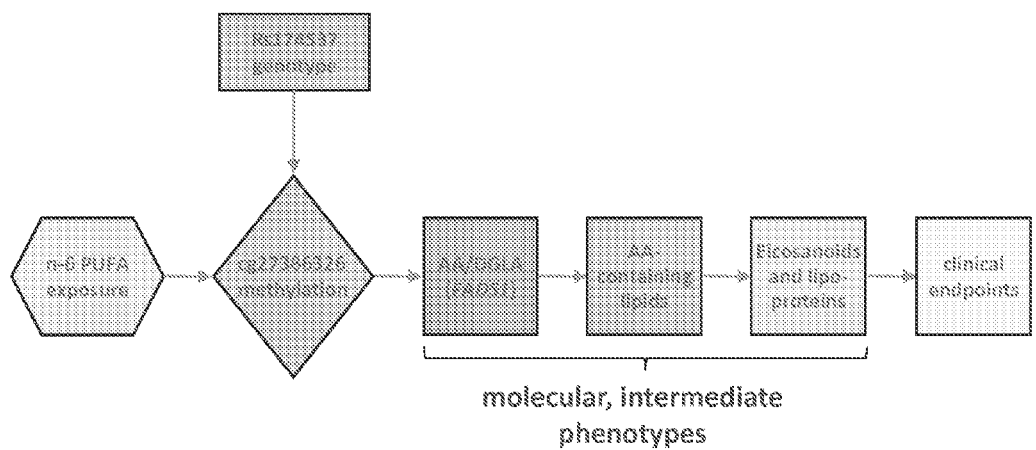
FIG. 8. Model for the causal role of methylation of cytosine within the enhancer region of the invention in molecular and clinical phenotypes.

FIG. 8 shows a pathway in which methylation of the cytosine at position 4490 in the nucleotide sequence of SEQ ID NO:1 (and nearby loci) plays a key causal role in the formation of LcPUFA-containing lipids, thereby directly impacting cholesterol, triglyceride and eicosanoid formation as well as levels of n-3 LcPUFAs in critical tissues such as the brain and ultimately clinical endpoints that lead to human disease. These diseases range from inflammatory diseases caused by enhanced n-6 LcPUFAs (O6E), to cognitive, behavioral and neurological disorders caused by deficiencies in n-3 LcPUFAs (O3D). It is important to point out that knowing the causal variant (a critical DNA methylation loci) has many advantages over simple non-specific SNP associations. First as shown in FIG. 8, since the methylation loci in the enhancer are the causal variants, they directly control FADS1 and FADS2 efficiencies (expression) and are much better predictors of FADS cluster efficiencies and LcPUFA capacity. Secondly, as epigenetic markers, the methylation of these loci is not only being impacted by genetic variation within the human genome, but they are also sensing a wide range of environmental factors (including for example, age, sex, pregnancy, and previous PUFA exposure levels). These loci provide an assessment of the genetic capacity of a human to synthesize LcPUFA in the context of all of these. Thirdly, associated SNPs only provide three conditions (genotypes) and little dynamic range. For example, there is only a 40% average difference in methylation between GG and TT at rs174537. In contrast, the identification of the causal methylation loci provides a much greater and more dynamic range from a methylation proportion (methylation percentage) of 25% to 90% in the 144 tissue samples examined. Finally, identification of these loci provides the opportunity to directly treat a subject by altering methylation status of the loci. In contrast, inducing a mutation of a sequence variant such as rs174537 is much more complex. However more importantly, a mutation in a SNP such as rs174537 would be unlikely to impact FADS cluster activities as this SNP or those in LD are not causal but simply associated with FADS activities.

We and others have demonstrated large geographic variance, with a high frequency of a haplotype with an increased capacity to synthesize LcPUFAs in African and African ancestry populations and a loss of that converting capacity across Asia into North and South American native populations. Two haplotypes have been identified (A and D) based on desaturase activity efficiency and the high efficiency haplotype has been shown to be fixed in Africa, while Europe was ~75%, Eastern Asia and Oceanic region~50% and <5% in native American populations.

We examined genetic variants in 1092 individuals from 14 different populations (Mathias et al. 2012. *PLoS. One* 7, e44926). We found dramatic differences in the frequencies of variants in the FADS cluster between African verses non-African populations. These data revealed recent positive selection along a 1 Mb region on chromosome 11q12-13 in the window containing the SNP, rs174537, within Africa, with no evidence for selection in either Europe or the Americas. Simulations suggested that the target locus is likely to be within 50 kb of the signal. A selective sweep at or near rs174537 within the African continent was likely complete or nearly complete, as there is little evidence for selection within Africa. Median-joining network visualization of the haplotypes within this block suggests that the selection process occurred ~85,000 years ago.

This work confirmed marked global differences in the allele frequencies of variants in the FADS gene cluster first noted in studies on African Americans and European Americans, especially at variants strongly associated with the efficiency of conversion of PUFAs. Clearly there are wide differences in the frequencies of the specific alleles that favor enhanced LcPUFA metabolism across populations, and these frequencies typically increase with an increasing African admixture component. It is not clear why the positive selective pressure on the high efficiency FADS variants was lost after the expansion of populations from Africa. We have speculated that once LcPUFAs could be obtained in the diet due to the emergence of hunting, fishing, animal husbandry and other technological advances, the pathway lost its selective advantage. In any event, there are now large diverse global populations, and they are particularly dissimilar with regard to their capacity to synthesize LcPUFAs and the associated increased or decreased incidence of human disease.

Study Samples.

Liver samples were obtained from the Pathobiological Determinants of Atherosclerosis in Youth (PDAY) study. PDAY was an autopsy study designed to examine the pathogenesis of atherosclerosis in young people. A subset of the total population, selected for a separate study, consisted of subjects with the lowest $25^{th}$ (controls) and highest $10^{th}$ (cases) percentile of non-HDL cholesterol. Samples were from 72 European American and 72 African-American males, 15 to 34 years of age, who died of violent causes within 72 hours after injury and underwent autopsy in one of the cooperating medical examiners' laboratories. DNA was isolated from liver samples that had been stored at −70 C by [Hixson method].

SNP Genotyping.

A panel of 77 SNPs for genotyping in fatty acid candidate genes were selected by using 1) using an $r^2$ threshold of 0.7 in the HapMap CEU population, and 2) additional SNPs to guarantee tagging at an $r^2$ threshold of 0.7 in the HapMap YRI population, using the tagger option in Haploview. THE SNP rs174537 was forced to be a tagging SNP, due to its extensive associations in the literature. SNP genotyping was performed with the Sequenom iPlex genotyping system, and only rs174537 was included for analysis in this study.

Sequencing Around the cg27386326 Probe (Petition 4490 in SEQ ID NO:1).

DNA probes on the HumanMethylation450 BeadChip consist of 50 bp fragments, and the subsequent base is the assayed CpG. To exclude the possibility that the CpG site included a SNP, we sequenced the 50 bp probe and immediately surrounding sequence using Sanger sequencing. A 724 bp PCR product was amplified using the following primers: 5'-ATGATGTAAGTTTGGCTACAGAGA-3' and 5'-CAATTCAGCAAATTTATCTGGG-3'. PCR cycling conditions were 95° C., 5 min; 30 cycles of 95° C. for 30 sec, 56° C. for 30 sec, and 72° C. for 1 min; followed by a 5 min extension at 72° C. Sequencing reactions were performed using the ABI BigDye Terminator V1.1 chemistry. Sequencing products were run on an ABI 3730 XL DNA Analyzer (Applied Biosystems, Inc., Foster City, Calif.) and analyzed with Sequencher V4.8 (Gene-Codes Corp, Ann Arbor, Mich.).

DNA Methylation Analysis.

Samples were evaluated using the Illumina HumanMethylation450 BeadChip, which assays 485,577 unique CpG sites. The average beta (essentially the ratio of the methylated to unmethylated signal) for each site was used to test for differences by genotype. Association analysis was performed in the European American and African-American samples separately using a generalized linear model (proc glm), as implemented in SAS (Cary, N.C.). Age, chip, and chip position were included in the model as covariates. Meta analysis was performed using METAL, weighting by sample size and accounting for direction of effect.

Isolation of Fatty Acids from Liver Samples.

The fatty acid profile was evaluated in homogenized liver samples. Tissue was homogenized in ice-cold deionized water at 100 mg/ml. Fatty acid methyl esters were prepared in triplicate homogenate samples (100 μl) and analyzed by gas chromatography. Fatty acids in samples were identified based on retention times of commercially available authentic fatty acid methyl esters.

Example 2

Analysis of Methylation Status of Tissue from Cancer Patients

Arachidonic acid and products from this long chain omega-6 polyunsaturated fatty acid such as prostaglandin E2 and leukotrienes play a role in inducing cancer cell proliferation, migration and invasion, and survival (Wang and DuBois *Nature Reviews Cancer* 10:181-193 (2010). Consequently, the ability to determine whether an individual cancer patient or a subject at increased risk of having or developing cancer is putting himself or herself at risk due to the fatty acid composition of his/her diet would be of great value. With this knowledge, a cancer patient or subject at increased risk of cancer could make specific alterations to his/her diet with regard to polyunsaturated fatty acids both in terms of foods, dietary supplements, medical foods and prescription products to attenuate the biological properties (increasing cancer cell proliferation, migration and invasion, and survival) of arachidonic acid and its metabolites.

Figure 10:
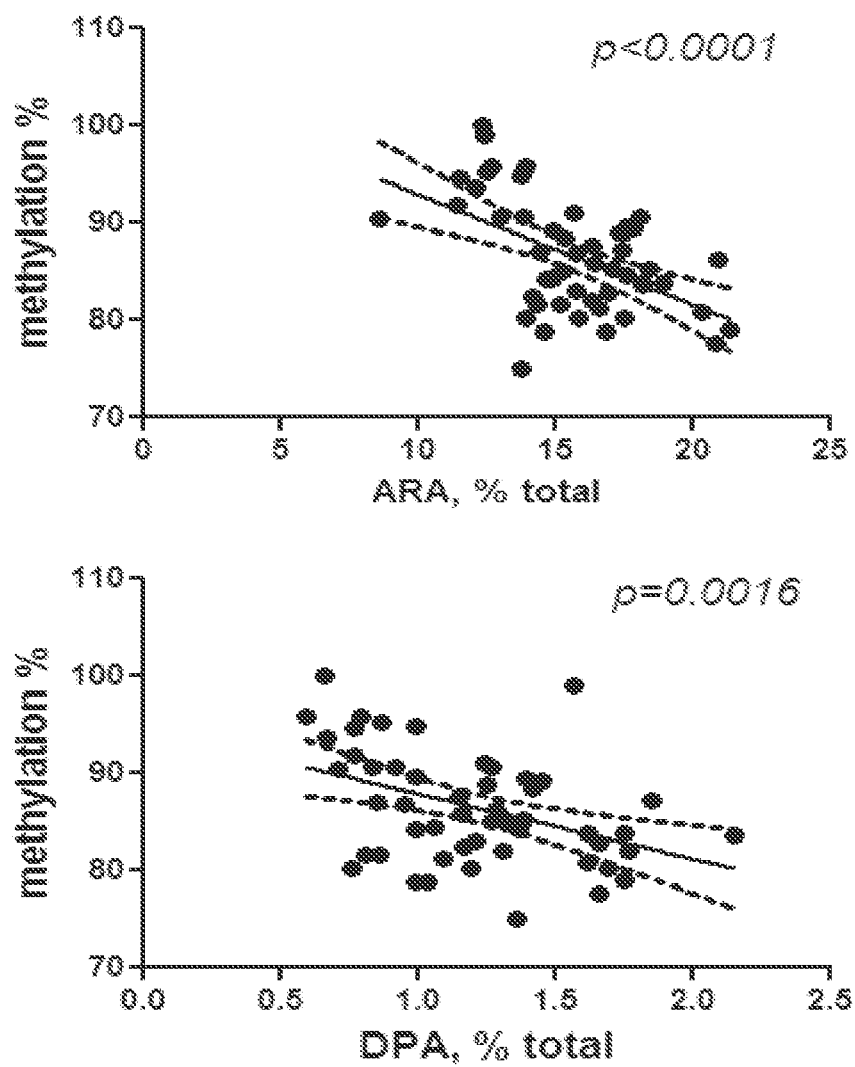
FIG. 10. Association between the methylation percentage at cg27386326 CpG locus in DNA from prostate tissue and arachidonic acid and docosapentaenoic acid levels.
Figure 11:
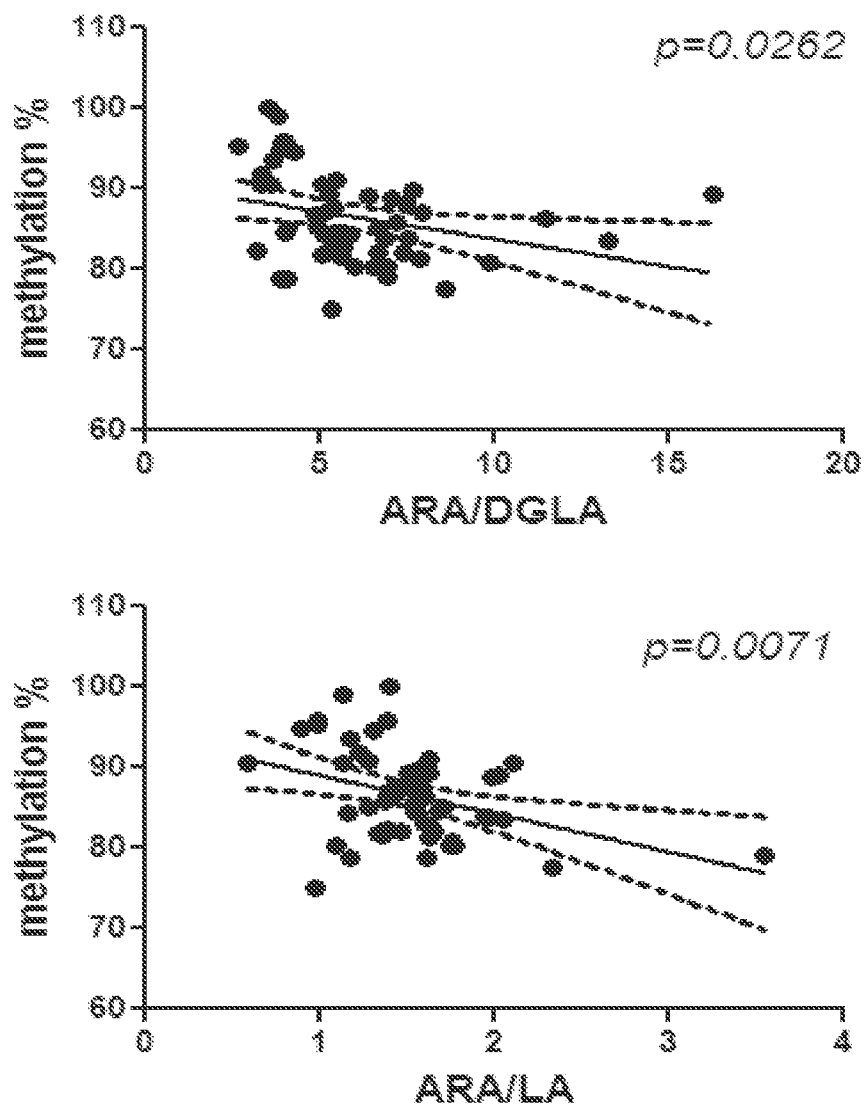
FIG. 11. Association between the methylation percentage at the cg27386326 CpG locus in DNA from prostate tissue and ratio of arachidonic acid and dietary precursors of arachidonic acid, dihommo gammalinolenic acid and linoleic acid.

To identify prostate cancer patients who are at increased risk of exacerbating their cancer due to their exposure to polyunsaturated fatty acids from their diet and the subsequent conversion of these polyunsaturated fatty acids to cancer-inducing arachidonic acid and products, we examined the association between the methylation percentage in the cg27386326 site (utilizing pyrosequencing at that particular site) and the levels of long chain polyunsaturated fatty acids in those tissues. FIG. 10 shows the strong a negative association between the methylation percentage and levels of arachidonic acid (n-6 long chain polyunsaturated fatty acid) and docosapentaenoic acid (n-3 long chain polyunsaturated fatty acid) in the prostate tissue. FIG. 11 illustrates the relationship between the methylation percentage and the product: precursor ratios in the biochemical pathway of the prostate tissue. These ratios are a surrogate marker of the desaturase activity necessary to make the n-6 long chain polyunsaturated fatty acid, arachidonic acid. As shown in FIG. 11 and similar to the liver, the methylation percentage is highly correlated with the capacity of prostate tissue to make arachidonic acid from dietary precursors with a higher methylation percentage associated with a reduced capacity to synthesize ARA. Taken together, these data indicate that methylation percentage of prostate tissue is a strong genetic marker of the capacity of the prostate tissue to produce cancer-inducing omega-6 polyunsaturated fatty acids and their products, thereby quantifying the risk imposed by polyunsaturated fatty acids in an individual's diet on cancer incidence and progression.

Figure 12:
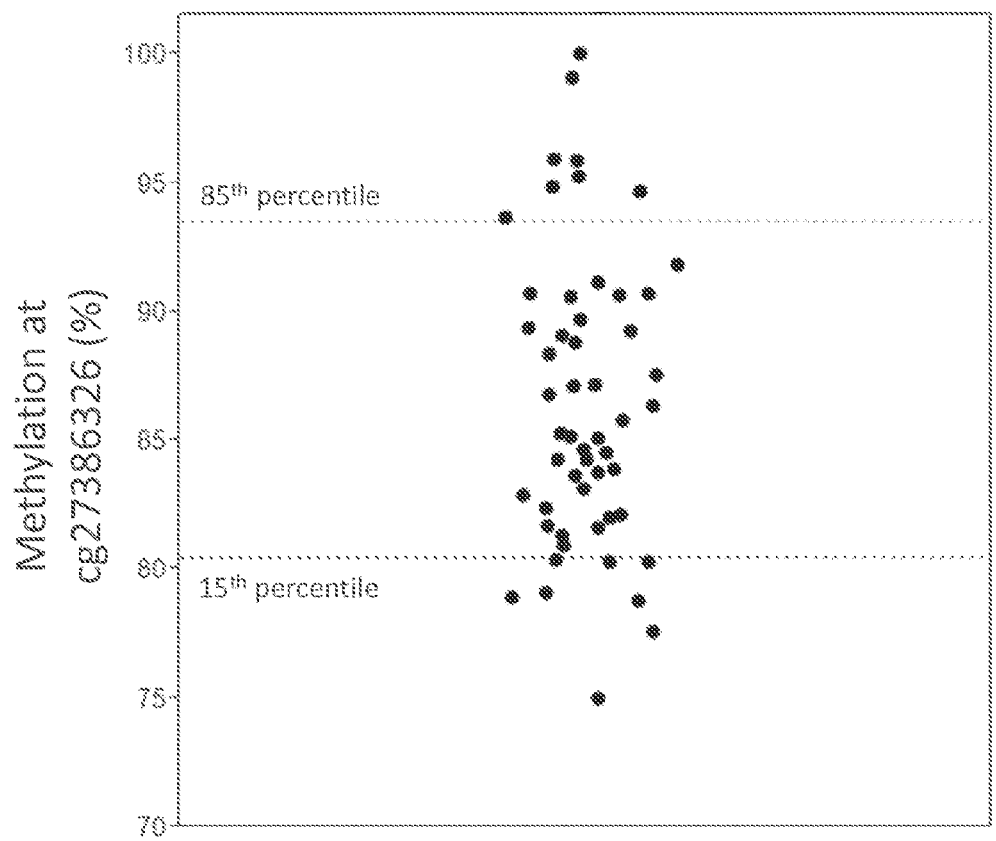
FIG. 12. Methylation percentage at the cg27386326 CpG locus in DNA from prostate tissue. Threshold values at the $15^{th}$ and $85^{th}$ percentiles are indicated.
Figure 13:
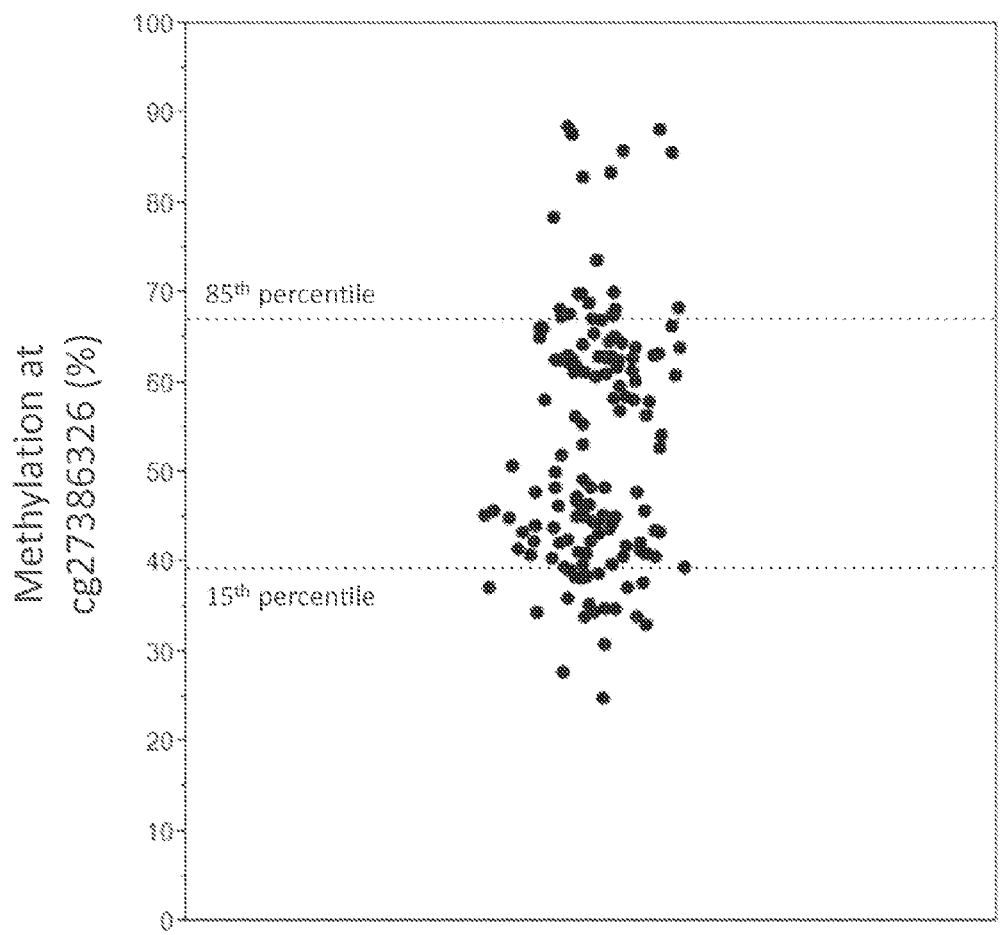
FIG. 13. Methylation percentage at the cg27386326 CpG locus in DNA from liver tissue. Threshold values at the $15^{th}$ and $85^{th}$ percentiles are indicated.
Figure 14:
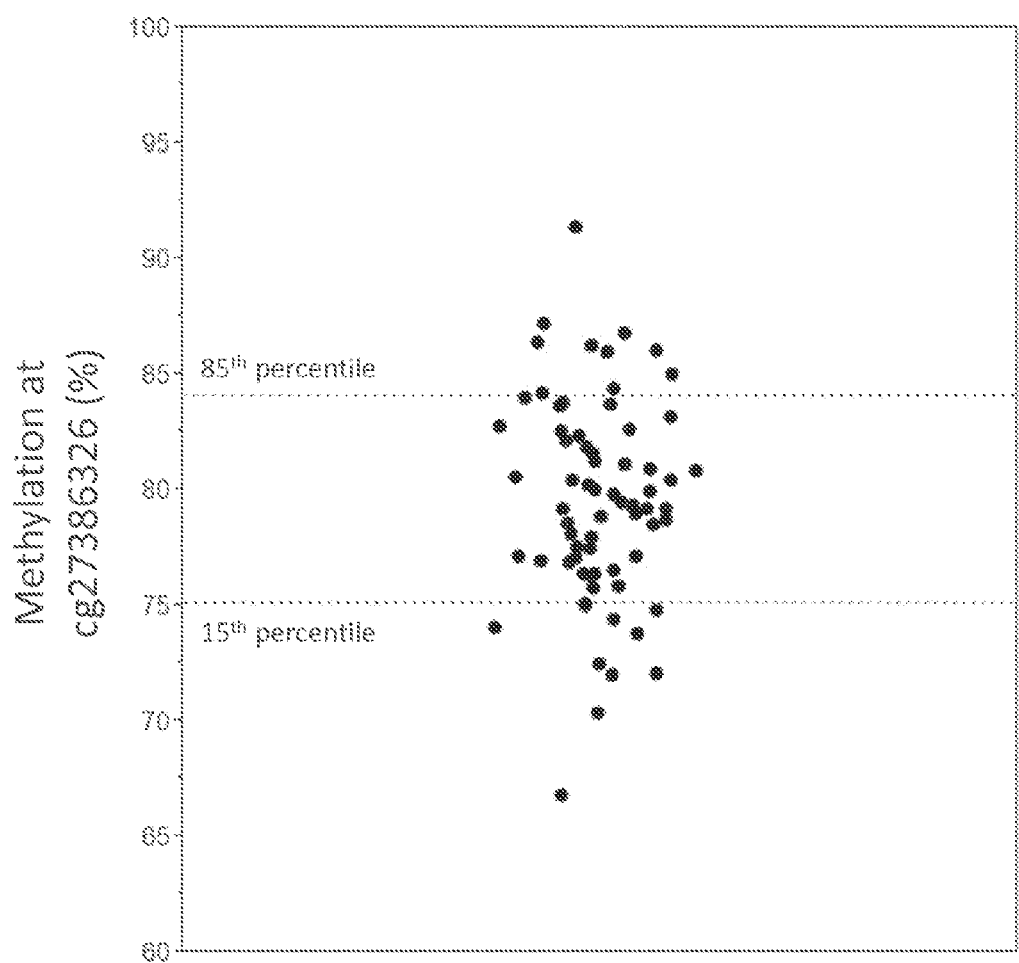
FIG. 14. Methylation percentage at the cg27386326 CpG locus in DNA from whole blood. Threshold values at the $15^{th}$ and $85^{th}$ percentiles are indicated.
Figure 15:
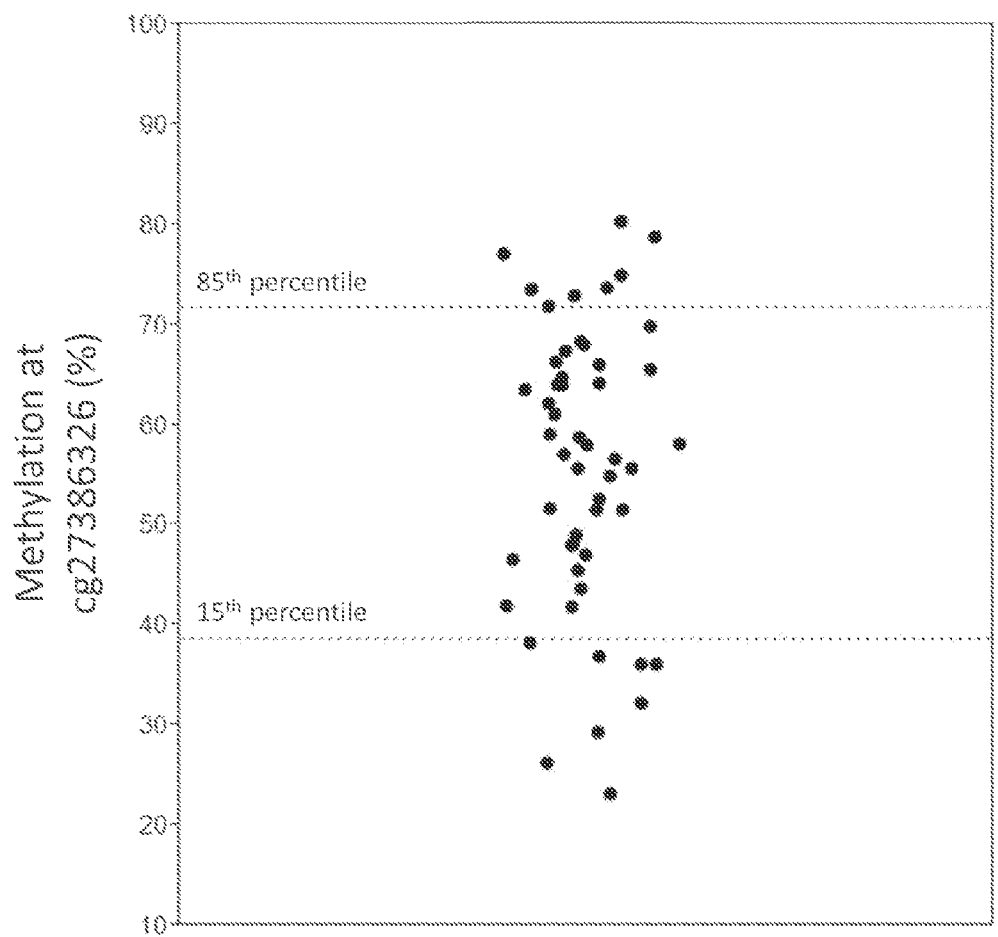
FIG. 15. Methylation percentage at the cg27386326 CpG locus in DNA from saliva. Threshold values at the $15^{th}$ and $85^{th}$ percentiles are indicated.

The methylation percentage at cg27386326 has been measured in DNA from four different sample types. In DNA from prostate tissue, the dynamic range of methylation extends from about 75% to 100% (FIG. 12). The thresholds for high (85$^{th}$ percentile) and low (15$^{th}$ percentile) producers are about 93% and 81%, respectively, and are shown as dashed lines in the figure. In DNA from liver tissue, the dynamic range of methylation extends from about 24% to 89% (FIG. 13). The thresholds for high (85$^{th}$ percentile) and low (15$^{th}$ percentile) producers are about 66% and 40%, respectively, and are shown as dashed lines in the figure. In DNA from whole blood, the dynamic range of methylation extends from about 66% to 92% (FIG. 14). The thresholds for high (85$^{th}$ percentile) and low (15$^{th}$ percentile) producers are about 84% and 75%, respectively, and are shown as dashed lines in the figure. In DNA from saliva, the dynamic range of methylation extends from about 23% to 81% (FIG. 15). The thresholds for high (85$^{th}$ percentile) and low (15$^{th}$ percentile) producers are about 70% and 40%, respectively, and are shown as dashed lines in the figure.

To determine the DNA methylation percentage in CD4+ T cells, these cells will first be isolated from whole blood. Using standard methodologies (e.g., magnetic beads, immunoprecipitation, etc.), the CD4+ T cells will be separated from other cell types present in whole blood and the DNA will be isolated from these cells specifically. DNA methylation analysis will be performed using any of the previously described methods (e.g., sequencing of bisulfite treated DNA, etc.), and the methylation percentage will be determined. The same thresholds described for the other cell types and tissues (15$^{th}$ and 85$^{th}$ percentiles) will be used to define the DNA methylation percentage cutoff values for O3D and O6E.

REFERENCES

Hindorff et al. Potential etiologic and functional implications of genome-wide association loci for human diseases and traits, *Proc. Natl. Acad. Sci. U.S.A.* 106, 9362-9367 (2009)

Jones Functions of DNA methylation: islands, start sites, gene bodies and beyond. *Nat. Rev. Genet.* 13, 484-492 (2012)

Needleman et al. Arachidonic acid metabolism. *Annu. Rev. Biochem.* 55, 69-102 (1986)

Marquardt et al. cDNA cloning, genomic structure, and chromosomal localization of three members of the human fatty acid desaturase family. *Genomics* 66, 175-183 (2000)

Blanchard et al. Fatty Acid Desaturase 3 (Fads3) is a singular member of the Fads cluster. *Biochimie* 93, 87-90 (2011)

Lattka et al. FADS gene cluster polymorphisms: important modulators of fatty acid levels and their impact on atopic diseases. *J. Nutrigenet. Nutrigenomics.* 2, 119-128 (2009)

Gieger et al. Genetics meets metabolomics: a genome-wide association study of metabolite profiles in human serum. *PLoS. Genet.* 4, e1000282 (2008)

Illig et al. A genome-wide perspective of genetic variation in human metabolism. *Nat. Genet.* 42, 137-143 (2010)

Kathiresan et al. Six new loci associated with blood low-density lipoprotein cholesterol, high-density lipoprotein cholesterol or triglycerides in humans. *Nat. Genet.* 40, 189-197 (2008).

Willer et al. Newly identified loci that influence lipid concentrations and risk of coronary artery disease. *Nat. Genet.* 40, 161-169 (2008).

Kathiresan et al. Common variants at 30 loci contribute to polygenic dyslipidemia. *Nat. Genet.* 41, 56-65 (2009)

Aulchenko et al. Loci influencing lipid levels and coronary heart disease risk in 16 European population cohorts. *Nat. Genet.* 41, 47-55 (2009).

Mathias et al. The impact of FADS genetic variants on omega6 polyunsaturated fatty acid metabolism in African Americans. *BMC Genet.* 12, 50 (2011)

Sergeant et al. Differences in arachidonic acid levels and fatty acid desaturase (FADS) gene variants in African Americans and European Americans with diabetes or the metabolic syndrome. *Br. J. Nutr.* 107, 547-555 (2012)

Schadt. et al. Mapping the genetic architecture of gene expression in human liver. *PLoS Biol.* 6, e107 (2008)

Mathias et al. Adaptive evolution of the FADS gene cluster within Africa. *PLoS One.* 7, e44926 (2012)

Gibbs. et al. Abundant quantitative trait loci exist for DNA methylation and gene expression in human brain. *PLoS Genet.* 6, e1000952 (2010)

Zhang et al. Genetic control of individual differences in gene-specific methylation in human brain. *Am. J. Hum. Genet.* 86, 411-419 (2010)

Wissler. Update on the pathogenesis of atherosclerosis. *Am. J. Med.* 91, 3S-9S (1991)

Sigurdsson et al. HapMap methylation-associated SNPs, markers of germline DNA methylation, positively correlate with regional levels of human meiotic recombination. *Genome Res* 19, 581-589 (2009)

Lister et al. Human DNA methylomes at base resolution show widespread epigenomic differences. *Nature* 462, 315-322 (2009)

Schmidl et al. Lineage-specific DNA methylation in T cells correlates with historic methylation and enhancer activity. *Genome Res.* 19, 1165-1174 (2009)

Wiench. et al. DNA methylation status predicts cell type-specific enhancer activity. *EMBO. J.* 30, 3028-3039 (2011)

Biasbalg et al. Changes in consumption of omega-3 and omega-6 fatty acids in the United States during the 20th century. *Am. J. Clin. Nutr.* 93, 950-962 (2011)

Hibbeln et al. Omega-3 fatty acid deficiencies in neurodevelopment, aggression and autonomic dysregulation: opportunities for intervention. *Int Rev Psychiatry* 18(2): 107-18 (2006)

Park et al. Interactions between the APOA5-1131T>C and the FEN1 10154G>T polymorphisms on omega6 polyunsaturated fatty acids in serum phospholipids and coronary artery disease. *J. Lipid Res.* 51, 3281-3288 (2010)

Martinelli et al. FADS genotypes and desaturase activity estimated by the ratio of arachidonic acid to linoleic acid are associated with inflammation and coronary artery disease. *Am. J. Clin. Nutr.* 88, 941-949 (2008)

Hong et al. Association of polymorphisms in FADS gene with age-related changes in serum phospholipid polyunsaturated fatty acids and oxidative stress markers in middle-aged nonobese men. *Clin. Interv. Aging* 8, 585-596 (2013)

Barrett et al. Haploview: analysis and visualization of LD and haplotype maps. *Bioinformatics.* 21, 263-265 (2005)

Willer et al. METAL: fast and efficient meta-analysis of genomewide association scans. *Bioinformatics.* 26, 2190-2191 (2010)

Metcalfe et al. Rapid preparation of fatty acid esters from lipids for gas chromatographic analysis. *Anal. Chem.* 38, 514-515 (1966)

Weaver et al. Effect of dietary fatty acids on inflammatory gene expression in healthy humans. *J. Biol. Chem.* 284, 15400-15407 (2009)

While certain of the embodiments of the present invention have been described and specifically exemplified above, it is not intended that the invention be limited to such embodiments. It will be apparent to one skilled in the art that various changes and modifications can be made therein without departing from the scope of the present invention, as set forth in the following claims.

Several patents, patent publications, non-patent documents and GenBank® Accession numbers are cited throughout the specification in order to describe the state of the art to which this invention pertains. Each of these documents and citations is incorporated herein by reference as though set forth in full.

The following nucleotide sequence (SEQ ID NO:2) is present in a chromosome region on chromosome 11 defined by and including base pair position 61,584,461 to base pair position 61,590,300. The methylation sites are underlined and the methylation site cg27386326 is boxed.

```
61586461   GCCTCCCAAGTAGCTGGGACTACAGGTGCCCGCCACCACGCCCAGCTAAT
61586511   TTTGTTTTGTATTTTTAGTAGAGTTGGGGTTTCACCATGTTAGCCAGGA
61586561   TGGCTTTGATCTCCTGACCTCGTGATCTGCCCGCCTCGGCCTCCCAAAGT
61586611   GCTGGGATTACAGGCGTGAGCCACCGCACCCGGCCAGAATTTAGGAATGT
61586661   TTTGAATACTGAAGAGATGAAAAAAAATAGAAAAATAAAAATGTTCCCAA
61586711   TAATTCCATGTTTAGGAATATAGCCTAAGGAAATGTTCTTAGAAAAATAT
61586761   TTATAGGTCAGGCGGGGTGCCTCACGCCTATAATCCTAGCACTTTGGGAG
61586811   GTCGAGGCAGGCGGATTGCCTGAGCTCAGGAGTTCAAGACCAGCCTGAAC
61586861   AAAAGAAATCGGCTGGGCGTGGCGGCGTGCGCCTGTAGTCCCAGCTACTC
```

-continued

```
61586911  GGGAGGCTGAGGCAGGAGAATTGCTTGAATCCGGGAGGCAGAGGTTGCAG
61586961  TGAGCCGAGATTGTGCCACTGCACTCCAGCCTGGGCAACAAAGCAAGATT
61587011  CTATATCCACACACAAAAAAAGAAAACTATTTATAAACAAAAAATATTCA
61587061  TTAAAGCAGTATCTATGATAGCGGGAAATGGAAACACTCTAAATGCCCAT
61587111  CAGTGAAATATTTTGCAGACATTGAAAATAATGTCATCTTTCCTTTAATA
61587161  CAGAATCAAGGAAAAATGTTTTATGTAAATCTTTTATTTTATTATACTTT
61587211  AAGTTTTAAGGTACATATGCACAACATGGAGGTTTGTTACATATGTATAC
61587261  ATGTGCCATGTTGGTGTGCTGCACCCATTAACTCGTCATTTAGCATTAGG
61587311  TATATCTCCTAATGCTATCCCTCCCCCCTCCCCCGAATCAAGGAAAATTA
61587361  AATAATATGATGTAAGTTTGGCTACAGAGATAACTGTTCTATAAAAAGAC
61587411  TAGGTTGGGCGCGGTGGCTCACACCTGTAATCCCAGCACTTTGGGAGGCA
61587461  GAGGCAGGTGGACCACCTGAGGCCAGGAGCTCGAGACCCACCTGGCCAAC
61587511  ATGGTGAAACTCTGTCTCTACTAAAATACAAAAATTAGTGCCTGTAATCC
61587561  CAGCTACTTGGGAGGCTGAGTCAGGAGAATCACCTGGGCAACATGGTGAG
61587611  ACTGCACCTCAGAAAAAACCAAAAAACCCATACCACTTGTAAGATAATTC
61587661  CTTGATCAACCCCACCTACCTAGAACCATTCATTAAGTGTTTTATTTAAC
61587711  ATTTGTGGGTGTCTCCTCTTTGTATTCCCAGCACCTACTTTGGTAAGGT
61587761  GCTGGGAATACAAAGTTCAGTACTATATGGGTCATGCCTAGTCATGTCTA
61587811  CTGGAGGAGAGAGACAAGTGAGTCACGGATTATAGGTCAGTAGGATAGAT
61587861  GCAAATTAAATTCATCTTACTCAGGATTTAAACAGCTTATATGACATGAC
61587911  TTTGCATTCATGTTTCTTTGCTTTTCATGTGTTCTTAGGTCAGTGTCATG
61587961  TATTTTGCTACCTCCCTAACGAGCTTATAATCCAGGATAGGGCTGTGGAT
61588011  TCTGTTTATACTACCAATACATATTCAGAGCACCTTGGTTTGGAGTTCTA
61588061  GGTGGAATCCCACATAAATTTGCTGAATTGGCCGGGCGTGGCAGCTCATG
61588111  CCTGTAATCCCTGCACTTTGGGAGGGTGAGGAGGGCGGATCACCTGAGGT
61588161  CAGGAGCTCCAGACCCACTTGGCCAACACGGTGAAACCCTGTCTCTACTA
61588211  AAATACAAAAATTAGCCGGGTGTGGTGGGGGGTGCCTGTAATCCCAGCTA
61588261  CTTTGTGGGGGTGAGGCAGGAGAATCGCTTGAACCCAGGAGGCAAAGGTT
61588311  GCAGTGAGCCGAGATTGCACCACTGCACTCCAGCCTGGGTGACAGAGCCA
61588361  GACTCTGTCTCTAAATAAATAAATAAATAAAAAATTTGCTGAATCAACTG
61588411  ATGATTTCAACCTGAAAAAATACAGGTGAGTAAGCCTATAGGCCACTAGG
61588461  CAAATGTCGTGTTGCCCTCTCATCTCCTTACCCACCTACACAGGTGGTCA
61588511  CACAGACTGCAATAAACCCATATCCAGGTCAACTAAAGGAAACCTTTGCC
61588561  TTGCAGGCCCTGTTGATCCTAAGGGAACTTGCCTCATCCTGGATATGAAT
61588611  CACATACTTAATTTTAGGTTGCCACTTGTGAATACTAACTGTTCTGGCCA
61588661  AATTAATCCTCAAGGAACAGAACGAAATGAGCTTAAGACCCTAATGCCAG
61588711  GCCAGGCACAGTGACTCGTGCCTATAATCCCAGTGCTTTGGGAGGCTGAG
61588761  GTGGGAGGATTACTTGAGCTCAGGAGTTGGAGACCAGCCTAGACAACATA
61588811  GTGAGACCCCTTCCTAACTGTCCCACCATTTTCTCTCTAAAGAAAAGAAA
61588861  AAAAAAGACCTTAATGCCGATTGTAATGAAGCCATAATTGAATAACCTAA
```

-continued

```
61588911  CTGCCAGTGGCTGTTGGAATAACCTGAATTGTGAGTTCAAATTTTGATCC
61588961  ATTTTAACAAAAGATCCTAAACATAATAGTTGGCCAATAGCCTGGATCCT
61589011  TTACAAAGTCAACACATATAGGAGAAGCAATACCGGTTGTGCTCAGCCTC
61589061  TGCTGCAGCCTCCCCTCAGTAGCAGCCCTTCAGGCCATTAAAGACCAAAA
61589111  CCATTTTTGAAAAATCTGGATTTCTGTGAAATTGGATAACTTATGGGGGT
61589161  GCAGTGACTACAACACAGTAGGCACTAATAAAGTTGACAGAATCAGTCTT
61589211  TGTTTTAAGAAAAGTCATCTGTAATAATTCTGCAGATTAATGTTAAGTAA
61589261  TATTAAAAATAATTTATGACATATAGTGCTTAAACTAAAGGGAGAATCCC
61589311  AATCATACCTCTATTAGAGGCAGAGCGAGAGCTAGAAACAGGACTCTCAT
61589361  TTTGCTGCATTCTAAGAGTGTGGGAGATTGGGATGGGGCAGAGGCAGGCT
61589411  CATGGAGGAATTCACGGGATTTCCTTAATGCAGTCTTTTTTTTTTTTTG
61589461  AGACAGAGTCTCGCTCTGTCACCCAGGCTGGAGTGCAGTGGTGCTGTCTT
61589511  GGCTCACTGCAACCTCCGCCTCCAGGGCTCACGCCATTCTCCTGCCTCAG
61589561  CCTCCTGAGTAGCTGGGACTACAGGCGTCTGCCACCACGCCTGGCTAATT
61589611  TTTTGTATTTTCAGTAGAGACAAAGTTTCACCATGTTAGCCAGGATGGTC
61589661  TCCATCTCCTGACTTGGTGATCCACCCGCCTCAGACTCCCAAAGTGCTGG
61589711  GATTACAGGCGTGAGCCACCGCGCCCGGCCCAGTCTTCTTATCATTGTAT
61589761  AGAATATAGATGCCTTAGGGACAGATATATTAAACCCACTGTTTTATAGA
61589811  CAAGGTGACAGATCCAAAGAGCTGAAGCCACACATGAAATTTAGTATATT
61589861  TGGGGCTAGAATTTACCCCAGAACTTATTTATAACTTTTAGTTCCTCTCT
61589911  ACATGAGTTCCTTAGCAGTGAGTTCAATAAATGTTTTGGTATAAGGCCAC
61589961  CCTGGTTCAAAGAGGAGAAGGCTGTTGTCCTTGCTTCTCTGCGGTGCCTT
61590011  CTTCCTCCCAGGCCCTCAGACCTGCCTCTATTAAGTGGGAGAAGGGAGGC
61590061  CTGGGTAGGTAGGTCCCAGATCTTCAGATTGCCCGGGGAATGGGTCTGGA
61590111  GTCCTCTAGGCGTTGTTGTAAGCATTTTGCTGGGCCTTTAATGTAACTTT
61590161  CCAGTACAAATGATCTCTCTTTAAAATAAAACAAAAAAGCTAAGCTTAAA
61590211  ATTTTATAATGAGAATATTTACTTCACTATAGTAAGTCATCATATATCTA
61590261  TAAACACACATATATATACTCCCAATATACTTAACTTTTT
```

---

What is claimed is:

1. A method of identifying a subject as having, or as having an increased likelihood of having, omega-3 deficiency (O3D), comprising:
   a) obtaining a biological sample comprising nucleic acid from the subject; and
   b) determining a methylation percentage at a methylation site in the nucleic acid of the biological sample, wherein the methylation site is selected from the group consisting of cg27386326, cg16213375, cg10515671, cg03805684 and cg19610905 on chromosome 11, wherein a methylation percentage at the methylation site at or above a threshold value identifies the subject as having, or as having an increased likelihood of having, O3D.

2. A method of identifying a subject as having, or as having an increased likelihood of having, O3D, comprising:
   a) obtaining a biological sample comprising nucleic acid from the subject; and
   b) determining a methylation percentage at a methylation site in the nucleic acid of the biological sample, wherein the methylation site is in a chromosome region on chromosome 11 defined by and including base pair position 61,586,461 to base pair position 61,590,300, wherein a methylation percentage at the methylation site at or above a threshold value identifies the subject as having, or as having an increased likelihood of having, O3D.

3. The method of claim 1, wherein the biological sample is whole blood, the methylation site is cg27386326 and the threshold value is at or above about 84%.

4. The method of claim 1, wherein the biological sample is liver tissue, the methylation site is cg27386326 and the threshold value is at or above about 66%.

5. The method of claim 1, wherein the biological sample is saliva, the methylation site is cg27386326 and the threshold value is at or above about 70%.

6. The method of claim 1, wherein the biological sample is prostate tissue, the methylation site is cg27386326 and the threshold value is at or above about 93%.

7. The method of claim 1, wherein the biological sample is CD4+ T cells, the methylation site is cg27386326 and the threshold value is at or above about 70%.

8. The method of claim 1, further comprising the step of treating the subject with an omega-3 polyunsaturated fatty acid selected from the group consisting of docosahexaenoic acid (DHA), eicosapentaenoic acid (EPA), docosapentaenoic acid (DPA), stearidonic acid (SDA) and any combination thereof, if the subject is identified as having, or as having an increased likelihood of having, O3D.

9. The method of claim 8, wherein the omega-3 polyunsaturated fatty acid is administered as omega-3 polyunsaturated fatty acid-enriched food, dietary supplement, a medical food, prescription product or any combination thereof.

10. The method of claim 9, wherein the omega-3 polyunsaturated fatty acid-enriched food is selected from the group consisting of an oily fish, salmon, mackerel, trout and any combination thereof.

11. The method of claim 9, wherein the dietary supplement is selected from the group consisting of omega-3-enriched triglycerides, phospholipids, Krill oil, esters, ethyl esters and any combination thereof.

12. The method of claim 9, wherein the medical food and/or prescription product is a triglyceride, phospholipid or ester version of a omega-3 polyunsaturated fatty acid that contains a higher dose or concentration of omega-3 polyunsaturated fatty acid than dietary supplements, or any combination thereof.

13. The method of claim 1, wherein the subject is a pregnant female.

14. The method of claim 1, wherein the subject is an infant, child or adolescent that has, or is suspected of having, a diminished intelligence quotient (IQ), a developmental disorder, autism, attention deficit hyperactivity disorder (ADHD), attention deficit disorder (ADD), schizophrenia, depression, bipolar disorder, panic disorders, or any combination thereof as a result of, or associated with, O3D.

15. The method of claim 1, wherein the subject is an adult that has, or is suspected of having depression, bipolar disorder, schizophrenia, panic disorder, obsessive compulsive disorder (OCD), dementia, Alzheimer's disease, post traumatic stress disorder (PTSD) or any combination thereof, as a result of, or associated with O3D.

16. A method of identifying a subject as having, or as having an increased likelihood of having, long chain omega-6 polyunsaturated fatty acid excess (O6E), comprising:
   a) obtaining a biological sample comprising nucleic acid from the subject; and b) determining a methylation percentage at a methylation site in the nucleic acid of the biological sample, wherein the methylation site is selected from the group consisting of cg27386326, cg16213375, cg10515671, cg03805684 and cg19610905 on chromosome 11, wherein a methylation percentage at the methylation site at or below a threshold value identifies the subject as having, or as having an increased likelihood of having, O6E.

17. A method of identifying a subject as having, or as having an increased likelihood of having, O6E, comprising:
   a) obtaining a biological sample comprising nucleic acid from the subject; and
   b) determining a methylation percentage at a methylation site in the nucleic acid of the biological sample, wherein the methylation site is in a chromosome region on chromosome 11 defined by and including base pair position 61,586,461 to base pair position 61,590,300, wherein a methylation percentage at the methylation site at or below a threshold value identifies the subject as having, or as having an increased likelihood of having, O6E.

18. The method of claim 16, wherein the biological sample is whole blood, the methylation site is cg27386326 and the threshold value is at or below about 75%.

19. The method of claim 16, wherein the biological sample is liver tissue, the methylation site is cg27386326 and the threshold value is at or below about 40%.

20. The method of claim 16, wherein the biological sample is saliva, the methylation site is cg27386326 and the threshold value is at or below about 40%.

21. The method of claim 16, wherein the biological sample is prostate tissue, the methylation site is cg27386326 and the threshold value is at or below about 81%.

22. The method of claim 16, wherein the biological sample is CD4+ T cells, the methylation site is cg27386326 and the threshold value is at or below about 50%.

23. The method of claim 16, further comprising the step of treating the subject by reducing the consumption of medium-chain (18 carbon) omega-6 polyunsaturated fatty acids by the subject, reducing the consumption of long-chain omega-6 polyunsaturated fatty acids by the subject and/or administering medium-chain omega-3 polyunsaturated fatty acids and/or long-chain omega-3 polyunsaturated fatty acids to the subject, if the subject is identified as having, or as having an increased likelihood of having, O6E.

24. The method of claim 23, wherein the medium-chain omega-3 polyunsaturated fatty acids and/or the long-chain omega-3 polyunsaturated fatty acids are administered as a dietary supplement, a medical food, a prescription product, or any combination thereof.

25. The method of claim 24, wherein the medium-chain omega-3 polyunsaturated fatty acids are administered in a food, dietary supplement, medical food and/or prescription product enriched in 18 carbon omega-3 polyunsaturated fatty acids.

26. The method of claim 25, wherein the medium (18 carbon) omega-3 polyunsaturated fatty acids are selected from the group consisting of alpha-linolenic acids (ALA), stearidonic acids (SDA) and any combination thereof.

27. The method of claim 25, wherein the medium chain 18 carbon omega-3 polyunsaturated fatty acids are administered as flax seed, SDA-enriched vegetable oil, and any combination thereof.

28. The method of claim 24, wherein the long-chain omega-3 polyunsaturated fatty acid is selected from the group consisting of docosahexaenoic acid (DHA), eicosapentaenoic acid (EPA), docosapentaenoic acid (DPA) and any combination thereof.

29. The method of claim 24, wherein the long chain omega-3 polyunsaturated fatty acid is administered in a long chain omega-3 polyunsaturated fatty acid-enriched food is selected from the group consisting of an oily fish, salmon, mackerel, trout and any combination thereof.

30. The method of claim 24, wherein the dietary supplement is selected from the group consisting of long chain omega-3-enriched triglycerides, phospholipids, Krill oil, esters, ethyl esters and any combination thereof.

31. The method of claim 24, wherein the medical food and/or prescription product is a triglyceride, phospholipid or ester version of a long chain omega-3 polyunsaturated fatty acid that contains a higher dose or concentration of omega-3 polyunsaturated fatty acid than dietary supplements, or any combination thereof.

32. The method of claim 16, wherein the subject has, or is suspected of having, a disease caused by inflammation or an inflammatory response as a result of, or associated with, O6E.

33. The method of claim 16, wherein the subject has, or is suspected of having cardiovascular disease, cerebrovascular disease, atherosclerosis, diabetes, metabolic syndrome, cancer, arthritis, allergies, asthma, allergic rhinitis, inflammatory bowel disease, atopic dermatitis, psoriasis, an inflammatory brain disorder, Alzheimer's disease, multiple sclerosis and encephalitis, celiac disease, myopathy, autoimmune disease, systemic lupus erythematosus, (SLE), or any combination thereof.

34. The method of claim 16, wherein the step of determining the methylation percentage is carried out by a method selected from the group consisting of methylation specific PCR, whole genome bisulfite sequencing, HELP assay, ChIP on chip assays, methylated DNA immunoprecipitation, pyrosequencing of bisulfite treated DNA, methyl sensitive restriction enzymes, binding of methyl CpG binding proteins and immunocomplex formation between anti-methylated DNA antibodies and said methylated sites.

* * * * *

UNITED STATES PATENT AND TRADEMARK OFFICE
CERTIFICATE OF CORRECTION

PATENT NO. : 9,663,824 B2
APPLICATION NO. : 15/028323
DATED : May 30, 2017
INVENTOR(S) : Chilton et al.

Page 1 of 1

It is certified that error appears in the above-identified patent and that said Letters Patent is hereby corrected as shown below:

In the Specification

Column 1, Line 28: delete "EFS-Web is" and insert -- EFS-Web, is --

Column 8, Line 35: delete "70%, 72%, 72%" and insert -- 70%, 71%, 72% --

Column 13, Line 59: delete "ratio of AHA+" and insert -- ratio of ARA+ --

Column 28, Line 59: delete "(Petition 4490" and insert -- (Position 4490 --

Column 29, Line 1: delete "5'-CAATTCAGCAAATTTATCTGGG-3'" and insert
-- 5'-CAATTCAGCAAATTTATGTGGG-3' --

Signed and Sealed this
Twenty-seventh Day of March, 2018

Andrei Iancu
*Director of the United States Patent and Trademark Office*

SEQUENCE LISTING

<160> NUMBER OF SEQ ID NOS: 4

<210> SEQ ID NO 1
<211> LENGTH: 12950
<212> TYPE: DNA
<213> ORGANISM: Homo sapiens

<400> SEQUENCE: 1

```
ccaagcttcc cgtttcagcc ccatcctcga gaatgggctc ctttcctgct ccctctccgc    60
tcctgctggc gagtggagac cggcacctag gtccagacgc ggctgcgctg cctctcctag   120
ccatcgagac aggatgtgac tccctcccct ggccactgac ccctccctc cccaggcggc    180 ctgcatcctt gctctcctcc ctcctagcct acccagctcg ggttctgtc cccgcccaga   240 gacctgaggc tcggggctgc agatggaatg cacggcaggg aggcgggacc ctttgtttgt    300
```

```
gtgtgcgtgt tgttggcctc catccccact ccccagactc cacttctcca ggcctctctc      360
ccgccttttc atcccgcatc cgcaggacac ccaatcaccg ggcaacaggt atgatcaggc      420
gcctccgggc tttcctccga attagtcggt gtttggctcg gagtgcgtaa ctctgtctcc      480
cctgcactca gcctccggtc ccgccctctc ctgtgccccc gcctggctgc gctcaccgtg      540
gcatcctgcc cggcgtagtg gctgatgacc cgggagcccc ctggatgccg gcgggtgaac      600
tcgctgatgt tgtacacctt acggtcgatc actagccacc gctcctcgca ccctgagcgc      660
tgggccacct cgtcccaggt gaagtagcgc ggggtaggtc cctgagccgc ggtctcggcg      720
gccaccgggt cggggggccat agctggcctg gcgacgccgc gcgccgggcc agcaggggct      780
gtcaggcgcg tgctcggggt ccgcgggctc caggagtgga tttgctggcg cgcgcccaga      840
gccagccgcc tgcgcgccgg gttttcagca ccgcagggca gaccggcggg cctcgcagcg      900
cgcgttccca ttggccgagc ctcgtggcgc ggggagcgag atcccgtccc ccggtgggtc      960
ttgggcaact cacagctggg ctgccaacac gcgcccctc gcgggctccc taaaggcgtc     1020
gccgccggat tcgacttcct gacgtcaggc gggcatcgcg gcgttggctc caggggggcg     1080
ccgcggtagg aacagcggtt ctagtgcagg ccctgggtgc ggggccgcgc tgcaggagtg     1140
aatggactga ggggccaggg ctgcggggtg gccgcaggaa gggtgggcgg ggccgggggtt    1200
gaggtttttc cgtgcacgag gctgcccggg cggtcgcgga catcatcttt aggctgtgga     1260
tgccttggcc ggggtctcca gacgctgacc ctccagggtt ggaaactact gcctgcttgc     1320
cacgtcgtgc cgccaattgt gctgcccgaa gtagcagcct gagagccctt gaaagttgca     1380
gttatcttgt gaacagcata tttacggtct cttgggcttg gtggtggttg ggggagggct     1440
gttaatgctt taatttgttc aatgaaacat ttaaaatgcc ccacaatttt tataaccctg     1500
tttgcctctt tttgttttta ttttattgt attttggaaa aattcactgg gatccttgag     1560
tgatgatcct agcgtctcct gacccttagg tgtttcacct gaaaagcctg ggtcttcaag     1620
ctgaggcatt tctgttctag cctggaggcg cctaggagcc ctgggagact ttttaagcag     1680
agagatttgg catttagatc tctgggtttt agaggagtgg gaacgcacct aaaagtgggg     1740
ttgccagtta caaagctgtt gcagtcctga agagacccag agtttaggtc caaaatttta     1800
tttattcaac aaacactttta taaagcactt actgtgtgcc aggcactgtt cttagcgttt     1860
tgcaaacctt aactcattta attctcctaa caacccctatg aggttggaac aattaaccta     1920
atttacagtg aagaaactga gcccgggggga ggttattttg tcacacagct tgtaagtgga     1980
gggctgagat ttgaccctgg cctgtgctct gaactctcag gctctgccat atttctcatt     2040
acactggtat ttgggcactt caaagggaaa ggaaacataa ctgtcccaag cactgagcta     2100
gattctgagc acgtaggagt caggagaggg tgatacagaa tagactaggt gaaatatggc     2160
tagatttctg gtagaaaagg attaattcat tccatccaaa ttcttcattt tatagataag     2220
aaaattgagg ttcgaaatgg ggaaggggct taccaagttc ccatagggaa gtttagatgt     2280
cctgacttcc aggtaagatg ccaggctatt ggaccctgct caggaatgat ggtccacaca     2340
gctgcacctc tgtacagcca atattccttt tttaaaaacc ttgcccaaca acttggcagt     2400
gtctaatgcg agctacaaaa catttttctat tctttgatca agcagtttca ctcttggtaa     2460
agtaggggag actgtgcaaa gatgcagaaa tagccaattt aatagcaaaa actggaaata     2520
aacccgagtc ctgacaataa gaaaatcgcc aagcttattg ggatctgtta acacaatgaa     2580
gaattaaaga atgattttaa atggctagaa tgtgaactat attgatagat atagaatcct     2640
tccccgtgaa ataagcagaa cccaaagtag tatgggttcg ctgattacaa ctatataaga     2700
```

```
aattcatggg tattaaataa cagaagagag gtcctttaca taaaccattt ttcctatgtg    2760
actgtgcagt gggataaaag ctctcatact gctggtagaa gtgtaagttg attaaactgg    2820
aaaaaatagt ttgacaactt atatagaaat ttaagatttt tttttttttt gagatggagt    2880
ctcgctctgt cgcccaggct ggagtgcagt ggcctgatct cagcttgctg caagctccac    2940
ctcccaggtt catggcattc tcctgcctta gcctcccaag tagctgggac tacaggtgcc    3000
cgccaccacg cccagctaat tttgtttttg tattttagt agagttgggg tttcaccatg     3060
ttagccagga tggctttgat ctcctgacct cgtgatctgc ccgcctcggc ctcccaaagt    3120
gctgggatta caggcgtgag ccaccgcacc cggccagaat ttaggaatgt tttgaatact    3180
gaagagatga aaaaaaatag aaaaataaaa atgttcccaa taattccatg tttaggaata    3240
tagcctaagg aaatgttctt agaaaaatat ttataggtca ggcggggtgc ctcacgccta    3300
taatcctagc actttgggag gtcgaggcag gcggattgcc tgagctcagg agttcaagac    3360
cagcctgaac aaaagaaatc ggctgggcgt ggcggcgtgc gcctgtagtc ccagctactc    3420
gggaggctga ggcaggagaa ttgcttgaat ccgggaggca gaggttgcag tgagccgaga    3480
ttgtgccact gcactccagc ctgggcaaca agcaagatt ctatatccac acacaaaaaa     3540 agaaactat ttataaacaa aaatattca ttaaagcagt atctatgata gcgggaaatg      3600
gaaacactct aaatgcccat cagtgaaata ttttgcagac attgaaaata atgtcatctt    3660
tcctttaata cagaatcaag gaaaaatgtt ttatgtaaat ctttttattt attatacttt    3720
aagttttaag gtacatatgc acaacatgga ggtttgttac atatgtatac atgtgccatg    3780
ttggtgtgct gcacccatta actcgtcatt tagcattagg tatatctcct aatgctatcc    3840 ctccccccctc ccccgaatca aggaaaatta aataatatga tgtaagtttg gctacagaga   3900
taactgttct ataaaaagac taggttgggc gcggtggctc acacctgtaa tcccagcact    3960 tgggaggca gaggcaggtg gaccacctga ggccaggagc tcgagaccca cctggccaac     4020
atggtgaaac tctgtctcta ctaaaataca aaaattagtg cctgtaatcc cagctacttg    4080
ggaggctgag tcaggagaat cacctgggca acatggtgag actgcacctc agaaaaaacc    4140
aaaaaaccca taccacttgt aagataattc cttgatcaac cccacctacc tagaaccatt    4200
cattaagtgt tttatttaac atttgtgggg tgtctcctct ttgtattccc agcacctact    4260
ttggtaaggt gctgggaata caaagttcag tactatatgg gtcatgccta gtcatgtcta    4320
ctggaggaga gagacaagtg agtcacggat tataggtcag taggatagat gcaaattaaa    4380
ttcatcttac tcaggattta aacagcttat atgacatgac tttgcattca tgtttctttg    4440
cttttcatgt gttcttaggt cagtgtcatg tattttgcta cctccctaac gagcttataa    4500
tccaggatag ggctgtggat tctgtttata ctaccaatac atattcagag cacccttggtt   4560 tggagttcta ggtggaatcc cacataaatt tgctgaattg gccgggcgtg gcagctcatg    4620
cctgtaatcc ctgcactttg ggagggtgag gagggcggat cacctgaggt caggagctcc    4680
agacccactt ggccaacacg gtgaaaccct gtctctacta aaatacaaaa attagccggg   4740
tgtggtgggg ggtgcctgta atcccagcta ctttgtgggg gtgaggcagg agaatcgctt    4800
gaacccagga ggcaaaggtt gcagtgagcc gagattgcac cactgcactc cagcctgggt   4860
gacagagcca gactctgtct ctaaataaat aaataaataa aaaatttgct gaatcaactg    4920
atgatttcaa cctgaaaaaa tacaggtgag taagcctata ggccactagg caaatgtcgt    4980
gttgccctct catctcctta cccacctaca caggtggtca cacagactgc aataaaccca    5040
tatccaggtc aactaaagga aacctttgcc ttgcaggccc tgttgatcct aagggaactt    5100
```

```
gcctcatcct ggatatgaat cacatactta atttaggtt gccacttgtg aatactaact    5160
gttctggcca aattaatcct caaggaacag aacgaaatga gcttaagacc ctaatgccag    5220
gccaggcaca gtgactcgtg cctataatcc cagtgctttg ggaggctgag gtgggaggat    5280
tacttgagct caggagttgg agaccagcct agacaacata gtgagacccc ttcctaactg    5340
tcccaccatt ttctctctaa agaaaagaaa aaaaagacc ttaatgccga ttgtaatgaa     5400
gccataattg aataacctaa ctgccagtgg ctgttggaat aacctgaatt gtgagttcaa    5460
attttgatcc attttaacaa aagatcctaa acataatagt tggccaatag cctggatcct    5520
ttacaaagtc aacacatata ggagaagcaa taccggttgt gctcagcctc tgctgcagcc    5580
tcccctcagt agcagcccctt caggccatta aagaccaaaa ccattttga aaaatctgga    5640
tttctgtgaa attggataac ttatgggggt gcagtgacta caacacagta ggcactaata   5700
aagttgacag aatcagtctt tgttttaaga aaagtcatct gtaataattc tgcagattaa    5760
tgttaagtaa tattaaaaat aatttatgac atatagtgct taaactaaag ggagaatccc    5820
aatcatacct ctattagagg cagagcgaga gctagaaaca ggactctcat tttgctgcat    5880
tctaagagtg tgggagattg ggatggggca gaggcaggct catggaggaa ttcacgggat    5940
ttccttaatg cagtcttttt tttttttttg agacagagtc tcgctctgtc acccaggctg    6000
gagtgcagtg gtgctgtctt ggctcactgc aacctccgcc tcagggctc acgccattct     6060
cctgcctcag cctcctgagt agctgggact acaggcgtct gccaccacgc ctggctaatt    6120
ttttgtattt tcagtagaga caaagtttca ccatgttagc caggatggtc tccatctcct    6180
gacttggtga tccacccgcc tcagactccc aaagtgctgg gattacaggc gtgagccacc   6240
gcgcccggcc cagtcttctt atcattgtat agaatataga tgccttaggg acagatatat   6300
taaacccact gttttataga caaggtgaca gatccaaaga gctgaagcca cacatgaaat   6360
ttagtatatt tggggctaga atttacccca gaacttattt ataacttta gttcctctct     6420
acatgagttc cttagcagtg agttcaataa atgttttggt ataaggccac cctggttcaa   6480
agaggagaag gctgttgtcc ttgcttctct gcggtgcctt cttcctccca ggccctcaga   6540
cctgcctcta ttaagtggga aagggaggc ctgggtaggg aggtcccaga tcttcagatt    6600
gccccggggaa tgggtctgga gtcctctagg cgttgttgta agcattttgc tgggccttta    6660
atgtaacttt ccagtacaaa tgatctctct ttaaaataaa acaaaaaagc taagcttaaa   6720
attttataat gagaatattt acttcactat agtaagtcat catatatcta taaacacaca    6780
tatatatact cccaatatac ttaactttt ccctattgtt ggacatttgt gtagaagttt     6840
cgcttgtata aatgttgcga tggatatttt tgtatataga tattggtttc tatttctgaa   6900
catttttctta ggataaaattc tacatgtgta attagtggat caggtaataa catttttagt   6960
ctcttgtcat ttgttgccaa attaccaatt tactgctgaa ttatttcaca ggtattcctc    7020
gagcacttag tatgcattcc ttagttttac tgcacttctt atcaccagaa caggaaagga   7080
atggtgtcct acagctcctt gaccaagtac ctctccacca atactatgag cactaaagat   7140
gcagcaacga agcactagac tctgggatgt gaagatctca aattctattc tctgtgcact   7200
tcagagttgg agaaggatcc atcaagtttc agtagaatgt accaaggaag ggaggcaatg   7260
tggtagaatg gaaagaataa ggattgtagt tgagacacct gcaacctgga cctgctagtc    7320
cacctactgc tgtgtaatct tggacattat gtccacctct atgggtttcg gatccttat     7380
ctgtaaagtg aagagattgt ccagatgctt tccagcacta gcaatctgtg ctttaaagtt    7440
ttacctaaca taccataccct tttatcaatg tccacctaga gataataacc cagcttattt    7500
```

```
tatttgagtt ttgagacagg gtcttgctct gtcttgcact ccagctggag tgcagtggca      7560
cgatcatgga tcactgaagt ctccacctct gcggttcaag cattcctccc acctcagcct      7620
cccgagtagc tgggactata ggcatgcacc accacatcca actaattttt tatattttg      7680 tacagacagg gtctcactgt gttgcccagg ctggtctcaa actcctgggc tcaagtgatc      7740
ctcccacctt ggcctcccaa agtgttggga ttacaggtgt gagccaccac gcctggccta      7800
acccagtttc ttagataggg tccccagcct gtcatttaag gcatctaaat ttgatgcact      7860
tactaagttg atgccatttt tgttgttgaa aattattcat ttttttaaaaa tagttatgac      7920 tttcaccaca tattaataaa tcattatcta gtgagcttgg ttaaagtttg acctcaccaa      7980
tattgctagt taagaaaata catgtatggc actttcacat accttgtgtc ctttgagcct      8040
cgttattaaa atagatgaga taggttagaa atcactatct ccgctgggtg cggtggctta      8100
tgcctgtaat cccagcactt tgggaggccg aggtgggcag atcacctgag gtcgggagtt      8160
cgagaccaac ctcaccaaca tggagaaacc ctgtctctac taaaaataca aaattagctg      8220
ggtgtggtgg cacatgccat gtaatcccag ctactcggga ggctgaggca ggagaatcgc      8280
ttgaacccgg gaggcagagg ttgcagtgag ccaagattgc accactgcac tccagcctgg      8340
gggatagagt gagactccat cttggggaaa aaaaaagag agagagagag agagagagag      8400
agagagagag agagagggag ggagggaggg agggagggag ggagagagag agagagagag      8460
agagagagag agaaagaaag aaaggaaaga agaaagaaa gaaagaaaga aaatcactg       8520 tctccttttt atcatgagga aactgaaggt cagagacaga ggtctaacat cacatggtag      8580
gtatgggaaa ggaatactgt agcggtctgt aattgctttt ggtttgtgac ttcccacaaa      8640
aaggaacaga ccctgttccc caaagcccag gtctgctgct tggcttatga cctacaccta      8700
atagagtaac tcagccgtct gataacagtg gcccaatggt tagcatctga tgcagagccc      8760
attaaactgg aattaatcct tgggagcagg gaatggggga gaattatttc tgctagcgta      8820
gcttagcaaa tacagccata tttttttgtc acatggagga gacccttctg cagtaagaga      8880
gaatcaggtg ttggccgggt gcagtggctc acgcctgtaa tcccagcact tgggaggct      8940 gaggtgggca gatcacgagg tcagaagatc gagaccatca tggccaacat ggtgaaaccc      9000
catctctact aaaaatacaa aaattatctg gcatggtgc cacccaccac ggcctcctaa      9060
agtgctggga ttataggcat aagccactgc tcccagccta ggtgtttcaa acataacgtt      9120
aaaatagaat ttttaatttt tcaccctgt actaactctg ttccctcatc ttggtaaatg      9180
gtcccattat ctattcattt gctcaactca aatgctagaa tcagactat ttctcttatt      9240 ccttcatctc taccatcacc cctgcccctg tacctccaac taatgcggtc ttgattctac      9300
ctccaaagga tattctaggc tgggcagggt ggctcacgcc tgtaatccca gcactctggg      9360
aggctgaggt gggcagatca cctgaggtca ggagtttgag accagcctgg ccaacatggt      9420
gaaaccctgt ctctactaaa aatataaaaa ttagccgggc atggtggcgg gtgcttgtaa      9480
tcccagctac tcaggaggct gaggcagtag aaccatttga acccatgagg tggaggttgc      9540
agtgagctga gatcgcacca ctgcactcca gcctgggcga cagagtgaga ccctgtctca      9600
aaaaaaaaaa aaaagaaaag aaaagccctt tgggaggcc gaggcaggtg gatcacgagg      9660
tcaggagatc gagaccatcc tggctaacac ggtgaaaccc cgtctctact aaaaatacaa      9720 aaaattagc cgggtgtggt ggcaggcgcc tgtagtccca gctactcggg aggctgaggc      9780
aggagaatgg cgtgaacctg ggaggtggag cttgcagtga gtagagatcg caccactgca      9840
ctctagcctg ggcaacagag tgagactgca tctcaaaaaa aaattagagg gcagggaggc      9900
```

```
acatggcagt gtccagtgtg gggtcagccc cctaaagttc tctcttaatt caggcctccc      9960
ctcccctctc ctcgagcact gccctcatct ttgaactcat cactgttccc cagtttctcc     10020
cgtacatccc agtccagccc cagcctctgg agttatcttt ctacaccatg gatctgatca     10080
cagtacacct gctttacgga tgtccaagcc tcctccatgg taaagtcctc ccttcctacc     10140
ccttactgag gctgctgggg cttttctcaa tttgagcccc atctaccgcc ggcctcattg     10200
gagccattct ttgaacttca ttcattcatt tgtgtcttca acacatgttt ttatgttttt     10260
tcaggaccta ccctggctgg tactgtgctg ggagccgctg gggaccccag gccctggccg     10320
gtccacgctt ctcagccacc ctacacaggc cacccatacg tgctcccttt tagggcctga     10380
accttcaaag cctctgtgag atactccctg gttctgcctt tcagctatca ctccctgctc     10440
cgagctccac acccttttaca aatgttcatt aaagttatct atatggtatg ttaatccatt     10500
tctgagaaaa taattttctt ggttccattt ccgtcaacgt ttgacagtcc tcaaggccac     10560
catactctct ggaggtcttg cttcatcctc ttattttgta cagaaggctt tgtttggga      10620 tgtctgctca cactcaaaga cagagaggcc ttactgtctt tatgtctgca gtctgtggag     10680
tgaatgaagg atgctcaggg ctgacaccag catgaaatgt gatgggagag gttggggact     10740
gtgtgaatgt gaggaaaggg agcccatctg ccccccaag tacaacccca ccagttgggc      10800
agagtgatcc ccccaccacc cctgcattgc tgtgaaattt agattgggca gggcccgttt     10860
gaccatctct ctcaatctca ggctctccat tttcaagtga gatgtaataa tatgcgtcct     10920
gtttacctct cagcctgtga tgagaatcta atgattaggg tgtgctagca cacaggcacc     10980
tgtaaatccc attgaaatct gagggcccta taactcctct agtgattccc aagcctcgtg     11040 cacccccaccc tctctgttca tccttacttc ccacgtgtcc cgttagccct ccggatgcag    11100
tcaggcccat ttcccccagg acgcccggca ctaagccgcc ccatccagct ggggtctgag     11160
gggcctgtct cttgccccac gcctaaaaga cctaaccctc ctcctatccc ttcgatacgg     11220
cagtctttat ttgctggagt ctgcacaaca tcactgccca atgatgtgtc tgcttccacg     11280
attcccaaag agactgagct tactgagacc agggcaagga ccgcgccagt tcctcatcgc     11340
ccccttcctc tgccttcccc tcccttcccc ctcaccgcag ccatggcgcc cagaccaaga     11400
aagcagagca gaggttccgc aattcttttc taagattgtc tgactagagg gttcaaagcc     11460
ctctaatcca aggccggctt gtgtctctag ggaggttgca gaaaggcgcc agaatgtgga     11520
tggcgcggac aatgtgggat actggagtct cgactgccgc gcgccaagga agggcgtcac     11580
ctagccaagc cggccctgga gttgagtgcc ccgcagcccg ccggtccacc cgcccggccg     11640
cttgctggca ccctggtggc cgcgccggct ttgtgtcggc atcaggtgca aaccccccaga    11700 gcgccgggcg tgcgcgcacg cgccccggag cgcgcggagc ccattcgttg ccccccaccgg    11760 gatctcctct aggatctcct ccggcgcccg gggccggaga gtggggagg gaggaggtcg      11820 gacacgtagc ctgcctcgca gcagggctcg actccacgcg ggaggcgggg ggagccgggg    11880
acccgccgct ccagcccgct ggccttcgaa agatcctcct gggccaatgg caggcggggc     11940
gacgcgaccg gattggtgca ggcgctctgc tgatcgctgt ggaaactcgg gcggcgggga    12000
acgcgggagg atgtggaacc cgaggcgggg ggagccggag gggcgggcag aggaggtgtc     12060
gaggccctga gctcccgggg agttttact ggaggcaaaa gtccatagcg ggagggctga      12120
gggaggggcg gaggaagggg accgcttggg ggcactggga agccagggat cctccgccag    12180
gaaggcaggg acactcccga gcgcaggcga gaaggctggg ggaggggcg cggtgggagg      12240 agtaggagaa gacaaaagcc gaaagcgaag agggcccggg ctgcacacac cggctgggag    12300
```

| | |
|---|---|
| gcagccgtct gtgcagcgag cagccggcgc ggggaggccg cagtgcacgg ggcgtcacag | 12360 |
| tcggcaggca gcatggggaa gggagggaac caggcgagg gggccgccga gcgcgaggtg | 12420 |
| tcggtgccca ccttcagctg ggaggagatt cagaagcata acctgcgcac cgacaggtgg | 12480 |
| ctggtcattg accgcaaggt ttacaacatc accaaatggt ccatccagca cccgggggc | 12540 |
| cagcgggtca tcgggcacta cgctggagaa gatgcaacgg taagggtctg ggggcgcccc | 12600 |
| agccacctt ctctgctgca ggcggagtca ggatccctgg ctccccgtgg gccaaacaga | 12660 |
| cctccggcgc tgaatggagc ttgggacgtc ctgtagggaa ggaaagtgca tctattgcac | 12720 |
| tcgtaccccc tccccaatcc tcctcctcct ctgggccgac tggggtggag accggatctg | 12780 |
| ggacccgggg aggcggcgct gcggtgaaag tcccagcggt ggagaacagg gcaagcatct | 12840 |
| accgcgcgcg ccgggaccca cgcgtcctcc ccttcctcgg ggtttgtctg gaggcaggga | 12900 |
| ctccccaaga ggggcgctcg ggccagacgg ctttggcgcc cccagcgggg | 12950 |

<210> SEQ ID NO 2
<211> LENGTH: 3840
<212> TYPE: DNA
<213> ORGANISM: Homo sapiens

<400> SEQUENCE: 2

| | |
|---|---|
| gcctcccaag tagctgggac tacaggtgcc cgccaccacg cccagctaat tttgtttttg | 60 |
| tattttagt agagttgggg tttcaccatg ttagccagga tggctttgat ctcctgacct | 120 |
| cgtgatctgc ccgcctcggc ctcccaaagt gctgggatta caggcgtgag ccaccgcacc | 180 |
| cggccagaat ttaggaatgt tttgaatact gaagagatga aaaaaaatag aaaaataaaa | 240 |
| atgttcccaa taattccatg tttaggaata tagcctaagg aaatgttctt agaaaaatat | 300 |
| ttataggtca ggcggggtgc ctcacgccta taatcctagc actttgggag gtcgaggcag | 360 |
| gcggattgcc tgagctcagg agttcaagac cagcctgaac aaaagaaatc ggctgggcgt | 420 |
| ggcggcgtgc gcctgtagtc ccagctactc gggaggctga ggcaggagaa ttgcttgaat | 480 |
| ccgggaggca gaggttgcag tgagccgaga ttgtgccact gcactccagc ctgggcaaca | 540 |
| aagcaagatt ctatatccac acacaaaaaa agaaaactat ttataaacaa aaatattca | 600 |
| ttaaagcagt atctatgata gcgggaaatg gaaacactct aaatgcccat cagtgaaata | 660 |
| ttttgcagac attgaaaata atgtcatctt tcctttaata cagaatcaag gaaaaatgtt | 720 |
| ttatgtaaat cttttatttt attatacttt aagttttaag gtacatatgc acaacatgga | 780 |
| ggtttgttac atatgtatac atgtgccatg ttggtgtgct gcacccatta actcgtcatt | 840 |
| tagcattagg tatatctcct aatgctatcc ctcccccctc ccccgaatca ggaaaatta | 900 |
| aataatatga tgtaagtttg gctacagaga taactgttct ataaaaagac taggttgggc | 960 |
| gcggtggctc acacctgtaa tcccagcact tgggaggca gaggcaggtg gaccacctga | 1020 |
| ggccaggagc tcgagaccca cctggccaac atggtgaaac tctgtctcta ctaaaataca | 1080 |
| aaaattagtg cctgtaatcc cagctacttg ggaggctgag tcaggagaat cacctgggca | 1140 |
| acatggtgag actgcacctc agaaaaaacc aaaaaaccca taccacttgt aagataattc | 1200 |
| cttgatcaac cccacctacc tagaaccatt cattaagtgt tttatttaac atttgtgggg | 1260 |
| tgtctcctct ttgtattccc agcacctact ttggtaaggt gctgggaata caaagttcag | 1320 |
| tactatatgg gtcatgccta gtcatgtcta ctggaggaga gagacaagtg agtcacggat | 1380 |
| tataggtcag taggatagat gcaaattaaa ttcatcttac tcaggattta aacagcttat | 1440 |
| atgacatgac tttgcattca tgtttctttg cttttcatgt gttcttaggt cagtgtcatg | 1500 |

```
tattttgcta cctccctaac gagcttataa tccaggatag ggctgtggat tctgtttata    1560
ctaccaatac atattcagag caccttggtt tggagttcta ggtggaatcc cacataaatt    1620
tgctgaattg gccgggcgtg gcagctcatg cctgtaatcc ctgcactttg ggagggtgag    1680
gagggcggat cacctgaggt caggagctcc agacccactt ggccaacacg gtgaaaccct    1740
gtctctacta aaatacaaaa attagccggg tgtggtgggg ggtgcctgta atcccagcta    1800
ctttgtgggg gtgaggcagg agaatcgctt gaacccagga ggcaaaggtt gcagtgagcc    1860
gagattgcac cactgcactc cagcctgggt gacagagcca gactctgtct ctaaataaat    1920
aaataaataa aaaatttgct gaatcaactg atgatttcaa cctgaaaaaa tacaggtgag    1980
taagcctata ggccactagg caaatgtcgt gttgccctct catctcctta cccacctaca    2040
caggtggtca cacagactgc aataaaccca tatccaggtc aactaaagga aacctttgcc    2100
ttgcaggccc tgttgatcct aagggaactt gcctcatcct ggatatgaat cacatactta    2160
attttaggtt gccacttgtg aatactaact gttctggcca aattaatcct caaggaacag    2220
aacgaaatga gcttaagacc ctaatgccag gccaggcaca gtgactcgtg cctataatcc    2280
cagtgctttg ggaggctgag gtgggaggat tacttgagct caggagttgg agaccagcct    2340
agacaacata gtgagacccc ttcctaactg tcccaccatt ttctctctaa agaaaagaaa    2400 aaaaagacc ttaatgccga ttgtaatgaa gccataattg aataacctaa ctgccagtgg    2460
ctgttggaat aacctgaatt gtgagttcaa attttgatcc attttaacaa agatcctaa     2520 acataatagt tggccaatag cctggatcct ttacaaagtc aacacatata ggagaagcaa    2580
taccggttgt gctcagcctc tgctgcagcc tcccctcagt agcagccctt caggccatta    2640
aagaccaaaa ccattttga aaaatctgga tttctgtgaa attggataac ttatgggggt     2700
gcagtgacta caacacagta ggcactaata aagttgacag aatcagtctt tgttttaaga    2760
aaagtcatct gtaataattc tgcagattaa tgttaagtaa tattaaaaat aatttatgac    2820
atatagtgct taaactaaag ggagaatccc aatcatacct ctattagagg cagagcgaga    2880
gctagaaaca ggactctcat tttgctgcat tctaagagtg tgggagattg ggatggggca    2940
gaggcaggct catggaggaa ttcacgggat ttccttaatg cagtcttttt ttttttttg     3000 agacagagtc tcgctctgtc acccaggctg gagtgcagtg gtgctgtctt ggctcactgc    3060
aacctccgcc tccagggctc acgccattct cctgcctcag cctcctgagt agctgggact    3120
acaggcgtct gccaccacgc ctggctaatt ttttgtattt tcagtagaga caaagtttca    3180
ccatgttagc caggatggtc tccatctcct gacttggtga tccacccgcc tcagactccc    3240
aaagtgctgg gattacaggc gtgagccacc gcgcccggcc cagtcttctt atcattgtat    3300
agaatataga tgccttaggg acagatatat taaacccact gttttataga caaggtgaca    3360
gatccaaaga gctgaagcca cacatgaaat ttagtatatt tggggctaga atttacccca    3420
gaacttattt ataactttta gttcctctct acatgagttc cttagcagtg agttcaataa    3480
atgttttggt ataaggccac cctggttcaa agaggagaag gctgttgtcc ttgcttctct    3540
gcggtgcctt cttcctccca ggccctcaga cctgcctcta ttaagtggga gaagggaggc    3600
ctgggtaggt aggtcccaga tcttcagatt gcccggggaa tgggtctgga gtcctctagg    3660
cgttgttgta agcattttgc tgggcctttta atgtaacttt ccagtacaaa tgatctctct    3720
ttaaaataaa acaaaaaagc taagcttaaa attttataat gagaatattt acttcactat    3780
agtaagtcat catatatcta taaacacaca tatatatact cccaatatac ttaactttt     3840
```

```
<210> SEQ ID NO 3
<211> LENGTH: 24
<212> TYPE: DNA
<213> ORGANISM: Artificial
<220> FEATURE:
<223> OTHER INFORMATION: PCR primer sequence

<400> SEQUENCE: 3
atgatgtaag tttggctaca gaga                                              24

<210> SEQ ID NO 4
<211> LENGTH: 22
<212> TYPE: DNA
<213> ORGANISM: Artificial
<220> FEATURE:
<223> OTHER INFORMATION: PCR primer sequence

<400> SEQUENCE: 4
caattcagca aatttatgtg gg                                                22
```